US011299746B2

(12) United States Patent
Van Schie et al.

(10) Patent No.: US 11,299,746 B2
(45) Date of Patent: Apr. 12, 2022

(54) DISEASE RESISTANT PEPPER PLANTS

(71) Applicant: Enza Zaden Beheer B.V., Enkhuizen (NL)

(72) Inventors: Christianus Cornelis Nicolaas Van Schie, Amsterdam (NL); Karin Ingeborg Posthuma, Enkhuizen (NL); Tieme Zeilmaker, Amersfoort (NL); Geert Johannes De Boer, IJmuiden (NL)

(73) Assignee: Enza Zaden Beheer B.V., Enkhuizen (NL)

( * ) Notice: Subject to any disclaimer, the term of this patent is extended or adjusted under 35 U.S.C. 154(b) by 0 days.

(21) Appl. No.: 16/921,770

(22) Filed: Jul. 6, 2020

(65) Prior Publication Data
US 2020/0332313 A1 Oct. 22, 2020

Related U.S. Application Data

(63) Continuation-in-part of application No. 15/314,778, filed as application No. PCT/EP2015/063682 on Jun. 18, 2015, now abandoned.

(30) Foreign Application Priority Data
Jun. 18, 2014 (WO) .................. PCT/EP2014/062802

(51) Int. Cl.
C12N 15/82 (2006.01)
(52) U.S. Cl.
CPC .................. *C12N 15/8282* (2013.01)
(58) Field of Classification Search
CPC ............ C12N 15/8282; C12N 15/8279; C12N 15/8281
See application file for complete search history.

(56) References Cited

U.S. PATENT DOCUMENTS

| | | | |
|---|---|---|---|
| 5,866,776 A | 2/1999 | Marie de Wit | |
| 6,100,451 A | 8/2000 | Chappell et al. | |
| 6,271,439 B1 | 8/2001 | Gurmukh et al. | |
| 7,323,338 B2 | 1/2008 | Amir | |
| 7,777,097 B2 | 8/2010 | Glazebrook et al. | |
| 8,575,432 B2 | 11/2013 | Van Den Ackerveken et al. | |
| 8,742,207 B2 | 6/2014 | Van Damme et al. | |
| 9,121,029 B2 | 9/2015 | Van Damme et al. | |
| 9,546,373 B2 | 1/2017 | Van Damme et al. | |
| 9,932,600 B2 | 4/2018 | Van Damme et al. | |
| 9,994,861 B2 | 6/2018 | Van Damme et al. | |
| 10,501,754 B2 | 12/2019 | Van Damme et al. | |
| 10,597,675 B2 | 3/2020 | Van Schie et al. | |
| 10,787,673 B2 | 9/2020 | Van Damme et al. | |
| 2003/0172396 A1 | 9/2003 | Cohen | |
| 2004/0031072 A1 | 2/2004 | La Rosa et al. | |
| 2006/0041949 A1 | 2/2006 | Xu et al. | |
| 2006/0048240 A1 | 3/2006 | Alexandrov | |
| 2006/0143729 A1 | 6/2006 | Alexandrov | |
| 2009/0210965 A1* | 8/2009 | McCarthy | A01H 5/08 800/278 |
| 2010/0115658 A1* | 5/2010 | Van Damme | C12N 15/01 435/468 |
| 2012/0227134 A1 | 9/2012 | Schon et al. | |
| 2014/0289897 A1 | 9/2014 | Van Damme et al. | |
| 2015/0052634 A1 | 2/2015 | Park et al. | |
| 2015/0059017 A1 | 2/2015 | Van Damme et al. | |
| 2016/0160233 A1 | 6/2016 | Van Schie et al. | |
| 2016/0272987 A1 | 9/2016 | Gil et al. | |
| 2016/0298130 A1 | 10/2016 | Van Damme et al. | |
| 2016/0298131 A1 | 10/2016 | Van Damme et al. | |
| 2016/0312239 A1 | 10/2016 | Gan | |
| 2016/0326543 A1 | 11/2016 | Van Damme et al. | |
| 2016/0326544 A1 | 11/2016 | Van Damme et al. | |
| 2016/0333370 A1 | 11/2016 | Van Schie et al. | |
| 2017/0283826 A1 | 10/2017 | Van Schie et al. | |
| 2017/0314039 A1 | 11/2017 | Van Schie et al. | |
| 2018/0135071 A9 | 5/2018 | Van Damme et al. | |
| 2018/0320191 A1 | 11/2018 | Van Damme et al. | |
| 2018/0334681 A1 | 11/2018 | Van Schie et al. | |
| 2019/0144878 A1 | 5/2019 | Van Damme et al. | |
| 2019/0203223 A1 | 7/2019 | Van Schie et al. | |
| 2019/0309319 A1 | 10/2019 | Van Schie et al. | |
| 2019/0316143 A1 | 10/2019 | Van Damme et al. | |
| 2020/0040354 A1 | 2/2020 | Van Damme et al. | |

(Continued)

FOREIGN PATENT DOCUMENTS

| | | |
|---|---|---|
| EP | 0474857 A1 | 3/1992 |
| EP | 1033405 A2 | 9/2000 |

(Continued)

OTHER PUBLICATIONS

Qin, Cheng, et al. "Whole-genome sequencing of cultivated and wild peppers provides insights into Capsicum domestication and specialization." Proceedings of the National Academy of Sciences 111.14 (2014): 5135-5140. (Year: 2014).*
"Federal Register", Feb. 9, 2011, 76(27):7162-7175, 14 pages.
Alignment of cucumber DMR6-specific primers with XP_008462902. 2, filed on May 5, 2019 in Opposition proceedings against EP2455475, 1 page.
Alignment of primers with the two copies of the cabbage DMR6 Gene, filed in Opposition against EP2455477, dated Sep. 7, 2016, 4 pages.

(Continued)

*Primary Examiner* — Weihua Fan
(74) *Attorney, Agent, or Firm* — Morrison & Foerster LLP

(57) ABSTRACT

The present invention relates to *Phytophthora capsici* resistant *Capsicum annuum* plants wherein said resistance is conferred by a combination of two genes. The present invention further relates to the use of these genes for providing *Phytophthora capsici* resistant *Capsicum annuum* plants and proteins encoded by the present genes.

10 Claims, 14 Drawing Sheets

(12 of 14 Drawing Sheet(s) Filed in Color)

Specification includes a Sequence Listing.

(56) References Cited

U.S. PATENT DOCUMENTS

| | | | |
|---|---|---|---|
| 2020/0157560 | A1 | 5/2020 | Van Schie et al. |
| 2021/0071195 | A1 | 3/2021 | Zeilmaker |
| 2021/0115457 | A1 | 4/2021 | Van Damme et al. |

FOREIGN PATENT DOCUMENTS

| | | | |
|---|---|---|---|
| EP | 2455473 A1 | 5/2012 | |
| WO | WO-1991015585 A1 | 10/1991 | |
| WO | WO-1996036697 A1 | 11/1996 | |
| WO | WO-1998004586 A2 | 2/1998 | |
| WO | WO-1998032325 A1 | 7/1998 | |
| WO | WO-1999045125 A2 | 9/1999 | |
| WO | WO-2000070016 A2 | 11/2000 | |
| WO | WO-2000078981 A1 | 12/2000 | |
| WO | WO-2001055347 A1 | 8/2001 | |
| WO | WO-2001061021 A2 | 8/2001 | |
| WO | WO-2002061101 A2 | 8/2002 | |
| WO | WO-2002088301 A2 | 11/2002 | |
| WO | WO-2003000906 A2 | 1/2003 | |
| WO | WO-2004024079 A2 | 3/2004 | |
| WO | WO-2006032707 A2 | 3/2006 | |
| WO | WO-2006047358 A1 | 5/2006 | |
| WO | WO-2006047495 A2 | 5/2006 | |
| WO | WO-2007051483 A1 | 5/2007 | |
| WO | WO-2007051626 A2 | 5/2007 | |
| WO | WO-2008092505 A1 | 8/2008 | |
| WO | WO-2008092659 A1 | 8/2008 | |
| WO | WO-2008153927 A2 | 12/2008 | |
| WO | WO-2009009142 A2 | 1/2009 | |
| WO | WO-2013086499 A2 | 6/2013 | |
| WO | WO-2015011101 A1 | 1/2015 | |
| WO | WO-2015029031 A1 | 3/2015 | |
| WO | WO-2015106796 A1 | 7/2015 | |
| WO | WO-2015193418 A1 | 12/2015 | |
| WO | WO-2016164658 A1 | 10/2016 | |
| WO | WO-2019042935 A1 | 3/2019 | |

OTHER PUBLICATIONS

Amended claims filed after receipt of (European) search report, filed Feb. 10, 2017, during prosecution of EP3094722, 1 page.
Amended claims filed after receipt of (European) search report, filed Jan. 22, 2013, during prosecution of EP2455482, 2 pages.
Amended claims filed after receipt of (European) search report, filed Jan. 22, 2013, during prosecution of EP2455483, 2 pages.
Amended claims filed after receipt of (European) search report, filed Jul. 30, 2009, during prosecution of EP2115147, 5 pages.
Amended claims filed after receipt of (European) search report, filed Nov. 19, 2012, during prosecution of EP2455479, 2 pages.
Amended claims filed after receipt of (European) search report, filed Sep. 5, 2016, during prosecution of EP3024929, 2 pages.
Amended claims submitted by applicant on Sep. 25, 2017 for EP2681234 examination proceedings, filed Dec. 7, 2017 in Opposition against EP2455477, 1 page.
Amended claims with annotations, filed Apr. 26, 2018, during appeal of EP2455473, 2 pages.
Amended claims with annotations, filed Sep. 10, 2018, during appeal of EP2455473, 14 pages.
Amended claims, filed Apr. 17, 2018, during prosecution of EP3167051, 1 page.
Amended claims, filed Aug. 17, 2017, during prosecution of EP3167051, 2 pages.
Amended claims, filed Aug. 20, 2010, during prosecution of EP2115147, 4 pages.
Amended claims, filed Dec. 21, 2017, during prosecution of EP3024929, 2 pages.
Amended claims, filed Feb. 2, 2012, during prosecution of EP2115147, 2 pages.
Amended claims, filed Jan. 17, 2018, during prosecution of EP3094722, 1 page.
Amended claims, filed Mar. 17, 2017, during prosecution of EP2455474, 1 page.
Amended claims, filed May 26, 2011, during prosecution of EP2115147, 3 pages.
Amended claims, filed May 28, 2018, during prosecution of EP3094722, 1 page.
Amended claims, filed May 28, 2018, during prosecution of EP3167051, 1 page.
Amended claims, filed Oct. 15, 2018, during prosecution of EP3024929, 1 page.
Amended description with annotations, filed Apr. 17, 2018, during prosecution of EP3167051, 17 pages.
Amended description with annotations, filed Aug. 30, 2016, during prosecution of EP2455475, 30 pages.
Amended description with annotations, filed Aug. 30, 2016, during prosecution of EP2455481, 29 pages.
Amended description with annotations, filed Jan. 17, 2018, during prosecution of EP3094722, 19 pages.
Amended description with annotations, filed Jul. 21, 2016, during prosecution of EP2455476, 29 pages.
Amended description with annotations, filed Jul. 21, 2016, during prosecution of EP2455480, 29 pages.
Amended description with annotations, filed Jun. 5, 2012, during prosecution of EP2115147, 7 pages.
Amended description with annotations, filed Mar. 17, 2017, during prosecution of EP2455474, 29 pages.
Amended description with annotations, filed May 28, 2018, during prosecution of EP3094722, 19 pages.
Amended description with annotations, filed May 28, 2018, during prosecution of EP3167051, 34 pages.
Amended description with annotations, filed Oct. 10, 2016, during prosecution of EP2455474, 29 pages.
Amended description with annotations, filed Oct. 10, 2016, during prosecution of EP2455478, 29 pages.
Amended description with annotations, filed Oct. 21, 2013, during prosecution of EP2455473, 11 pages.
Amended description with annotations, filed Oct. 21, 2013, during prosecution of EP2455477, 11 pages.
Amended description with annotations, filed Oct. 5, 2016, during prosecution of EP2455479, 30 pages.
Amendments received before examination, filed Aug. 17, 2017, during prosecution of EP3167051, 3 pages.
Amendments received before examination, filed Feb. 10, 2017, during prosecution of EP3094722, 2 pages.
Amendments received before examination, filed Jan. 22, 2013, during prosecution of EP2455482, 3 pages.
Amendments received before examination, filed Jan. 22, 2013, during prosecution of EP2455483, 3 pages.
Amendments received before examination, filed Nov. 19, 2012, during prosecution of EP2455479, 3 pages.
Amendments received before examination, filed Sep. 5, 2016, during prosecution of EP3024929, 2 pages.
Analysis performed by Dr. T. Zeilmaker using the protein analysis program PROVEAN, filed Sep. 15, 2017, in Opposition against EP2455473, 3 pages.
Annex B, filed by the Applicant on Aug. 30, 2016, in case EP2455475 during examination, 6 pages.
Annexes (other than cited documents) regarding appeal procedure, Sep. 10, 2018, filed during appeal of EP2455473, 6 pages.
Applicant request for correction/amendment of the text proposed for grant and amended claims, filed Jan. 15, 2019 in case EP3167051, 3 pages.
Applicant request for correction/amendment of the text proposed for grant with amended claims and description, filed Feb. 5, 2019 in case EP3094722, 22 pages.
Applicant request for correction/amendment of the text proposed for grant, filed Aug. 17, 2017 in case EP2455475, 1 page.
Ardi et al., (1998). "Involvement of Epicatechin Biosynthesis in the Activation of the Mechanism of Resistance of Avocado Fruits to Colletotrichum Gloeosporioides", Physiological and Molecular Plant Pathology, 53:269-285.
Aubert et al., (1998). "Transport, Compartmentation, and Metabolism of Homoserine in Higher Plant Cells", Plant Physiol., 116:547-557.

(56) References Cited

OTHER PUBLICATIONS

Auxiliary request containing amended claims, filed Dec. 19, 2017, in Opposition against EP2455473, 1 page.
Auxiliary request containing amended claims, filed Sep. 15, 2017, in Opposition against EP2455473, 1 page.
Auxiliary Request I, filed Apr. 26, 2018, during appeal of EP2455473, 1 page.
Balass et al., (1992). "Identification of a constitutive 45 kDa soluble protein associated with resistance to downy mildew in muskmelon (*Cucumis melo* L.), line PI 124111 F", Physiological and Molecular Plant Pathology, 41:387-396.
Belhaj et al., (2013). "Plant genome editing made easy: targeted mutagenesis in model and crop plants using the CRISPR/Cas system," Plant Methods, 9(39):1-10.
Bhattacharyya et al., (2005). "Identification of a Large Cluster of Coiled Coil-Nucleotide Binding Site—Leucine Rich Repeat-Type Genes from the Rps1 Region Containing Phytophthora Resistance Genes in Soybean", Theor. Appl. Genet., 111:75-86.
BLAST comparison between the amino acid sequences of Arabidopsis DMR6 (query ID Query_190785) and XP 013593012.1, dated Sep. 21, 2017, 2 pages.
BLAST comparison between the amino acid sequences of Arabidopsis DMR6 (query ID Query_236939) and XP 013620820.1, dated Sep. 21, 2017, 2 pages.
BLAST comparison results of query ID 258413, filed during prosecution of EP2455475, dated Aug. 30, 2016, 6 pages.
BLAST comparison results of query ID 3871 and subject ID 3873, filed during prosecution of EP2455474, dated Jul. 3, 2013, 2 pages.
BLAST comparison results of query ID XP_003526765.1 and subject ID OA094377.1, filed during prosecution of EP2455481, dated Aug. 30, 2016, 2 pages.
Blast query of the sequence of Fig. 4 against Spinacia oleracea, filed in Opposition against EP2455473, dated Sep. 4, 2018, 6 pages.
BLAST strategy and results on Solanum lycopersicum nucleotide sequence, filed Jul. 18, 2018, in Opposition against EP2455479, 2 pages.
BLAST strategy and results on Solanum lycopersicum protein sequence, filed Jul. 18, 2018, in Opposition against EP2455479, 5 pages.
BLAST-P query of AtF3H against A. thaliana genome, filed in Opposition against EP2455477, dated Dec. 7, 2017, 3 pages.
Bouchez et al., (1998). "Functional Genomics in Plants", Plant Physiology, 118:725-732.
Brandenberger et al., (1992). "Evaluation of Spinach Germplasm for Resistance to a New Race (Race 4) of *Peronospora farinosa* f. sp. spinaciae," HortScience, 27(20):1118-1119.
Brandenberger et al., (1994). "Characterization of resistance of spinach to white rust (Albugo occidentalis) and downy mildew (*Peronospora farinosa* f. sp. spinaciae)," Phytopathology, 84(4):431-437.
Brouwer et al., (2004). "Fine mapping of three quantitative trait loci for late blight resistance in tomato using near isogenic lines (NILs) and sub-NILs", Theoretical and Applied Genetics, 108:628-638.
Brouwer et al., (2004). "QTL analysis of quantitative resistance to Phytophthora infestans (late blight) in tomato and comparisons with potato", Genome, 27(3):475-492.
Budiman et al., (2000). "A Deep-Coverage Tomato BAC Library and Prospects toward Development of an STC Framework for Genome Sequencing", Genome Research, 10:129-136.
Burnham et al., (2003). "Quantitative Trait Loci for Partial Resistance to Phytophthora sojae in Soybean", Crop Science, 43(5):1610-1617.
Chen et al., (2008). "Host specificity and tomato-related race composition of Phytophthora infestans isolates in Taiwan during 2004 and 2005," Plant Disease, 92(5):751-755.
Cho et al., (2005). "Constitutive expression of the Flavanone 3-hydroxylase gene related to pathotype-specific Ascochyta blight resistance in *Cicer arietinum* L.", vol. 67, Physiological and Molecular Plant Pathology, pp. 100-107.

Choi et al., (2012). "Predicting the Functional Effect of Amino Acid Substitutions and Indels", PLoS ONE, 7(10):1-13.
Clough et al., (1998). "Floral Dip: A Simplified Method for Agrobacterium-Mediated Transformation of *Arabidopsis thaliana*", Plant Journal, 16(6):735-743.
Coelho et al., (2003). "Expression of resistance to downy mildew at cotyledon and adult plant stages in *Brassica oleracea* L.," Euphytica, 133:279-284.
Communication from the Examining Division dated Mar. 20, 2014, filed in Opposition against EP2455474, 1 page.
Communication from the Examining Division dated Mar. 20, 2014, filed in Opposition against EP2455479, 1 page.
Communication from the Examining Division for EP2455473 dated Mar. 20, 2014, filed in Appeal proceedings for EP2455473, 1 page.
Communication from the Examining Division for EP2455477 dated Nov. 14, 2013, filed in Opposition against EP2455477, 2 pages.
Communication from the Examining Division for EP2681234 dated Nov. 20, 2017, filed in Opposition against EP245577, 4 pages.
Communication from the Examining Division in case EP2455475 dated Mar. 20, 2014, concerning the staying of examination proceedings, 1 page.
Communication pursuant to Art. 94(3) EPC dated Mar. 8, 2017, filed Dec. 14, 2018 in Opposition against EP2455474, 3 pages.
Conrath et al., (2003). "Enhanced Resistance to Phytophthora Infestans and Alternaria Solani in Leaves and Tubers, Respectively, of Potato Plants with Decreased Activity of the Plastidic ATP/ADP Transporter", Planta, 19:75-83.
Constantinescu et al., (2002). "Peronospora-like Fungi (Chromista, Peronosporales) Parasitic on Brassicaceae and Related Hosts", Nova-Hedwigia, 74:291-338.
Cooke et al., (2000). "A molecular phylogeny of Phytophthora and related Oomycetes," Fungal Genetics and Biology, 30:17-32.
Crowe et al., (2003). "CATMA: a complete Arabidopsis GST database", Nucleic Acids Res., 31(1):156-158.
CV of Dr. A. Verhage, dated Oct. 20, 2017, submitted in opposition proceedings for EP2455473, 3 pages.
CV of Dr. T. Zeilmaker, filed Sep. 15, 2017, in Opposition against EP2455473, 2 pages.
Data on sequence and resistance of spinach variants, filed Feb. 14, 2017, in Opposition against EP2455473, 3 pages.
Database EMBL, (Apr. 15, 2002). "*Arabidopsis thaliana* Flavanone 3-Hydroxylase-like Protein (At5g24530) mRNA, complete Cds", Retrieved from EBI Accession No. EMBL: AY081455. 2 pages.
Database EMBL, (Jun. 16, 2001). "*Arabidopsis thaliana* Flavanone 3-Hydroxylase-like Protein {K 18P6.6) mRNA, Complete Cds", Retrieved from EBI Accession No. EMBL: AF386975. 2 pages.
Database EMBL, retrieved from EBI Accession No. EMBL: DQ208192, Database Accession No. DQ208192, 2 pages.
Database EMBL, XP002386701, retrieved from EBI accession No. EM_PRO:AF082525, Database Accession No. AF082525, 2 pages.
De Jong et al., (2006). "Membrane-associated transcripts in *Arabidopsis*; their isolation and characterization by DNA microarray analysis and bioinformatics", Plant J., 46(4):708-721.
De las Mercedes Dana et al., (2006). "Transgenic Tobacco Plants Overexpressing Chitinases of Fungal Origin Show Enhanced Resistance to Biotic and Abiotic Stress Agents", Plant Physiol., vol. 142, No. 2, American Society of Plant Biologists, pp. 722-730.
De Wit, P.J.G.M. (1992). "Molecular characterization of gene-for-gene systems in plant-fungus interactions and the application of avirulence genes in control of plant pathogens", Annu. Rev. Phytopathol., 30:391-418.
Decision T 1063/18, filed on Apr. 29, 2019 in Opposition proceedings against EP2455475, 29 pages.
Declaration and CV of Dr. A. Rijpkema, dated Jul. 27, 2018, submitted in opposition proceedings for EP2455474, 4 pages.
Declaration and CV of Dr. B. D'hoop, dated Jul. 27, 2018, submitted in opposition proceedings for EP2455474, 3 pages.
Declaration and CV of Dr. P.M. Eggink, dated Jul. 14, 2018, submitted in opposition proceedings for EP2455479, 3 pages.
Declaration by Dr. A. Verhage, dated Jun. 26, 2017, submitted in opposition proceedings for EP2455474 and EP2455479, 1 page.
Declaration of Dr. A. Verhage, dated Oct. 17, 2017, submitted in opposition proceedings for EP2455473, 2 pages.

(56) References Cited

OTHER PUBLICATIONS

Develey-Riviere et al., (2007). "Resistance to pathogens and host developmental stage: a multifaceted relationship within the plant kingdom," New Phytologist, 175:405-416.
Disease test results DMR6 Spinach mutants, filed Jul. 17, 2017, in Opposition against EP2455473, 1 page.
Elliott, Charlotte (1992). "Relative Susceptibility to Pythium Root Rot of Twelve Dent Corn Inbreds", Journal of Agricultural Research, 64(12):711-723.
Enza lettuce catalogue, dated Jan. 17, 2014, filed in Opposition to EP2115147, p. 102-115.
Experimental data "Annex A—Overview supporting data DMR6 down regulation and disease resistance," filed Oct. 10, 2016 by the Applicant during the examination of EP2455474 (six page excerpt filed Jul. 18, 2018 in Opposition against EP2455479), 28 pages.
Experimental data on mutation in dmr6 conferring resistance to cabbage, filed during Opposition against EP2455477, dated Jan. 18, 2018, 3 pages.
Experimental data showing no Phytophthora resistance, filed during prosecution of EP3167051, dated Aug. 17, 2017, 1 page.
Experimental data showing that the claimed sunflower plants are resistant to downy mildew, filed during prosecution of EP3024929, dated Dec. 21, 2017, 2 pages.
Fall et al., (2015). "Infection Efficiency of Four Phytophthora infestans Clonal Lineages and DNA-based Quantification of Sporangia," PLoS ONE, 10(8): e0136312doi: 10.1371/journal.pone.0136312, 18 pages.
Ferreyra et al., (2015). "The Identification of Maize and *Arabidopsis* Type I Flavone Synthases Links Flavones with Hormones and Biotic Interactions," Plant Physiology, 169:1090-1107.
Fischer et al., (Feb. 2004). "Quantitative Trait Locus Analysis of Fungal Disease Resistance Factors on a Molecular Map of Grapevine", Theoretical and Applied Genetics, 108(3):501-515.
Flanagan et al., (2010). "Using SIFT and PolyPhen to predict loss-of-function and gain-of-function mutations", Genetic Testing and Molecular Biomarkers, 14(4):533-537.
Franchel et al., (2013). "Positional cloning of a candidate gene for resistance to the sunflower downy mildew, Plasmopara halstedii race 300", Theoretical and Applied Genetics, 126(2):359-367.
Friedrich et al., (2001). "NIM1 Overexpression in *Arabidopsis* Potentiates Plant Disease Resistance and Results in Enhanced Effectiveness of Fungicides", MPMI, 14(9):1114-1124.
Further experimental data of pathogen resistance against Phytophthora infestans of mutated tomato plants, filed during Opposition against EP2455479, dated Jan. 4, 2019, 2 pages.
Gaspero et al., (2002). "Resistance Gene Analogs are Candidate Markers for Disease-Resistance Genes in Grape (*Vitis* spp.)", Theoretical and Applied Genetics, 106(1):163-172.
Geneseq Database Accession No. AAG45151, Oct. 18, 2000, 4 pages.
Giovanini et al., (2006). "Gene-for-gene defense of wheat against the Hessian fly lacks a classical oxidative burst", Molecular Plant-Microbe Interactions, 19(9):1023-1033.
Göker et al., (2003). "Taxonomic aspects of Peronosporaceae inferred from Bayesian molecular phylogenetics", Canadian Journal of Botany, 81(7):672-683.
Göker et al., (2004). "Phylogeny of Hyaloperonospora based on nuclear ribosomal internal transcribed spacer sequences", Mycological Progress, 3(2):83-94.
Grimplet et al., (2007). "Tissue-Specific mRNA Expression Profiling in Grape Berry Tissues", BMC Genomics, 8(187):1-23.
Gurr et al., (2005). "Engineering plants with increased disease resistance: how are we going to express it?" Trends Biotechnol., 23(6):283-290.
Gurr et al., (2005). "Engineering plants with increased disease resistance: what are we going to express?" Trends Biotechnology, 23(6):275-282.
Guzzo, Silvia Dias (2004). "Isolation of cv. Mundo Novo coffee plant genes associated with systemic acquired resistance", 21 pages (including 10 pages of English translation).

Hellens et al., (2000). "pGreen: A Versatile and Flexible Binary Ti vector for Agrobacterium-Mediated Plant Transformation", Plant Molecular Biology, 42:819-832.
Henikoff et al., (2004). "TILLING. Traditional Mutagenesis Meets Functional Genomics", Plant Physiology, 135:630-636.
Holub et al., (1994). "Phenotypic and Genotypic Characterization of Interactions Between Isolates of Peronospora parasitica and Accessions of *Arabidopsis thaliana*", 7(2):223-239.
Hong et al., (2008). "First confirmed report of downy mildew caused by Hyaloperonospora parasitica on broccoli in Korea", Plant Pathology, 57(4):777.
Instructions to the PhD candidate, filed Jul. 17, 2017, in Opposition against EP2455473, Utrecht University, 11 pages.
International Seed Federation Guidelines for Coding Pests of Vegetable and Cereal Crops, submitted in Opposition against EP2455477, dated Jan. 18, 2018, 4 pages.
Irish et al., (2007). "Three new races of the spinach downy mildew pathogen identified by a modified set of spinach differentials," Plant Disease, 91(11):1392-1396.
Karimi et al., (2002). "GATEWAY Vectors for Agrobacterium-Mediated Plant Transformation", TRENDS in Plant Science, 7(5):193-195.
Kim et al., (2006). "Characterization of Late Blight Resistance Derived from Solanum pimpinellifolium L3708 against Multiple Isolates of the Pathogen Phytophthora infestans", Journal of the American Society for Horticultural Science, 131(5):637-645.
Kitz, Leilani, (2008). "Evaluation of Downy Mildew (*Peronospora farinosa* f. sp. chenopodii) Resistance among Quinoa Genotypes and Investigation of P. farinosa Growth using Scanning Electron Microscopy", All Theses and Dissertations, Brigham Young University, 89 pages.
Kofoet et al., (1990). "Inheritance of Resistance to Downy Mildew (Peronospora Destructor [Berk.] Casp.) from Allium Roylei Steam in the Backcross Allium Cepa L. x (A. Roylei ×A. Cepa)", Plant Breeding, 105(2):144-149.
Kofoet et al., (1990). "Resistance to Downy Mildew (Peronospora Destructor (Berk.) Casp.) in Allium Species//Resistenz Gegen Falschen Mehltau (Peronospora Destructor (Berk.) Casp.) in Allium-Arten," Zeitschrift fuer Pflanzenkrankheiten und Pflanzenschutz//Journal of Plant Diseases and Protection, 97(1):13-23.
Kortekamp et al., (2006). "Expression Analysis of Defence-Related Genes in Grapevine Leaves after Inoculation with a Host and a Non-Host Pathogen", Plant Physiology and Biochemistry, 44(1):58-67.
Ku et al., (2000). "Comparing Sequenced Segments of the Tomato and *Arabidopsis* Genomes Large-Scale Duplication Followed by Selective Gene Loss Creates a Network of Synteny", PNAS, 97(16):9121-9126.
Lacomme et al., (1999). "Bax-induced cell death in tobacco is similar to the hypersensitive response", Proc. Natl. Acad. Sci. 96(14):7956-7961.
Lamour et al., (2009). "Oomycete Genetics and Genomics: Diversity, Interactions and Research Tools", Wiley-Blackwell, 6 pages.
Lebeda, Ales, (1992). "Screening of wild cucumis species against downy mildew (Pseudoperonospora cubensis) isolates from cucumbers", Phytoparasitica, 20(3):203-210.
Lee et al., (1999). "Identification of the Gene Encoding Homoserine Kinase from *Arabidopsis thaliana* and Characterization of the Recombinant Enzyme derived from the Gene", Arch. Biochem. Biophys., 372(1):135-142.
Lee et al., (2005). "Methionine and Threonine Synthesis are Limited by Homoserine availability and not the Activity of Homoserine Kinase in *Arabidopsis thaliana*", The Plant Journal, 41:685-696.
Letter accompanying subsequently filed items, filed during prosecution of EP2455473, dated Mar. 10, 2014, 1 page.
Letter accompanying subsequently filed items, filed during prosecution of EP2455474, dated Mar. 10, 2014, 1 page.
Letter accompanying subsequently filed items, filed during prosecution of EP2455475, dated Mar. 10, 2014, 1 page.
Letter accompanying subsequently filed items, filed during prosecution of EP2455476, dated Mar. 10, 2014, 1 page.
Letter accompanying subsequently filed items, filed during prosecution of EP2455477, dated Mar. 10, 2014, 1 page.

(56) References Cited

OTHER PUBLICATIONS

Letter accompanying subsequently filed items, filed during prosecution of EP2455481, dated Mar. 10, 2014, 1 page.
Letter accompanying subsequently filed items, filed during prosecution of EP2455482, dated Mar. 10, 2014, 1 page.
Letter regarding the opposition procedure (no time limit) and Auxiliary requests I and II, filed during Opposition against EP2455477, dated Dec. 8, 2017, 22 pages.
Letter regarding the opposition procedure (no time limit), filed during Opposition against EP2455473, dated Sep. 14, 2017, 3 pages.
Letter regarding the opposition procedure (no time limit), filed during Opposition against EP2455473, dated Sep. 15, 2017, 17 pages.
Letter regarding the opposition procedure (no time limit), filed during Opposition against EP2455477, dated Jan. 18, 2018, 15 pages.
Letter regarding the opposition procedure and Auxiliary requests I and II, filed during Opposition against EP2455474, dated Dec. 14, 2018, 39 pages.
Letter regarding the opposition procedure and Auxiliary requests I and II, filed during Opposition against EP2455479, dated Jan. 8, 2019, 48 pages.
Lukacin et al., (1997). "Identification of strictly conserved histidine and arginine residues as part of the active site in Petunia hybrida flavanone 3β-hydroxylase," Eur. J. Biochem., 249:748-757.
Mae et al., (2001). "Transgenic Plants Producing the Bacterial Pheromone N-Acyl-Homoserine Lactone Exhibit Enhanced Resistance to the Bacterial Phytopathogen Erwinia Carotovora", Molecular Plant-Microbe Interactions, 14(9):1035-1042.
McCallum et al., (2000). "Targeted Screening for Induced Mutations", Nature Biotechnology, 18:455-457.
Meer et al., (1990). "An Interspecific Cross between Allium Roylei Steam and *Allium cepa* L, and its Backcross to A. Cepa", Euphytica, 47:29-31.
Mosher et al., (2006). "A Comprehensive Structure-Function Analysis of *Arabidopsis* SNI1 Defines Essential Regions and Transcriptional Repressor Activity", The Plant Cell, 18:1750-1765.
MRNA sequence ID XM_008464687.2 corresponding to melon DMR6 protein sequence ID XP_008462909.2, filed on Apr. 29, 2019 in Opposition proceedings against EP2455475, 2 pages.
Multiple alignment of cabbage DMR6 (*B. oleracea*) with known oxidoreductases, filed May 22, 2017, in Opposition against EP2455477, 2 pages.
Multiple alignment of spinach DMR6 (*S. oleracea*) with known oxidoreductases, filed Feb. 14, 2017, in Opposition against EP2455473, 1 page.
NCBI Reference Sequence NP_190692.1, dated Jul. 3, 2013, filed in Opposition against EP2455473 and during prosecution for EP2455474 and EP2455479, 1 page.
NCBI Reference Sequence NP_197841.1, dated Nov. 25, 2016, filed in Opposition against EP2455473 and during prosecution for EP2455474 and EP2455479, 2 pages.
Notice of appeal by Bird&Bird, filed in relation to EP2455473, dated Feb. 22, 2018, 2 pages.
Notice of appeal by Bird&Bird, filed in relation to EP2455477, dated Jul. 19, 2018, 2 pages.
Nowicki et al., (2012). "Potato and Tomato late blight caused by Phytophthora infestans: An overview of pathology and resistance breeding," Plant Disease, 96(1):4-17.
Official variety description spinach variety Bandola by the Naktuinbouw (1995), filed in Opposition against EP2455473, 1 page.
Official variety description spinach variety Maracas by the Naktuinbouw (1950), filed in Opposition against EP2455473, 1 page.
Official variety description spinach variety Marimba by the Naktuinbouw (1950), filed in Opposition against EP2455473, 1 page.
Official variety description spinach variety Symphony by the Naktuinbouw (1950), filed in Opposition against EP2455473, 3 pages.
Pacific Pests and Pathogens Fact Sheet on cabbage downy mildew, dated Sep. 20, 2017, 3 pages.
Parker et al., (1996). "Characterization of eds1, a mutation in *Arabidopsis* suppressing resistance to Peronospora parasitica specified by several different RPP genes", Plant Cell, American Society of Plant Physiologists, 8(11):2033-2046.
Partial set of drawings filed in response to formal objections, filed during prosecution of EP2455474, dated Mar. 13, 2012, 4 pages.
Partial set of drawings filed in response to formal objections, filed during prosecution of EP2455475, dated Mar. 13, 2012, 4 pages.
Partial set of drawings filed in response to formal objections, filed during prosecution of EP2455476, dated Mar. 13, 2012, 4 pages.
Partial set of drawings filed in response to formal objections, filed during prosecution of EP2455477, dated Mar. 13, 2012, 4 pages.
Partial set of drawings filed in response to formal objections, filed during prosecution of EP2455478, dated Mar. 13, 2012, 4 pages.
Partial set of drawings filed in response to formal objections, filed during prosecution of EP2455479, dated Mar. 13, 2012, 4 pages.
Partial set of drawings filed in response to formal objections, filed during prosecution of EP2455480, dated Mar. 13, 2012, 4 pages.
Partial set of drawings filed in response to formal objections, filed during prosecution of EP2455481, dated Mar. 13, 2012, 4 pages.
Partial set of drawings filed in response to formal objections, filed during prosecution of EP2455482, dated Mar. 13, 2012, 4 pages.
Partial set of drawings filed in response to formal objections, filed during prosecution of EP2455483, dated Mar. 13, 2012, 4 pages.
Perchepied et al., (2005). "Relationship Between Loci Conferring Downy Mildew and Powdery Mildew Resistance in Melon Assessed by Quantitative Trait Loci Mapping", Phytopathology, 95(5):556-565.
Pihlajamaa, Heli, Presentation slides taken from conference documentation, Presentation at the 8th conference on Intellectual Property Protection for Plant Innovation 2017, p. 197-205.
Preliminary Amendment, filed for U.S. Appl. No. 15/975,670, dated Jul. 23, 2018, 5 pages.
Preliminary Amendment, filed for U.S. Appl. No. 16/055,697, dated Aug. 6, 2018, 9 pages.
Primrose et al., (2006). "Principles of Gene Manipulation and Genomics," Chapter 9 of Bioinformatics, Blackwell Publishing, 21 pages.
Protocol for Distinctness, Uniformity and Stability Tests for *Spinacea oleracea* L. (2002). European Union Community Plant Variety Office, Final CPVO-TP-55-6 Final, 17 pages.
Radwan et al., (2011). "Molecular Characterization of Two Types of Resistance in Sunflower to Plasmopara halstedii, the Causal Agent of Downy Mildew", The American Phytopathological Society, 101(8):970-979.
Reply of the patent proprietor to the notice(s) of opposition dated Apr. 29, 2019, filed in Opposition against EP2455475, 38 pages.
Reply of the patent proprietor to the notice(s) of opposition dated Feb. 13, 2017, filed during Opposition against EP2455473, 28 pages.
Reply of the patent proprietor to the notice(s) of opposition dated Jul. 11, 2014, filed during Opposition against EP2115147, 5 pages.
Reply of the patent proprietor to the notice(s) of opposition dated May 22, 2017, filed during Opposition against EP2455477, 30 pages.
Reply to appeal by Bird&Bird filed in relation to EP2455473, dated Sep. 10, 2018, 40 pages.
Reply to communication from the Examining Division, filed during prosecution of EP2115147, dated Aug. 20, 2010, 4 pages.
Reply to communication from the Examining Division, filed during prosecution of EP2115147, dated Feb. 2, 2012, 3 pages.
Reply to communication from the Examining Division, filed during prosecution of EP2115147, dated Jun. 5, 2012, 1 page.
Reply to communication from the Examining Division, filed during prosecution of EP2115147, dated May 26, 2011, 3 pages.
Reply to communication from the Examining Division, filed during prosecution of EP2455473, dated Jul. 4, 2013, 4 pages.
Reply to communication from the Examining Division, filed during prosecution of EP2455473, dated Oct. 21, 2013, 1 page.
Reply to communication from the Examining Division, filed during prosecution of EP2455474, dated Dec. 8, 2015, 7 pages.

(56) References Cited

OTHER PUBLICATIONS

Reply to communication from the Examining Division, filed during prosecution of EP2455474, dated Jul. 4, 2013, 4 pages.
Reply to communication from the Examining Division, filed during prosecution of EP2455474, dated Mar. 17, 2017, 2 pages.
Reply to communication from the Examining Division, filed during prosecution of EP2455475, dated Jul. 5, 2013, 4 pages.
Reply to communication from the Examining Division, filed during prosecution of EP2455476, dated Dec. 3, 2015, 7 pages.
Reply to communication from the Examining Division, filed during prosecution of EP2455476, dated Jul. 5, 2013, 4 pages.
Reply to communication from the Examining Division, filed during prosecution of EP2455477, dated Jul. 5, 2013, 4 pages.
Reply to communication from the Examining Division, filed during prosecution of EP2455477, dated Oct. 21, 2013, 1 page.
Reply to communication from the Examining Division, filed during prosecution of EP2455478, dated Dec. 11, 2015, 7 pages.
Reply to communication from the Examining Division, filed during prosecution of EP2455478, dated Jul. 5, 2013, 4 pages.
Reply to communication from the Examining Division, filed during prosecution of EP2455479, dated Dec. 8, 2015, 7 pages.
Reply to communication from the Examining Division, filed during prosecution of EP2455479, dated Jul. 5, 2013, 4 pages.
Reply to communication from the Examining Division, filed during prosecution of EP2455480, dated Dec. 3, 2015, 7 pages.
Reply to communication from the Examining Division, filed during prosecution of EP2455480, dated Jul. 8, 2013, 5 pages.
Reply to communication from the Examining Division, filed during prosecution of EP2455481, dated Dec. 3, 2015, 7 pages.
Reply to communication from the Examining Division, filed during prosecution of EP2455482, dated Jul. 8, 2013, 5 pages.
Reply to communication from the Examining Division, filed during prosecution of EP2455483, dated Jul. 8, 2013, 5 pages.
Reply to communication from the Examining Division, filed during prosecution of EP3024929, dated Oct. 15, 2018, 2 pages.
Reply to communication from the Examining Division, filed during prosecution of EP3094722, dated Jan. 17, 2018, 2 pages.
Reply to communication from the Examining Division, filed during prosecution of EP3094722, dated May 28, 2018, 1 page.
Reply to communication from the Examining Division, filed during prosecution of EP3167051, dated Apr. 17, 2018, 2 pages.
Reply to communication from the Examining Division, filed during prosecution of EP3167051, dated May 28, 2018, 1 page.
Reply to the invitation to remedy deficiencies, filed during prosecution of EP2115147, dated Jan. 27, 2010, 2 pages.
Reply to Written Opinion prepared by the EPO, filed during prosecution of EP2455473, dated Nov. 14, 2012, 3 pages.
Reply to Written Opinion prepared by the EPO, filed during prosecution of EP2455474, dated Nov. 14, 2012, 3 pages.
Reply to Written Opinion prepared by the EPO, filed during prosecution of EP2455475, dated Nov. 14, 2012, 3 pages.
Reply to Written Opinion prepared by the EPO, filed during prosecution of EP2455476, dated Nov. 14, 2012, 3 pages.
Reply to Written Opinion prepared by the EPO, filed during prosecution of EP2455477, dated Nov. 19, 2012, 3 pages.
Reply to Written Opinion prepared by the EPO, filed during prosecution of EP2455478, dated Nov. 19, 2012, 3 pages.
Reply to Written Opinion prepared by the EPO, filed during prosecution of EP2455480, dated Nov. 19, 2012, 3 pages.
Reply to Written Opinion prepared by the EPO, filed during prosecution of EP2455481, dated Nov. 19, 2012, 3 pages.
Request for further processing, filed during prosecution of EP3024929, dated Dec. 21, 2017, 2 pages.
Request for interpreters during oral proceedings, dated Sep. 14, 2017, filed during Opposition against EP2455473, 5 pages.
Response to Non-Final Office Action, filed for U.S. Appl. No. 15/594,293, dated Feb. 28, 2019, 11 pages.
Rijk Zwaan General Information Website, dated Jul. 11, 2014, filed in Opposition proceedings against EP2115147, Available Online at <http://www.rijkzwaan.com/wps/wcm/connect/RZ+Corporate/Rijk+Zwaan/Company/About+us/General+Information>, 1 page.
Rostas et al., (2013). "Copper and Herbivory Lead to Priming and Synergism in Phytohormones and Plant Volatiles in the Absence of Salicylate-Jasmonate Antagonism", Plant Signaling & Behavior, 8(6): e24264-1-e24264-3.
Rothrock et al., (2006). "Identification of Pythium-Resistant Cold-Tolerant Rice Germplasm through Controlled Environmental and Field Evaluations," Proceedings of the Thirty-First Rice Technical Working Group, Retrieved from the Internet http://www.uaex.edu/rtwg/Proceedings/2006/RTWG%20Proc%202006.pdf, [retrieved on Apr. 24, 2012], pp. 108-109.
Russell, G. E., (1966). "Some effects of inoculation with yellowing viruses on the susceptibility of sugar beet to fungal pathogens: I. Susceptibility to Peronospora farinosa", Transactions of the British Mycological Society, 49(4):611-619.
Sabetta et al., (2011). "sunTILL: a TILLING resource for gene function analysis in sunflower", Plant Methods 2011, 7(20):1-13.
Sandhu et al., (2005). "Soybean Phytophthora Resistance Gene Rps8 Maps Closely to the Rps3 Region", Journal of Heredity, 96(5): 536-541.
Schlegel, Rolf H.J. (2003). Encyclopedic dictionary of plant breeding and related subjects, Haworth Press Inc., Binghamton, New York, p. 234-237.
Sequence alignment of Spinacia oleracea DMR6 gene (SEQ ID 80) and DMR6 protein (SEQ ID 81) from EP2455473 with an alternative Spinacia oleracea DMR6 gene and DMR6 protein as identified in *Spinacia oleracea* L. accession SPI 173 (IPK, Gatersleben, Germany) and a number of spinach varieties, filed Aug. 24, 2016, in Opposition against EP2455473, 2 pages.
Sim et al., (2012). "SIFT web server: predicting effects of amino acid substitutions on proteins", Nucleic Acids Res., 40, Web Server issue, 6 pages.
Sinapidou et al., (2004). "Two TIR:NB:LRR Genes are Required to Specify Resistance to Peronospora Parasitica Isolate Cala2 in *Arabidopsis*", The Plant Journal, 38(6):898-909.
Skadhauge et al., (1997). "The role of the barley testa layer and its flavonoid content in resistance to Fusarium infections", Carlsberg Laboratory, Department of Physiology, 126:147-160.
Smart et al., "Best Control of Downy Mildew in Cole Crops", Dept. of Plant Pathology and Plant-Microbe Biology, Cornell University, Geneva NY, filed Dec. 8, 2017, in Opposition against EP2455477, 2 pages.
Solanum tuberosum naringenin, 2-oxoglutarate 3-dioxygenase-like (LOC102590513), mRNA, Dec. 12, 2013, cited in Chinese Application No. 2014800731630 Office Action dated Feb. 19, 2019, 2 pages.
Solanum tuberosum naringenin, 2-oxoglutarate 3-dioxygenase-like (LOC102604390), mRNA, Dec. 12, 2013, cited in Chinese Application No. 2014800731630 Office Action dated Feb. 19, 2019, 2 pages.
Somssich et al., (2003). "Closing another gap in the plant SAR puzzle," Cell, 113(7):815-816.
Statement of grounds of appeal by Bird&Bird, filed in relation to EP2455473, dated Apr. 26, 2018, 10 pages.
Summary of the legal entity "Rijk Zwaan Zaadteelt en Zaadhandel B.V." obtained from the Dutch Chamber of Commerce, filed Jul. 11, 2014, in Opposition against EP2115147, 4 pages.
Summons to attend Oral Proceedings for case EP2455475, dated Mar. 22, 2016, in order to discuss outstanding objections under Articles 56 and 83 EPC, 7 pages.
Summons to attend Oral Proceedings pursuant to Rule 115(1) EPC, filed in Opposition against EP2455474, dated Jul. 13, 2016, 1 page.
Summons to attend Oral Proceedings pursuant to Rule 115(1) EPC, filed in Opposition against EP2455479, dated May 31, 2016, 5 pages.
Sun et al., (2016). "Silencing of Six Susceptibility Genes Results in Potato Late Blight Resistance", Transgenic Research, 25: 731-742 (with 12 pages of Supplementary Copy).
Szwacka et al., (2002). "Variable properties of transgenic cucumber plants containing the thaumatin II gene from Thaumatococcus daniellii", Acta Physiologiae Plantarum, 24(2):173-185.

(56) References Cited

OTHER PUBLICATIONS

Table 1: Spinach DMR6 mutants presented in O18, filed in Opposition against EP2455473, dated Oct. 20, 2017, 1 page.
Table on insufficiency of disclosure issues, filed Jul. 18, 2018, in Opposition against EP2455479, 3 pages.
Table on insufficiency of disclosure issues, filed Jul. 30, 2018, in Opposition against EP2455474, 3 pages.
Table on insufficiency of disclosure issues, filed Oct. 1, 2018, in Opposition against EP2455475, 3 pages.
Table with all insufficiency of disclosure issues, filed Apr. 26, 2018, in Appeal against EP2455473, 3 pages.
Takatsuji, Hiroshi, (2014). "Development of Disease-Resistant Rice Using Regulatory Components of Induced Disease Resistance", Frontiers in Plant Science, 5(630):12 pages.
Third Party Observations, filed in Opposition against EP 2455474, dated Feb. 9, 2017 for EP Application No. 12155887, 2 pages.
Thomas et al., (1992). "Resistance to Race 2 of Peronospora parasitica in U.S. Plant Introductions of *Brassica oleracea* var. capitata," HortScience, 27(10):1120-1122.
Thomas et al., (2000). "Linkage of random amplified polymorphic DNA markers to downy mildew resistance in cucumber (*Cucumis sativus* L.)", Euphytica, 115(2):105-113.
Thomazella et al., (2016). "CRISPR-Cas9 Mediated Mutagenesis of a DMR6 Ortholog in Tomato Confers Broad-Spectrum Disease Resistance", bioRxiv doi: 10.1101/064824, pp. 1-23.
Till et al., (2004). "Mismatch cleavage by single-strand specific nucleases", Nucleic Acids Research, 32(8):2632-2641.
Tor et al., (2004). "*Arabidopsis* Downy Mildew Resistance Gene RPP27 Encodes a Receptor-Like Protein Similar to CLAVATA2 and Tomato Cf-9 1", Plant Physiology, 135:1100-1112.
TWV/40/11, "Report of the Technical Working Party for Vegetables," Jun. 16, 2006, UPOV, 40th session, Mexico, 57 pages.
UniProt, XP002730065, retrieved from EBI Accession No. UNIPROT:M0ZIQ1 Database Accession No. MOZIQ1 Sequence, 2 pages.
Uniprot, XP002730066, retrieved from EBI Accession No. UNIPROT:M1CK41 Database Accession No. M1CK41 Sequence, 2 pages.
UniProt, XP002730067, retrieved from EBI Accession No. UNIPROT:K4C928, Database Accession No. K4C928 sequence, 2 pages.
Vailleau et al., (2002). "A R2R3-MYB gene, AtMYB30, acts as a positive regulator of the hypersensitive cell death program in plants in response to pathogen attack", PNAS, 99(15):10179-10184.
Van Damme et al., (2005). "Identification of *Arabidopsis* Loci Required for Susceptibility to the Downy Mildew Pathogen Hyaloperonospora parasitica", Molecular Plant-Microbe Interactions, 18(6):583-592.
Van Damme et al., (2008). "*Arabidopsis* DMR6 encodes a putative 2OG-Fe(II) oxygenase that is defense-associated but required for susceptibility to downy mildew", The Plant Journal, 54:785-793.
Van Damme et al., (2009). "Downy Mildew Resistance in *Arabidopsis* by Mutation of Homoserine Kinase", The Plant Cell, 21:2179-2189.
Van Damme, Mireille, (2007). "Genetic analysis of disease susceptibility in the *Arabidopsis*-Hyaloperonospora parasitica interaction," Thesis, 134 pages.
Vandenbussche et al., (2008). "Generation of a 3D Indexed Petunia Insertion Database for Reverse Genetics", The Plant Journal, 54(6):1105-14.
Vicente et al., (2013). "Xanthomonas campestris pv. campestris (cause of black rot of crucifers) in the genomic era is still a worldwide threat to *Brassica* crops," Molecular Plant Pathology, 14(1):2-18.
Vogel et al., (2002). "PMR6, a Pectate Lyase-Like Gene Required for Powdery Mildew Susceptibility in *Arabidopsis*", The Plant Cell, 14:2095-2106.
Vogel et al., (2013). "Insights into the regulation of protein abundance from proteomic and transcriptomic analyses," Nat. Rev. Genet., 13(4):227-232.

Voglmayr, Hermann, (2003). "Phylogenetic relationships of Peronospora and related genera based on nuclear ribosomal ITS sequences", Mycol. Res., 107(10):1132-1142.
Weaver et al., (2006). "The *Arabidopsis thaliana* TIR-NB-LRR R-protein, RPP1A; protein localization and constitutive activation of defence by truncated alleles in tobacco and *Arabidopsis*," The Plant Journal, 47:829-840.
Wikipedia, "Expressed sequence tag", website as of Dec. 11, 2018, available online at <https://en.wikipedia.org/wiki/Expressed_sequence_tag>, filed during opposition of EP2455479, 4 pages.
Wikipedia, "Gene silencing", website as of Jul. 10, 2018, available online at <https://en.wikipedia.org/wiki/Gene_silencing>, filed during opposition of EP2455479, 12 pages.
Wikipedia, "Hyaloperonospora Brassicae", website as of Sep. 20, 2017, available online at <https://en.wikipedia.org/wiki/Hyaloperonospora_brassicae>, filed during opposition of EP2455477, 2 pages.
Wikipedia, "Hyaloperonospora Parasitica", website as of Sep. 20, 2017, available online at <https://en.wikipedia.org/wiki/Hyaloperonospora_parasitica>, filed during opposition of EP2455477, 3 pages.
Wilmouth et al., (2002). "Structure and Mechanism of Anthocyanidin Synthase from *Arabidopsis thaliana*," Structure, 10:93-103.
Withdrawal of a request for oral proceedings, filed during prosecution of EP2455482, dated Jan. 8, 2016, 1 page.
Withdrawal of a request for oral proceedings, filed during prosecution of EP2455483, dated Jan. 8, 2016, 1 page.
Withdrawal of an appeal, filed during appeal of EP2455477, dated Sep. 20, 2018, 1 page.
Written submission in preparation to/during oral proceedings, filed during prosecution of EP2455474, dated Oct. 10, 2016, 2 pages.
Written submission in preparation to/during oral proceedings, filed during prosecution of EP2455475, dated Aug. 30, 2016, 3 pages.
Written submission in preparation to/during oral proceedings, filed during prosecution of EP2455476, dated Jul. 21, 2016, 4 pages.
Written submission in preparation to/during oral proceedings, filed during prosecution of EP2455478, dated Oct. 10, 2016, 2 pages.
Written submission in preparation to/during oral proceedings, filed during prosecution of EP2455479, dated Oct. 5, 2016, 4 pages.
Written submission in preparation to/during oral proceedings, filed during prosecution of EP2455480, dated Jul. 21, 2016, 4 pages.
Written submission in preparation to/during oral proceedings, filed during prosecution of EP2455481, dated Aug. 30, 2016, 3 pages.
Written submission in preparation to/during oral proceedings, filed during prosecution of EP2455482, dated Oct. 13, 2015, 8 pages.
Written submission in preparation to/during oral proceedings, filed during prosecution of EP2455483, dated Oct. 13, 2015, 8 pages.
Xu et al., (2011). "Genome Sequence and Analysis of the Tuber Crop Potato", Nature, 475:189-195.
Yang et al., (2005). "Characterization and Mapping of Rpi1, A Gene that Confers Dominant Resistance to Stalk Rot in Maize", Molecular Genetics and Genomics, 274(3):229-234.
Zeilmaker et al., (2015). "Downy Mildew Resistant 6 and DMR6-Like Oxygenase 1 are Partially Redundant but Distinct Suppressors of Immunity in *Arabidopsis*", The Plant Journal, 81(2):210-222.
Zeilmaker, Tieme, (2012). Functional and Applied Aspects of the Downy Mildew Resistant 1 and 6 Genes in *Arabidopsis*, Universiteit Utrecht, Available at <http://web.science.uu.nl/pmi/publications/PDF/2012/Proefschrift-Zeilmaker-2012.pdf>, 147 pages.
Zhang et al., (2017). "S5H/DMR6 Encodes a Salicylic Acid 5-Hydroxylase that Fine-Tunes Salicylic Acid Homeostasis," Plant Physiology Preview, DOI:10.1104/pp.17.00695, 41 pages.
Zhang et al., (2013). "Salicylic Acid 3-Hydroxylase Regulates *Arabidopsis* Leaf Longevity by Mediating Salicylic Acid Catabolism", Proceedings of The National Academy of Sciences of the United States of America, 110(36):1-6.
Zhang, James Z. (2003). "Overexpression analysis of plant transcription factors", Curr. Opin. Plant Biol., 6(5):430-440.
Zimmermann et al., (2005). "Gene-expression analysis and network discovery using Genevestigator", Trends Plant Sci., 10(9):407-409.
Communication from the Examining Division in case EP3024929 dated Jul. 9, 2019, concerning the staying of examination proceedings, 3 pages.

(56) References Cited

OTHER PUBLICATIONS

Communication from the Examining Division in case EP3094722 dated Jun. 27, 2019, concerning the staying of examination proceedings, 3 pages.
Communication from the Examining Division in case EP3167051 dated Jun. 27, 2019, concerning the staying of examination proceedings, 3 pages.
Communication from the Opposition Division in case EP2455474 dated Jan. 3, 2020, concerning the staying of opposition proceedings, 5 pages.
Communication from the Opposition Division in case EP2455474 dated Jun. 27, 2019, concerning the staying of opposition proceedings, 2 pages.
Communication from the Opposition Division in case EP2455475 dated Jan. 10, 2020, concerning the staying of opposition proceedings, 5 pages.
Communication from the Opposition Division in case EP2455475 dated Jun. 27, 2019, concerning the staying of opposition proceedings, 2 pages.
Communication from the Opposition Division in case EP2455479 dated Jan. 13, 2020, concerning the staying of opposition proceedings, 5 pages.
Communication from the Opposition Division in case EP2455479 dated Jun. 28, 2019, concerning the staying of opposition proceedings, 4 pages.
Communication from the Proprietor in case EP2455474 dated Nov. 11, 2019, concerning the staying of opposition proceedings, 4 pages.
Communication from the Proprietor in case EP2455475 dated Nov. 11, 2019, concerning the staying of opposition proceedings, 4 pages.
Communication from the Proprietor in case EP2455479 dated Nov. 8, 2019, concerning the staying of opposition proceedings, 3 pages.
Database EMBL, (Dec. 18, 2014). "Glycine soja Flavanone 3-dioxygenase", XP002785532, Retrieved from EBI Accession No. EMBL: KHN19568, Database accession No. KHN19568, 2 pages.
Database UniProt, (Jun. 13, 2012). "Glycine max (Soybean); belongs to the iron/ascorbate-dependent oxidoreductase family", XP002785533, Retrieved from EBI Accession No. UNIPROT 11KB21, Database accession No. I1KB21, 2 pages.
Database UniProt, (Nov. 22, 2017). "Putative Homoserine Kinase," XP002780503, Retrieved from Database Accession No. A0A251RZI8, 1 page.
Jacobs et al., (2015). "Targeted genome modifications in soybean with CRISPR/Cas9," BMC Biotechnology, 15(1):16.
Li et al., (2016). "Loci and candidate gene identification for resistance to Phytophthora sojae via association analysis in soybean [*Glycine max* (L.) Merr.]," Molecular Genetics and Genomics, 291(3):1095-1103.
Preliminary Amendment, filed for U.S. Appl. No. 16/450,881, dated Jun. 25, 2019, 6 pages.
Preliminary Amendment, filed for U.S. Appl. No. 16/642,257, dated Feb. 26, 2020, 8 pages.
Preliminary Amendment, filed for U.S. Appl. No. 16/659,470, dated Dec. 12, 2019, 6 pages.
Qin et al., (2014). "Whole-Genome Sequencing of Cultivated and Wild Peppers Provides Insights into Capsicum Domestication and Specialization," PNAS, 111 (14):5135-5140.
Reply to communication from the Examining Division, filed during prosecution of EP2455475, dated Dec. 8, 2015, 7 pages.
Response to Final Office Action, filed for U.S. Appl. No. 15/314,778, dated Aug. 26, 2019, 10 pages.
Reply to Japanese Office Action dated Jun. 23, 2020 and Amended Claims, filed Aug. 31, 2020 during prosecution of Japanese Patent Application No. 2016-528486, 6 pages.
Response to Notice to File Missing Parts in a Non-provisional Application and Preliminary Amendment, filed for U.S. Appl. No. 16/773,781, dated Apr. 10, 2020, 6 pages.
Response to Restriction Requirement, filed for U.S. Appl. No. 16/361,089, dated May 22, 2020, 7 pages.
Submission by the proprietor in opposition proceedings for case EP2455474 dated May 29, 2020, concerning the staying of opposition proceedings, 5 pages.
Submission by the proprietor in opposition proceedings for case EP2455475 dated May 29, 2020, concerning the staying of opposition proceedings, 5 pages.
Submission by the proprietor in opposition proceedings for case EP2455479 dated May 29, 2020, concerning the staying of opposition proceedings, 5 pages.
Allowed Claims, Chinese Patent Application No. 201480045857.3, dated Jun. 8, 2020, 1 page.
Reply to Canadian Office Action dated Jun. 29, 2020 and Amended Claims, filed Oct. 20, 2020, during prosecution of Canadian Patent Application No. 2918706, 14 pages.
Reply to First Examination Report dated Feb. 25, 2020 and Amended Claims, filed Jul. 14, 2020 during prosecution of Indian Patent Application No. 201747001416, 8 pages.
U.S. Unpublished U.S. Appl. No. 16/642,257, filed Feb. 26, 2020, titled "Soybean Plants Resistant to Phytophthora Sojae," (Copy not submitted herewith pursuant to the waiver of 37 C.F.R. § 1.98(a)(2)(iii)).
Reply to Indian First Examination Report dated Jun. 29, 2021 and Amended Claims, filed Dec. 17, 2021 during prosecution of Indian Patent Application No. 202048010647, 6 pages.
Reply to Indian Office Action dated Dec. 20, 2021 and Amended Claims, filed Dec. 27, 2021 during prosecution of Indian Patent Application No. 201747001416, 3 pages.
U.S. Unpublished U.S. Appl. No. 17/551,119, filed Dec. 14, 2021, titled "Disease Resistant Petunia Plants," (Copy not submitted herewith pursuant to the waiver of 37 C.F.R. § 1.98(a)(2)(iii)).
Amended Claims, Japanese Patent Application No. 2008-538304, dated Oct. 23, 2009, 6 pages.
Badouin et al. (2017). "The sunflower genome provides insights into oil metabolism, flowering and Asterid evolution," Nature, 546(7656):148-153, 14 pages.
Forkmann et al. (1980). "Anthocyanin Biosynthesis in Flowers of Matthiola incana Flavanone 3- and Flavonoid 3'-Hydroxylases," Z. Naturforsch. 35 c, 691-695. DOI: https://doi.org/10.1515/znc-1980-9-1004.
Matvienko et al. (2011). Locus JI1587921, TSA: Lactuca sativa Letassy_X1_9021 mRNA sequence, direct submission to Genome Center, University of California Davis, Genome and Biomedical Sciences Facility, 2 pages.
Nakashima et al. (2018). "Structure function and engineering of multifunctional non-heme iron dependent oxygenases in fungal meroterpenoid biosynthesis," Nature Communication, 9:104, 10 pages.
Reply to Canadian Office Action dated Apr. 13, 2021 and Amended Claims, filed Aug. 10, 2021, during prosecution of Canadian Patent Application No. 2918706, 10 pages.
Reply to First Examination Report dated Nov. 8, 2019 and Amended Claims, filed Dec. 19, 2019 during prosecution of Indian Patent Application No. 201647027274, 6 pages.
Reply to Indian Office Action dated Jun. 25, 2021 and Amended Claims, filed Jun. 25, 2021 during prosecution of Indian Patent Application No. 201747001416, 20 pages.
Reply to Japanese Office Action dated Apr. 1, 2019, filed Jun. 20, 2019 during prosecution of Japanese Patent Application No. 2016-528486, 8 pages.
Reply to Japanese Office Action dated Mar. 27, 2018 and Amended Claims, filed Jun. 21, 2018 during prosecution of Japanese Patent Application No. 2016-528486, 12 pages.
Reply to Japanese Office Action dated May 29, 2012 and Amended Claims, filed Aug. 7, 2012 during prosecution of Japanese Patent Application No. 2008-538304, 12 pages.
Reply to Japanese Office Action dated Nov. 26, 2019 and Amended Claims, filed May 22, 2020 during prosecution of Japanese Patent Application No. 2019-11969, 6 pages.
Reply to Japanese Office Action dated Oct. 20, 2020 and Amended Claims, filed Oct. 30, 2020 during prosecution of Japanese Patent Application No. 2016-528486, 4 pages.
Request for Trial and Appeal, and Amended Claims, filed Aug. 8, 2013 during prosecution of Japanese Patent Application No. 2008-538304, 2 pages.

(56) References Cited

OTHER PUBLICATIONS

Request for Trial and Appeal, and Amended Claims, filed Jan. 28, 2019 during prosecution of Japanese Patent Application No. 2016-528486, 13 pages.
Response to Final Office Action, filed for U.S. Appl. No. 16/361,089, dated Apr. 20, 2021, 7 pages.

* cited by examiner

DISEASE RESISTANT PEPPER PLANTS

CROSS-REFERENCE TO RELATED APPLICATIONS

This application is a continuation-in-part application of U.S. patent application Ser. No. 15/314,778, filed Jun. 18, 2015, which is a U.S. National Phase application under 35 U.S.C. § 371 of International Application No. PCT/EP2015/063682, filed Jun. 18, 2015, which claims priority to International Application No. PCT/EP2014/062802, filed Jun. 18, 2014, each of which is incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 701802012220SEQLIST.TXT, date recorded: Jul. 6, 2020, size: 60 KB).

FIELD OF THE INVENTION

The present invention relates to *Phytophthora capsici* resistant *Capsicum annuum* plants wherein said resistance is conferred by a combination of two separate genes. The present invention further relates to proteins encoded by the present genes and the use of these genes for providing *Phytophthora capsici* resistant *C. annuum* plants.

BACKGROUND OF THE INVENTION

The plant pathogen *Phytophthora* (class: Oomycetes, order: Peronosporales, family: Pythiaceae) is a genus of plant-damaging Oomycetes (water molds) capable of causing large economic losses on crops worldwide, as well as environmental damage in natural ecosystems. *Phytophthora* pathogens are mostly pathogens of dicotyledons and generally are host-specific parasites. The genus was first described by Heinrich Anton de Bary in 1875. *Phytophthora* is sometimes referred to as a fungal-like organism but it is classified under a different kingdom: Chromalveolata (formerly Stramenopila and previously Chromista). *Phytophthora* is morphologically very similar to "true" fungi yet more closely related to plants than animals. Whereas fungal cell walls are made primarily of chitin, chromalveolata cell walls are constructed mostly of cellulose. Ploidy levels are different between these two groups: *Phytophthora* have diploid (paired) chromosomes in the vegetative (growing, non-reproductive) stage of life, fungi are almost always haploid in this state. Approximately 100 species of *Phytophthora* have been described amongst which economically important plant pathogens as *Phytophthora capsici* (hereinafter "*P. capsici*"), *Phytophthora infestans* (hereinafter "*P. infestans*"), and *Phytophthora nicotianae* (hereinafter "*P. nicotianae*"). In general, plant diseases caused by this genus are difficult to control chemically, and thus the growth of resistant cultivars is the main management strategy.

*Phytophthora infestans* was the infective agent of the potato blight that caused the Great Irish Famine (1845-1849), and still remains the most destructive pathogen of solanaceous crops, including tomato and potato.

*P. capsici* is the causative agent of *Phytophthora* blight, *Phytophthora* crown and root rot, and *Phytophthora* fruit rot in pepper, cucurbits, tomato, eggplant, and about 40 other plant species. *P. capsici* was first described by L. Leonian in 1922. In recent decades, the pathogen caused severe epidemics in Central and South America, Europe, Asia, and many states in the United States where susceptible vegetables are grown. In pepper, the roots, stems, foliage, and fruit are all susceptible. On the stem, the infection usually starts as a dark, water-soaked area at the soil line. As the infection develops, the lesions become dark brown to black and result in girdling and plant death. On the leaf, the infection starts as small, irregular to round, and water-soaked leaf spots. The infected areas may be bordered by white fungal-like growth during wet periods. Eventually the infected areas develops into large, light tan lesion that may crack. As the infection develops, rapid blighting of new leaves and the entire emerging shoot may take place. When infected, the roots become dark brown and mushy. Pepper fruits could be infected through the stem. Fruit rot appears as dark green, water-soaked areas that become covered with white-gray, cottony, fungal-like growth.

*P. capsici* has two mating types (called A1 and A2) that are morphologically identical but genetically distinct. When both mating types are present in one field, they mate to produce survival structures called oospores. Oospores can survive in the soil for many years and provide the initial inoculum for disease initiation in the spring when conditions become favorable. The asexual stage of *P. capsici*, which is responsible for initiating infection, depends on water for infecting and moving between plants. Disease will almost always begin in low spots of fields or in areas that do not drain readily. When contaminated soils are saturated for several hours and temperatures are relatively warm, *P. capsici* will form structures called sporangia, which contain asexual, swimming zoospores that are released into the saturated soil. Zoospores are attracted to living plant parts in the soil and on the soil surface and swim toward them. Once they find a host plant, zoospores can germinate and infect any plant part either in the soil (roots, crowns) or via splashing water (leaves, fruit). Under favorable conditions, *P. capsici* may re-infect crops several times throughout the growing season.

The Solanaceae, or nightshades, is an economically important family of flowering plants. The family ranges from herbs to trees, and includes a number of important agricultural crops, medicinal plants, spices, weeds, and ornamentals. Many members of the family contain potent alkaloids, and some are highly toxic. Solanaceae includes a number of commonly collected or cultivated species. Perhaps the most economically important genus of the family is *Solanum*, which comprises *Solanum tuberosum* (potato), *Solanum lycopersicum* (tomato), and *Solanum melongena* (aubergine or eggplant). Another important genus is *Capsicum* including *C. annuum* (chili peppers and sweet or bell peppers).

*C. annuum* originated in Mexico and the neighboring areas of Central America. *C. annuum* is grown as a crop in many countries; hot peppers are generally grown in Latin America and China, while the United States prefers bell peppers. *C. annuum* are an excellent source of Vitamin C, Vitamin A, and Calcium. The United States produces four percent of the world's *C. annuum* (chili peppers and sweet peppers), ranking sixth behind China, Mexico, Turkey, Spain and Nigeria. Bell peppers are the most common sweet pepper and are found in virtually every retail produce department. While *C. annuum* are grown commercially in most states, the U.S. *C. annuum* industry is largely concentrated in California and Florida, which together accounted for 78% of output in 2000. New Jersey, Georgia, and North Carolina round out the top five producing states (Economic Research Service, USDA, Vegetables and Melons Outlook/VGS-288/Dec. 14, 2001).

Considering the economic importance of *C. annuum* and the destructive effect of the plant pathogen *P. capsici*, it is an object, amongst other objects, of the present invention to provide *P. capsici* resistant *C. annuum* plants.

SUMMARY OF THE INVENTION

The object to provide *Phytophthora capsici* resistant *Capsicum annuum* plants, amongst other objects, is met by the present invention by providing plants as outlined in the appended claims.

Specifically, the above object of the present invention, amongst other objects, is met, according to a first aspect, by an isolated *Capsicum annuum* plant resistant to *Phytophthora capsici*, wherein the *Capsicum annuum* plant has a mutation introduced into a coding sequence of a first gene encoding a first protein comprising SEQ ID NO: 16 and a mutation introduced into a coding sequence of a second gene encoding a second protein comprising SEQ ID NO: 17, wherein the mutation in the coding sequence of the first gene results in an amino acid substitution in the first protein and the mutation in the coding sequence of the second gene results in an amino acid substitution in the second protein, and wherein the plant exhibits resistance to *Phytophthora capsici*. In some embodiments, the mutated first protein includes SEQ ID NO: 25 and the mutated second protein includes SEQ ID NO: 28. In some embodiments, the coding sequence of the first gene includes SEQ ID NO: 20 and the coding sequence of the second gene includes SEQ ID NO: 21.

In another embodiment, provided herein is a seed, tissue, or plant part of the *Capsicum annuum* plant resistant to *Phytophthora capsici*, wherein the seed, tissue, or plant part includes the mutation in the coding sequence of the first gene and the mutation in the coding sequence of the second gene and includes the mutated first protein and the mutated second protein. In some embodiments, the coding sequence of the first gene includes SEQ ID NO: 20, the coding sequence of the second gene includes SEQ ID NO: 21, the mutated first protein includes SEQ ID NO: 25, and the mutated second protein includes SEQ ID NO: 28.

In another aspect, provided herein are methods for obtaining a *Capsicum annuum* plant which is resistant to *Phytophthora capsici* including introducing a mutation into a coding sequence of a first gene encoding a first protein including SEQ ID NO: 16 and introducing a mutation into a coding sequence of a second gene encoding a second protein including SEQ ID NO: 17, wherein the mutation in the coding sequence of the first gene results in an amino acid substitution in the first protein and the mutation in the coding sequence of the second gene results in an amino acid substitution in the second protein. In some embodiments, the coding sequence of the first gene includes SEQ ID NO: 20 and the coding sequence of the second gene includes SEQ ID NO: 21. In some embodiments, the mutated first protein includes SEQ ID NO: 25 and the mutated second protein includes SEQ ID NO: 28.

In another embodiment, provided herein is a *Capsicum. annuum* plant produced from any of the preceding methods, wherein the plant includes the mutation in the coding sequence of the first gene and the mutation in the coding sequence of the second gene and includes the mutated first protein and the mutated second protein, and wherein the plant exhibits resistance to *Phytophthora capsici*. In some embodiments, the coding sequence of the first gene includes SEQ ID NO: 20 and the coding sequence of the second gene includes SEQ ID NO: 21. In some embodiments, the mutated first protein includes SEQ ID NO: 25 and the mutated second protein includes SEQ ID NO: 28.

In yet another embodiment, provided herein is a seed, tissue, or plant part of the *Capsicum annuum* plant produced from any of the preceding methods, wherein the seed, tissue, or plant part includes the mutation in the coding sequence of the first gene and the mutation in the coding sequence of the second gene and includes the mutated first protein and the mutated second protein. In some embodiments, the coding sequence of the first gene includes SEQ ID NO: 20, the coding sequence of the second gene includes SEQ ID NO: 21, the mutated first protein includes SEQ ID NO: 25, and the mutated second protein includes SEQ ID NO: 28.

In still another aspect, provided herein is an isolated *Capsicum annuum* plant including a first protein including SEQ ID NO: 25 and a second protein including SEQ ID NO: 28, wherein the plant exhibits resistance to *Phytophthora capsici*. In some embodiments, provided herein is a seed, tissue, or plant part of the *Capsicum annuum* plant, wherein the seed, tissue, or plant part of the *Capsicum annuum* plant includes the first protein and the second protein.

BRIEF DESCRIPTION OF THE DRAWINGS

The patent or application file contains at least one drawing executed in color. Copies of this patent or patent application publication with color drawings will be provided by the office upon request and payment of the necessary fee.

FIG. 2A shows leaves from plants silenced with a middle construct, silencing both SEQ ID NO: 7 and SEQ ID NO: 8. FIG. 2B shows leaves from chimeric silenced plants.

FIG. 7A shows results of an *A. thaliana* complementation test with CaDMR6-1 P215L and CaDMR6-2 P135L. The tested genotypes are *A. thaliana* Landsberg erecta (Ler eds; positive control), *A. thaliana* dmr6-1 mutant (dmr6-1; negative control), *A. thaliana* dmr6-1 mutant with constitutively expressed CaDMR6-1 P215L mutant allel (CaDMR6-1 P215L), and *A. thaliana* dmr6-1 mutant with constitutively expressed CaDMR6-2 P135L mutant allele (CaDMR6-2 P135L). FIG. 7B shows results of an *A. thaliana* complementation test with CaDMR6-1 G175 S, CaDMR6-1 T119M, CaDMR6-1 P215L, and CaDMR6-2 P135L. The tested genotypes are *A. thaliana* Landsberg erecta (Ler eds; positive control), *A. thaliana* dmr6-1 mutant (dmr6-1; negative control), *A. thaliana* dmr6-1 mutant with constitutively expressed CaDMR6-1 G175S mutant allel (G175S), *A. thaliana* dmr6-1 mutant with constitutively expressed CaDMR6-1 T119M mutant allel (T119M), *A. thaliana* dmr6-1 mutant with constitutively expressed CaDMR6-1 P215L mutant allel (P215L), and *A. thaliana* dmr6-1 mutant with constitutively expressed CaDMR6-2 P135L mutant allele (P135L); and the error bars represent standard error.

FIG. 12A shows a representative *C. annuum* plant of the 'dmr6-1/dmr6-2 WT' line, and the red circles indicate lesions caused by *P. capsici*. FIG. 12B shows a representative *C. annuum* plant of the 'dmr6-1/dmr6-2' line without lesions caused by *P. capsici*.

DETAILED DESCRIPTION

Figure 1:
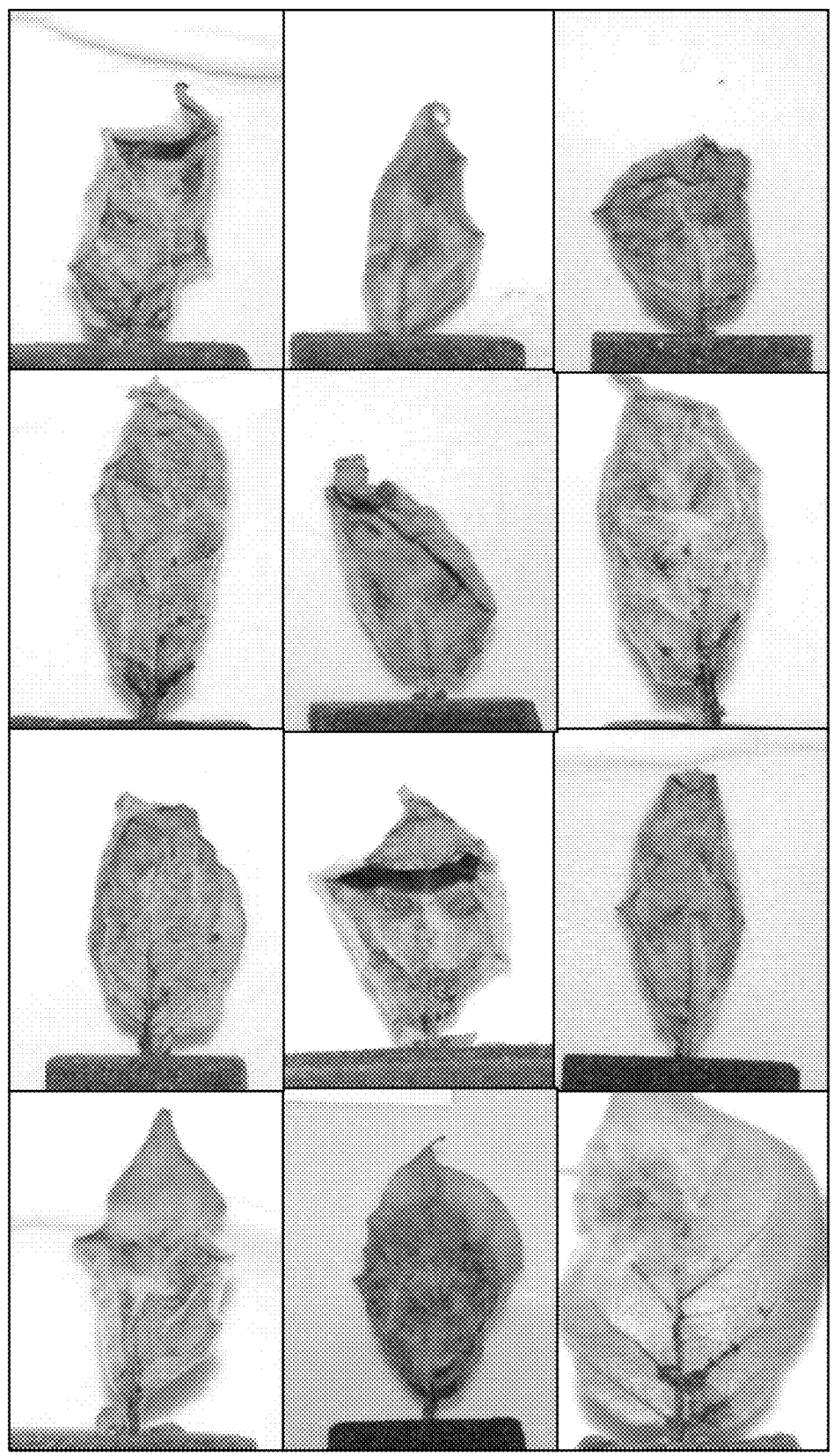
FIG. 1 shows a detached leaf assay of control potato plants after infection with *P. infestans*, wherein all leaves are infected by *P. infestans*.
Figure 2A:
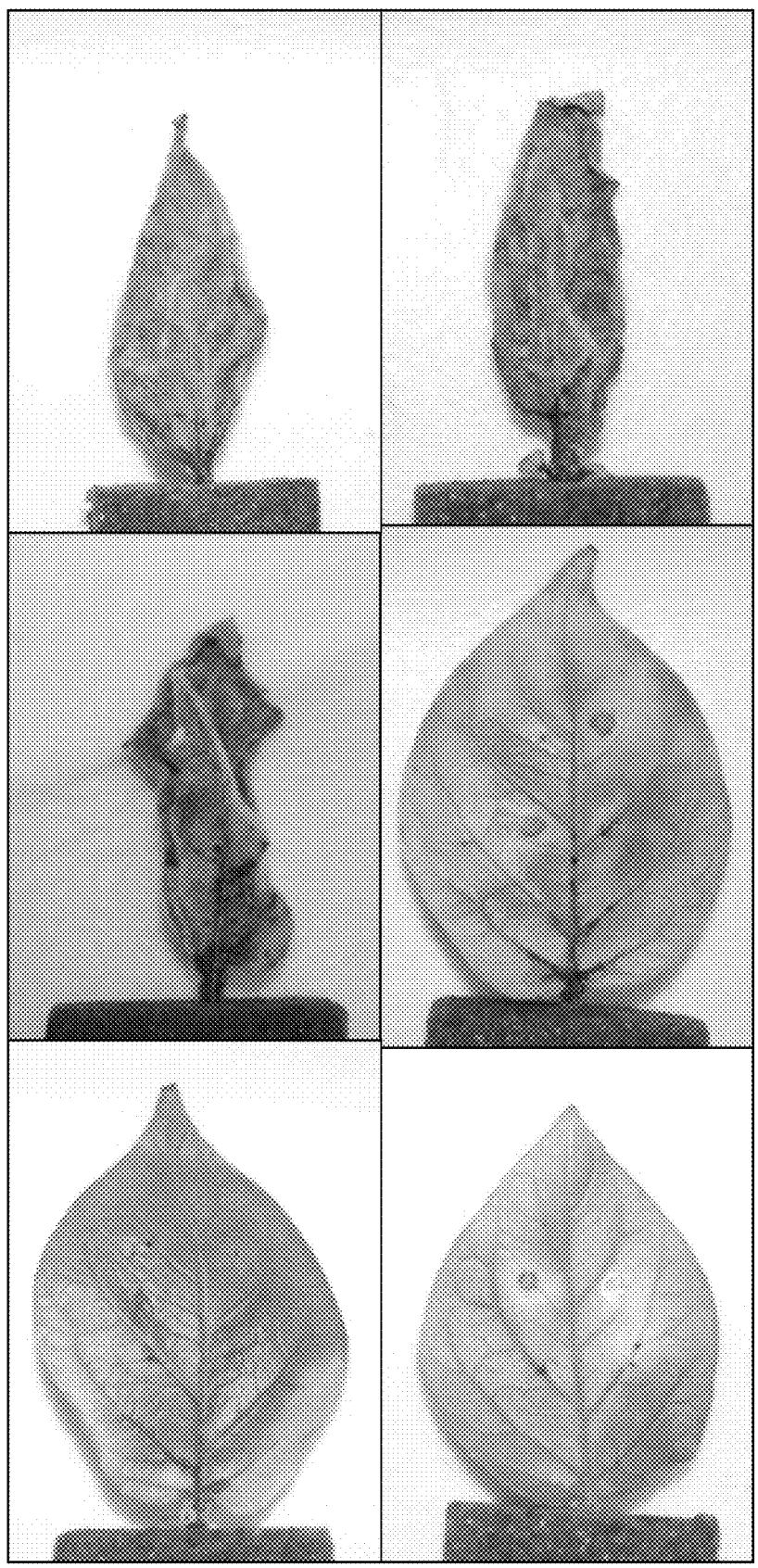
FIGS. 2A-2B shows a detached leaf assay of SEQ ID NO: 7 and SEQ ID NO: 8 silenced potato plants after infection with *P. infestans*, wherein each leaf is from an independent plant.
Figure 2B:
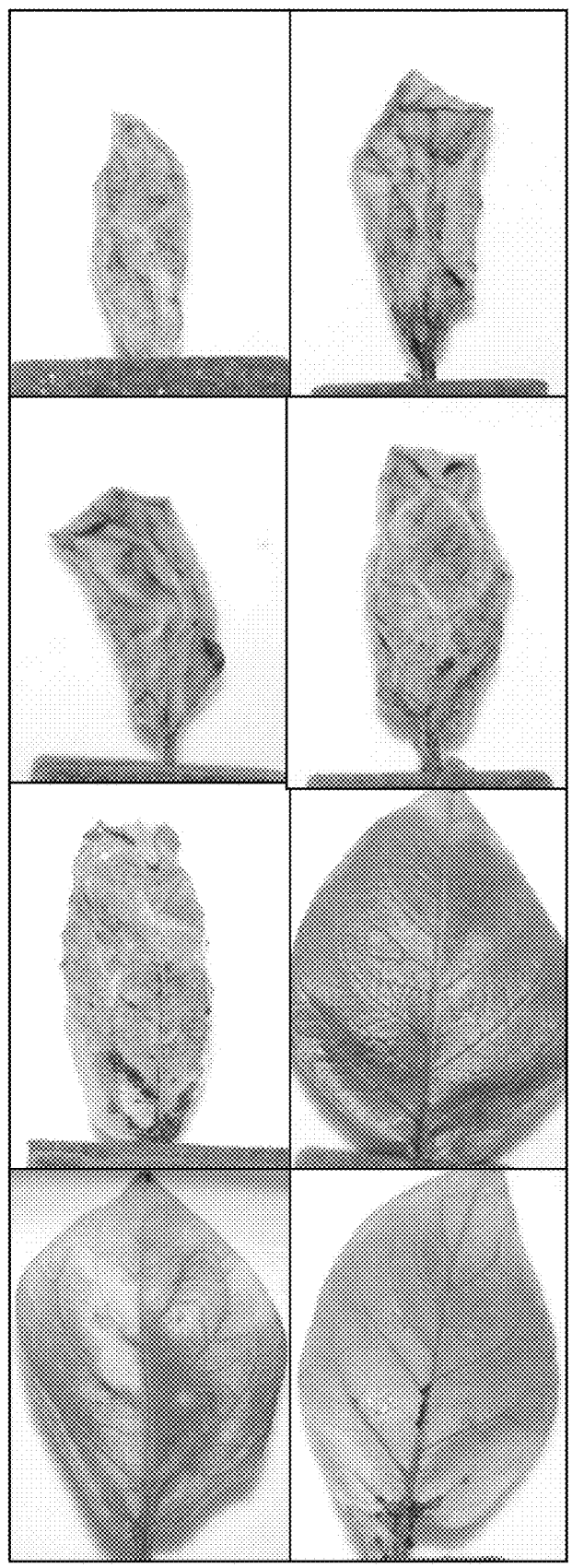
Figure 3:
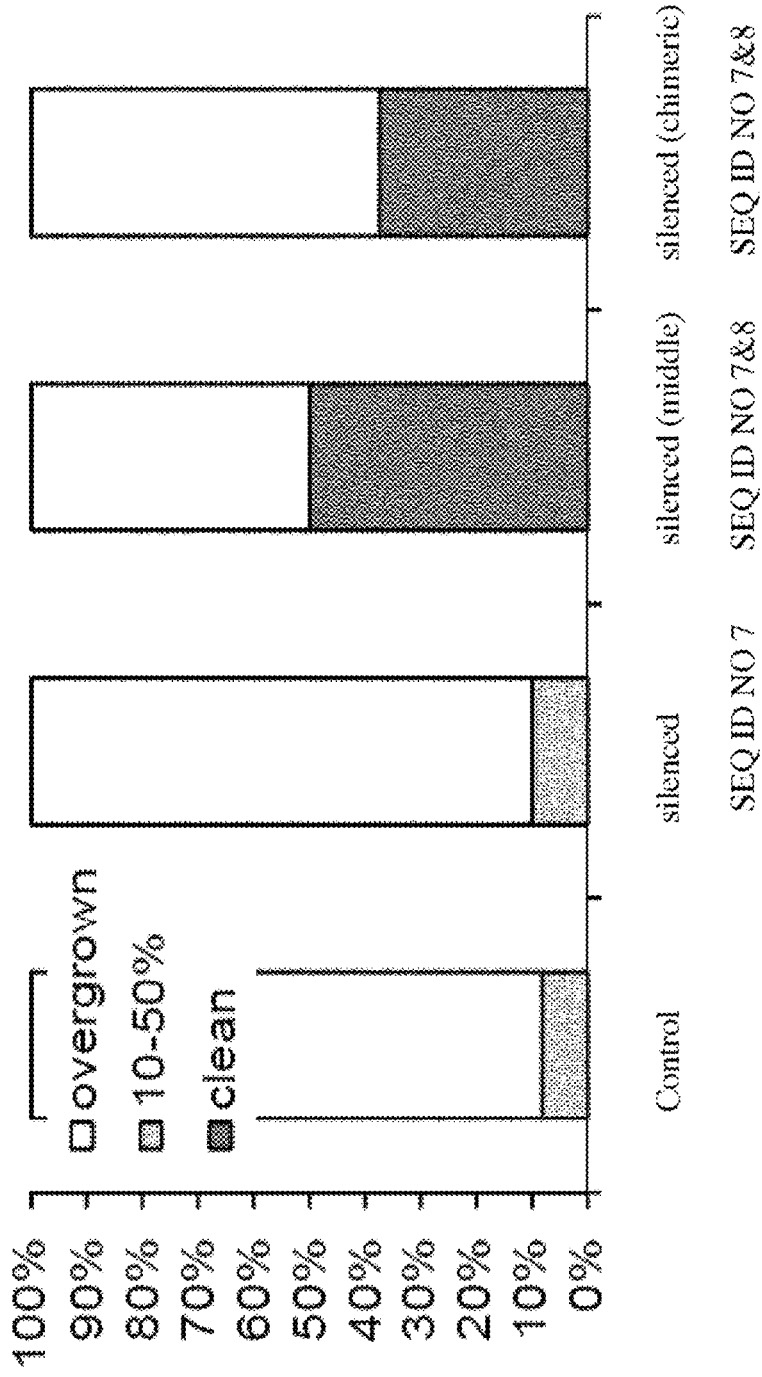
FIG. 3 shows the percentage of plants which are infected by *P. infestans*, wherein the first bar shows a control group (about 90% is completely overgrown), the second bar shows plants of which only SEQ ID NO: 7 is silenced (about 90% is completely overgrown), the third bar shows plants of which both SEQ ID NO: 7 and SEQ ID NO: 8 are silenced in the middle part of the respective sequences (about 50% clean), the fourth bar shows plants of which both SEQ ID NO: 7 and SEQ ID NO: 8 are silenced at the 5' end (about 40% clean). In each bar, white color represents the portion of plants that are overgrown (very infected) by *P. infestans*, light grey color represents the portion of plants that are 10-50% (partially) infected by *P. infestans*, and dark grey color represents the portion of plants that are clean (healthy).

Studies in *Arabidopsis thaliana* (hereinafter "*A. thaliana*") have shown that a number of genes encoding negative regulators of immunity are activated during pathogen infection so that the inducible defense response is controlled and down-regulated to prevent over-activation. Examples are the Nudix hydrolase-encoding NUDT7 and transcription factor-encoding WRKY48 that are induced upon infection or microbe-associated molecular pattern (MAMP) treatment. Similarly, the DOWNY MILDEW RESISTANT 6 gene (DMR6) is activated during infection with compatible and incompatible isolates of the downy mildew *Hyaloperonospora arabidopsidis*. Inactivation of DMR6 by mutation leads to a low constitutive activation of defense-related genes and resistance to the downy mildew *Hyaloperonospora arabidopsidis* (hereinafter "*H. arabidopsidis*").

DMR6 belongs to the superfamily of 2-oxoglutarate Fe(II) dependent oxygenases (2OG oxygenases, Pfam domain PF03171). This superfamily includes 151 members in *A. thaliana*. However, for most of these proteins, including DMR6, their metabolic activity is unknown. 2OG oxygenases are known to catalyze a plethora of reactions that involve the oxidation of a substrate using molecular $O_2$. They commonly use iron as co-factor and require 2-oxoglutarate as co-substrate for supplying two electrons. A general hallmark of these enzymes is the presence of the conserved $HxD/Ex_nH$ motif located on a double-stranded beta sheet. Together with two four-stranded beta sheets (jelly roll fold), it encapsulates the active center. 2OG oxygenases are implicated in secondary metabolism and biosynthesis of signaling molecules, e.g., the biosynthesis of flavonoids, gibberellins, and alkaloids.

Specifically, the above object of the present invention, amongst other objects, is met, according to a first aspect, by plants belonging to the Solanaceae family wherein the present plants comprise a genetic trait providing *Phytophthora* resistance and wherein the present resistance trait is encoded by a combination of at least two genes having a reduced expression, or reduced transcription, or a reduced activity of proteins encoded by the present genes as compared to the same plant belonging to Solanaceae family being susceptible to *Phytophthora*.

According to a preferred embodiment of this first aspect of the present invention, the present plants belonging to the Solanaceae family are selected from the group consisting of potato, petunia, tomato, aubergine, eggplant, tobacco and sweet pepper, more preferably potato, petunia, tomato, sweet pepper and tobacco.

According to another preferred embodiment of this first aspect of the present invention, the present *Phytophthora* resistance is resistance to a plant pathogen selected from the group consisting of *Phytophthora* spp., *P. capsici, P. infestans*, and *P. nicotianae*.

According to an especially preferred embodiment of this first aspect, the present invention relates to potato, the present *Phytophthora* resistance is resistance to *P. infestans* and the present combination of at least two genes are genes encoding proteins according to SEQ ID NO: 1 and SEQ ID NO: 2 or proteins having at least 80%, 85%, or 90% sequence identity with SEQ ID NO: 1 and SEQ ID NO: 2, such as 91%, 92%, 93% and 94% sequence identity, preferably at least 95% sequence identity, such as 96%, 97%, 98% and 99% sequence identity.

According to another especially preferred embodiment of this first aspect, the present invention relates to petunia, the present *Phytophthora* resistance is resistance to *P. nicotianae* and the present combination of at least two genes are genes encoding proteins according to SEQ ID NO: 3 and SEQ ID NO: 4 or proteins having at least 80%, 85%, or 90% sequence identity with SEQ ID NO: 3 and SEQ ID NO: 4, such as 91%, 92%, 93% and 94% sequence identity, preferably at least 95% sequence identity, such as 96%, 97%, 98% and 99% sequence identity.

According to another especially preferred embodiment of this first aspect, the present invention relates to tomato, the present *Phytophthora* resistance is resistance to *P. infestans* and the present combination of at least two genes are genes encoding proteins according to SEQ ID NO: 5 and SEQ ID NO: 6 or proteins having at least 80%, 85%, or 90% sequence identity with SEQ ID NO: 5 and SEQ ID NO: 6, such as 91%, 92%, 93% and 94% sequence identity, preferably at least 95% sequence identity, such as 96%, 97%, 98% and 99% sequence identity.

According to another especially preferred embodiment of this first aspect, the present invention relates to *C. annuum* or *Capsicum* spp., the *Phytophthora* resistance is resistance to *P. capsici* and the combination of at least two genes are genes encoding proteins according to SEQ ID NO: 16 and SEQ ID NO: 17 or proteins having at least 90% sequence identity with SEQ ID NO: 16 and/or SEQ ID NO: 17, preferably at least 95% sequence identity, most preferably at least 99% sequence identity.

According to another especially preferred embodiment of this first aspect, the present invention relates to *Nicotiana benthamiana*, the *Phytophthora* resistance is resistance to *P. capsici*; *P. infestans*; or *P. nicotianae*; or combinations thereof and said combination of at least two genes are genes encoding proteins according to SEQ ID NO: 18 and a protein having at least 70% sequence identity with SEQ ID NO: 18, preferably at least 85% sequence identity, most preferably at least 95% sequence identity.

According to another especially preferred embodiment of this first aspect, the present invention relates to tobacco (*Nicotiana tabacum*), the *Phytophthora* resistance is resistance to *P. capsici* and/or *P. infestans* and/or *P. nicotianae* and the combination of at least two genes are genes encoding proteins according to SEQ ID NO: 19 and a protein having at least 70% sequence identity with SEQ ID NO: 19, preferably at least 85% sequence identity, most preferably at least 95% sequence identity.

According to yet another especially preferred embodiment of this first aspect, the present invention relates to a plant belonging to the Solanaceae family wherein the present plant includes a genetic trait providing *Phytophthora* resistance, wherein the present resistance trait is obtainable by down regulating the activity of combination of two genes or reducing the activity of proteins encoded by the present genes in a *Phytophthora* susceptible plant, wherein the present two genes encode the combinations of SEQ ID NOs: 1 and 2 or SEQ ID NOs: 3 and 4 or SEQ ID NOs: 5 and 6 or proteins having at least 80%, 85%, or 90% sequence identity therewith such as 91%, 92%, 93% and 94% sequence identity, preferably at least 95% sequence identity, such as 96%, 97%, 98% and 99% sequence identity.

According to a further preferred embodiment, the present plant belonging to the Solanaceae family is selected from the group consisting of potato, petunia and tomato.

Given the advantageous properties of the present genes for providing *Phytophthora* resistance plants, the present invention relates, according to a second aspect, to the use of a combination of two genes, wherein said combination of two genes encode protein combinations selected from the group consisting of SEQ ID NOs: 1 and 2; SEQ ID NOs: 3 and 4; SEQ ID NOs: 5 and 6; SEQ ID NOs: 16 and 17; SEQ ID NO: 18 and a protein having at least 70% sequence identity with SEQ ID NO: 18, preferably at least 85% sequence identity, most preferably at least 95% sequence identity; and SEQ ID NO: 19 and a protein having at least 70% sequence identity with SEQ ID NO: 19, preferably at least 85% sequence identity, most preferably at least 95% sequence identity for providing *Phytophthora* resistance in plants belonging to the Solanaceae family.

According to the present invention, the present resistance is preferably a resistance against a plant pathogen selected from the group consisting of *Phytophthora* spp., *P. capsici*, *P. infestans*, and *P. nicotianae*.

According to a further preferred embodiment, the present use for providing *Phytophthora* resistance in plants belonging to the Solanaceae family includes reduced expression, or reduced transcription, of the present genes or a reduced activity of proteins encoded by the present genes as compared to the plant belonging to Solanaceae family being susceptible to *Phytophthora*.

According to a further preferred embodiment of this second aspect, the present plants belonging to the Solanaceae family are selected from the group consisting of *C. annuum*, *Capsicum* spp., *S. tuberosum*), petunia, *S. lycopersicum*, *N. benthamiana*, and *Nicotiana tabacum*.

Given the *Phytophthora* resistance providing properties of the present proteins and genes, the present invention relates according a third aspect to proteins and genes suitable for providing *Phytophthora* resistance to plants. Specifically, the present invention relates according to this third aspect to proteins selected from the group consisting of SEQ ID NO: 1, 2, 3, 4, 5, 6, 16, 17, 18 and 19 and proteins having at least 90% sequence identity therewith, preferably at least 95%, most preferably at least 99%.

*Capsicum annuum* Plants of the Present Disclosure

The object to provide *P. capsici* resistant *C. annuum* plants, amongst other objects, is met by the present invention by providing plants as outlined in the appended claims. Accordingly, certain aspects of the present disclosure relate to an isolated *C. annuum* plant resistant to *P. capsici*, wherein the *C. annuum* plant has a mutation introduced into a coding sequence of a first gene encoding a first protein including a polypeptide with at least 85% sequence identity, at least 88% sequence identity, at least 89% sequence identity, at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, or at least 99% sequence identity to SEQ ID NO: 16 and a mutation introduced into a coding sequence of a second gene encoding a second protein comprising a polypeptide with at least 85% sequence identity, at least 88% sequence identity, at least 89% sequence identity, at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, or at least 99% sequence identity to SEQ ID NO: 17, wherein the mutation in the coding sequence of the first gene results in an amino acid substitution in the first protein and the mutation in the coding sequence of the second gene results in an amino acid substitution in the second protein, and wherein the plant exhibits resistance to *Phytophthora capsici*. In some embodiments, the *C. annuum* plant has a mutation introduced into a coding sequence of a first gene encoding a first protein comprising SEQ ID NO: 16 and a mutation introduced into a coding sequence of a second gene encoding a second protein comprising SEQ ID NO: 17. In some embodiments that may be combined with any of the above embodiments, the mutated first protein is selected from the group of polypeptides with at least 85% sequence identity, at least 88% sequence identity, at least 89% sequence identity, at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, or at least 99% sequence identity to SEQ ID NO: 25; and the mutated second protein is selected from the group of polypeptides with at least 85% sequence identity, at least 88% sequence identity, at least 89% sequence identity, at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, or at least 99% sequence identity to SEQ ID NO: 28. In some embodiments, the mutated first protein includes SEQ ID NO: 25, and the mutated second protein includes SEQ ID NO: 28. In some embodiments, the coding sequence of the first gene includes a nucleotide with at least 85% sequence identity, at least 88% sequence identity, at least 89% sequence identity, at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, or at least 99% sequence identity to SEQ ID NO: 20; and the coding sequence of the second gene includes a nucleotide with 85% sequence identity, at least 88% sequence identity, at least 89% sequence identity, at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, or at least 99% sequence identity to SEQ ID NO: 21. In some embodiments, the coding sequence of the first gene includes SEQ ID NO: 20 and the coding sequence of the second gene includes SEQ ID NO: 21. In some embodiments, the mutation in the coding sequence of the first gene results in a nucleotide with at least 85% sequence identity, at least 88% sequence identity, at least 89% sequence identity, at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, or at least 99% sequence identity to SEQ ID NO: 29; and the mutation in the coding sequence of the second gene includes a nucleotide with 85% sequence identity, at least 88% sequence identity, at least 89% sequence identity, at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, or at least 99% sequence identity to SEQ ID NO: 32. In some embodiments, the mutated first coding sequence includes SEQ ID NO: 29 and the mutated second coding sequence includes SEQ ID NO: 32. In some embodiments, which may be combined with any of the preceding embodiments, the first gene is a CaDMR6-1 gene, the second gene is a CaDMR6-2 gene, the first protein is a CaDMR6-1 polypeptide, and the second protein is a CaDMR6-2 polypeptide.

In some embodiments, which may be combined with any of the preceding embodiments, the mutation that results in a mutated CaDMR6-1 protein is an altered amino acid in a conserved domain of the CaDMR6-1 protein; and the mutation that results in a mutated CaDMR6-2 protein is an altered amino acid in a conserved domain of the CaDMR6-2 protein. In one embodiment, the plant of the present disclosure may be obtained through introduction of an altered amino acid into *C. annuum* CaDMR6-1 and CaDMR6-2 genes. In a particular embodiment, the cytosine (C) is replaced with a thymine (T) at a position of CaDMR6-1 corresponding to nucleotide 644 of the reference sequence SEQ ID NO: 20 (e.g., producing SEQ ID NO: 29), resulting in a change from Proline (P) to a Leucine (L) (e.g., producing SEQ ID NO: 25). In another particular embodiment, the guanine (G) is replaced with a adenine (A) at a position of CaDMR6-1 corresponding to nucleotide 523 of the reference sequence SEQ ID NO: 20 (e.g., producing SEQ ID NO: 30), resulting in a change from Glycine (G) to a Serine (S) (e.g., producing SEQ ID NO: 26). In a further particular embodiment, the C is replaced with an T at a position of CaDMR6-1 corresponding to nucleotide 356 of the reference sequence of the reference sequence SEQ ID NO: 20 (e.g., producing SEQ ID NO: 31) resulting in a change from Threonine (T) to a Methionine (M) (e.g., producing SEQ ID NO: 27). In an additional particular embodiment, the C is replaced with an T at a position of CaDMR6-2 corresponding to nucleotide 404 of the reference sequence SEQ ID NO: 21 (e.g., producing SEQ ID NO: 32) resulting in a change from P to a L (e.g., producing SEQ ID NO: 28). In some embodiments, the non-natural mutation introduced into the CaDMR6-1 gene is selected from the group of a C to T mutation at a position corresponding to nucleotide 644 of reference sequence SEQ ID NO: 20, a G to A mutation at a position corresponding to nucleotide 523 of reference sequence SEQ ID NO: 20, or a C to T mutation at a position corresponding to nucleotide 356 of reference sequence SEQ ID NO: 20.

In some embodiments, the mutation introduced into the CaDMR6-1 gene is selected from the group of a C to T mutation at position 644 corresponding to the reference sequence SEQ ID NO: 29, a G to A mutation at position 523 corresponding to the reference sequence SEQ ID NO: 30, or a C to T mutation at position 356 corresponding to the reference sequence SEQ ID NO: 31; and the mutation introduced into the CaDMR6-2 gene is a C to T mutation at position 404 corresponding to reference sequence SEQ ID NO: 32.

In another embodiment, provided herein is a seed, tissue, or plant part of the *C. annuum* plant resistant to *P. capsici*, wherein the seed, tissue, or plant part includes the mutation in the coding sequence of the first gene and the mutation in the coding sequence of the second gene and includes the mutated first protein and the mutated second protein. In some embodiments, the coding sequence of the first gene includes a nucleotide with at least 85% sequence identity, at least 88% sequence identity, at least 89% sequence identity, at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, or at least 99% sequence identity to SEQ ID NO: 20; the coding sequence of the second gene includes a nucleotide with 85% sequence identity, at least 88% sequence identity, at least 89% sequence identity, at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, or at least 99% sequence identity to SEQ ID NO: 21; the mutated first protein includes a polypeptide with at least 85% sequence identity, at least 88% sequence identity, at least 89% sequence identity, at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, or at least 99% sequence identity to SEQ ID NO: 25; and the mutated second protein includes a polypeptide with at least 85% sequence identity, at least 88% sequence identity, at least 89% sequence identity, at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, or at least 99% sequence identity to SEQ ID NO: 28. In some embodiments, the coding sequence of the first gene includes SEQ ID NO: 20, the coding sequence of the second gene includes SEQ ID NO: 21, the mutated first protein includes SEQ ID NO: 25, and the mutated second protein includes SEQ ID NO: 28. In some embodiments, the mutation in the coding sequence of the first gene results in a nucleotide with at least 85% sequence identity, at least 88% sequence identity, at least 89% sequence identity, at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, or at least 99% sequence identity to SEQ ID NO: 29; and the mutation in the coding sequence of the second gene includes a nucleotide with 85% sequence identity, at least 88% sequence identity, at least 89% sequence identity, at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, or at least 99% sequence identity to SEQ ID NO: 32. In some embodiments, the mutated first coding sequence includes SEQ ID NO: 29 and mutated second coding sequence includes SEQ ID NO: 32.

In another aspect, provided herein is an isolated *C. annuum* plant including a first protein including a polypeptide with at least 85% sequence identity, at least 88% sequence identity, at least 89% sequence identity, at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, or at least 99% sequence identity to SEQ ID NO: 25 and a second protein including a polypeptide with at least 85% sequence identity, at least 88% sequence identity, at least 89% sequence identity, at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, or at least 99% sequence identity to SEQ ID NO: 28, wherein the plant exhibits resistance to *Phytophthora capsici*. In some embodiments, the first protein includes SEQ ID NO: 25 and the second protein includes SEQ ID NO: 28. In some embodiments, the isolated *C. annuum* plant further includes a coding sequence of a first gene encoding the first protein including a nucleotide with at least 85% sequence identity, at least 88% sequence identity, at least 89% sequence identity, at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, or at least 99% sequence identity to SEQ ID NO: 29; and a coding sequence of a second gene encoding the second protein including a nucleotide with 85% sequence identity, at least 88% sequence identity, at least 89% sequence identity, at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, or at least 99% sequence identity to SEQ ID NO: 32. In some embodiments, the coding sequence of the first gene includes SEQ ID NO: 29 and the coding sequence of the second gene includes SEQ ID NO: 32. In some embodiments, provided herein is a seed, tissue, or plant part of the *C. annuum* plant, wherein the seed, tissue, or plant part of the *C. annuum* plant includes the first protein and the second protein. In some embodiments, the first protein includes a polypeptide with at least 85% sequence identity, at least 88% sequence identity, at least 89% sequence identity, at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, or at least 99% sequence identity to SEQ ID NO: 25 and the second protein includes a polypeptide with at least 85% sequence identity, at least 88% sequence identity, at least 89% sequence identity, at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, or at least 99% sequence identity to SEQ ID NO: 28. In some embodiments, the first protein includes SEQ ID NO: 25 and the second protein includes SEQ ID NO: 28. In some embodiments, the seed, tissue, or plant part of the *C. annuum* plant further includes the coding sequence of the first gene encoding the first protein including a nucleotide with at least 85% sequence identity, at least 88% sequence identity, at least 89% sequence identity, at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, or at least 99% sequence identity to SEQ ID NO: 29; and the coding sequence of the second gene encoding the second protein including a nucleotide with 85% sequence identity, at least 88% sequence identity, at least 89% sequence identity, at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, or at least 99% sequence identity to SEQ ID NO: 32. In some embodiments, the coding sequence of the first gene includes SEQ ID NO: 29 and the coding sequence of the second gene includes SEQ ID NO: 32.

In some embodiments of any of the above embodiments, the present disclosure relates to a plant part, wherein the plant part is a leaf, a stem, a root, a flower, a seed, a fruit, a cell, or a portion thereof. In some embodiments, the plant part is a leaf.

In some aspects, the present disclosure relates to a pollen grain or an ovule of the plant of any of the above embodiments. In some aspects, the present disclosure relates to a protoplast produced from the plant of any of the above embodiments. In some aspects, the present disclosure relates to a tissue culture produced from protoplasts or cells from the plant of any of the above embodiments, wherein the cells or protoplasts are produced from a plant part selected from the group of leaf, anther, pistil, stem, petiole, root, root primordia, root tip, fruit, seed, flower, cotyledon, hypocotyl, embryo, or meristematic cell. In some aspects, the present disclosure relates to a plant seed produced from the plant of any of the above embodiments.

In order to determine whether a plant is a plant of the present disclosure, and therefore whether said plant has the same alleles as plants of the present disclosure, the phenotype of the plant can be compared with the phenotype of a known plant of the present disclosure. In one embodiment, the phenotype can be assessed by, for example, the susceptibility to downy mildew in a leaf assay or a whole plant assay.

In the leaf assay, the fourth leaf is removed from each plant (three to four weeks old) and placed on wet filter paper in a plastic tray covered with a glass lid. 5 μl inoculum (40,000 spores/ml) of P. capsici isolate Q108 are pipetted onto the underside of each leaf (drop inoculation). Trays are kept in a climate cell at 20° C. with 16 hours light. The leaves are misted with tap water periodically. At 13 days post inoculation (dpi), the percentage of infected leaves is calculated by counting the number of leaves showing disease symptoms 13 dpi, and then dividing that number by the total number of leaves infected.

In the whole plant assay, three to four weeks old plants are misted with a solution of P. capsici isolate Q108 with a spore concentration of 40,000 spores ml$^{-1}$ and kept in a tent at 100% relative humidity in the greenhouse. At 2 days post spray with P. capsici, the tent is opened slightly and at 5 days post inoculation the tent is opened fully. The test is incubated at 25° C. during the day and 20° C. during the night; the test is shaded against direct sunlight. The number of lesions on each plant are counted at 7 days post inoculation.

In addition to phenotypic observations, the genotype of a plant can also be examined. There are many laboratory-based techniques known in the art that are available for the analysis, comparison and characterization of plant genotype. Such techniques include, without limitation, Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length polymorphisms (AFLPs), Simple Sequence Repeats (SSRs, which are also referred to as Microsatellites), and Single Nucleotide Polymorphisms (SNPs). In some embodiments, PCR-based detection of SNPs is used to identify plants of the present disclosure. In some embodiments, High-Resolution Melting Curve (HRM) based detection of SNPs and/or zygosity testing is used to identify plants of the present disclosure. By using these techniques, it is possible to assess the presence of the alleles, genes, and/or loci involved in the downy mildew resistance phenotype of the plants of the present disclosure.

Methods for Obtaining C. annuum Plants of the Present Disclosure

Further aspects of the present disclosure relate to methods for obtaining a C. annuum plant which is resistant to P. capsici including: introducing a mutation into a coding sequence of a first gene encoding a first protein including a polypeptide with at least 85% sequence identity, at least 88% sequence identity, at least 89% sequence identity, at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, or at least 99% sequence identity to SEQ ID NO: 16 and introducing a mutation into a coding sequence of a second gene encoding a second protein including a polypeptide with at least 85% sequence identity, at least 88% sequence identity, at least 89% sequence identity, at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, or at least 99% sequence identity to SEQ ID NO: 17, wherein the mutation in the coding sequence of the first gene results in an amino acid substitution in the first protein and the mutation in the coding sequence of the second gene results in an amino acid substitution in the second protein. In some embodiments, the mutation is introduced into a coding sequence of a first gene encoding a first protein comprising SEQ ID NO: 16 and the mutation is introduced into a coding sequence of a second gene encoding a second protein comprising SEQ ID NO: 17. In some embodiments, the coding sequence of the first gene includes a nucleotide with at least 85% sequence identity, at least 88% sequence identity, at least 89% sequence identity, at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, or at least 99% sequence identity to SEQ ID NO: 20; and the coding sequence of the second gene includes a nucleotide with 85% sequence identity, at least 88% sequence identity, at least 89% sequence identity, at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, or at least 99% sequence identity to SEQ ID NO: 21. In some embodiments, the coding sequence of the first gene includes SEQ ID NO: 20 and the coding sequence of the second gene includes SEQ ID NO: 21. In some embodiments, the mutation in the coding sequence of the first gene results in a nucleotide with at least 85% sequence identity, at least 88% sequence identity, at least 89% sequence identity, at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, or at least 99% sequence identity to SEQ ID NO: 29; and the mutation in the coding sequence of the second gene includes a nucleotide with 85% sequence identity, at least 88% sequence identity, at least 89% sequence identity, at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, or at least 99% sequence identity to SEQ ID NO: 32. In some embodiments, the mutated first coding sequence includes SEQ ID NO: 29 and the mutated second coding sequence includes SEQ ID NO: 32. In some embodiments, the mutated first protein is selected from the group of polypeptides with at least 85% sequence identity, at least 88% sequence identity, at least 89% sequence identity, at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, or at least 99% sequence identity to SEQ ID NO: 25; and the mutated second protein is selected from the group of polypeptides with at least 85% sequence identity, at least 88% sequence identity, at least 89% sequence identity, at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, or at least 99% sequence identity to SEQ ID NO: 28. In some embodiments, the mutated first protein includes SEQ ID NO: 25 and the mutated second protein includes SEQ ID NO: 28. In some embodiments, which may be combined with any of the preceding embodiments, the first gene is a CaDMR6-1 gene, the second gene is a CaDMR6-2 gene, the first protein is a CaDMR6-1 polypeptide, and the second protein is a CaDMR6-2 polypeptide.

In some embodiments, the mutation is achieved by a mutagenic treatment (e.g., EMS), a radiation treatment, or a gene editing technique. In some embodiments, the gene editing technique is selected from the group of transcription activator-like effector nuclease (TALEN) gene editing techniques, clustered Regularly Interspaced Short Palindromic Repeat (CRISPR/Cas9) gene editing techniques, or zinc-finger nuclease (ZFN) gene editing techniques.

In another embodiment, provided herein is a *C. annuum* plant produced from any of the preceding methods, wherein the plant includes the mutation in the coding sequence of the first gene and the mutation in the coding sequence of the second gene and includes the mutated first protein and the mutated second protein, and wherein the plant exhibits resistance to *Phytophthora capsici*. In another embodiment, provided herein is a seed, tissue, or plant part of the *C. annuum* plant resistant to *P. capsici*, wherein the seed, tissue, or plant part includes the mutation in the coding sequence of the first gene and the mutation in the coding sequence of the second gene and includes the mutated first protein and the mutated second protein. In some embodiments, the coding sequence of the first gene includes a nucleotide with at least 85% sequence identity, at least 88% sequence identity, at least 89% sequence identity, at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, or at least 99% sequence identity to SEQ ID NO: 20; and the coding sequence of the second gene includes a nucleotide with 85% sequence identity, at least 88% sequence identity, at least 89% sequence identity, at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, or at least 99% sequence identity to SEQ ID NO: 21. In some embodiments, the coding sequence of the first gene includes SEQ ID NO: 20 and the coding sequence of the second gene includes SEQ ID NO: 21. In some embodiments, the mutated first protein is selected from the group of polypeptides with at least 85% sequence identity, at least 88% sequence identity, at least 89% sequence identity, at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, or at least 99% sequence identity to SEQ ID NO: 25; and the mutated second protein is selected from the group of polypeptides with at least 85% sequence identity, at least 88% sequence identity, at least 89% sequence identity, at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, or at least 99% sequence identity to SEQ ID NO: 28. In some embodiments, the mutated first protein includes SEQ ID NO: 25 and the mutated second protein includes SEQ ID NO: 28. In some embodiments, the mutated first coding sequence includes a nucleotide with at least 85% sequence identity, at least 88% sequence identity, at least 89% sequence identity, at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, or at least 99% sequence identity to SEQ ID NO: 29; and the mutated second coding sequence includes a nucleotide with 85% sequence identity, at least 88% sequence identity, at least 89% sequence identity, at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, or at least 99% sequence identity to SEQ ID NO: 32. In some embodiments, the mutated first coding sequence includes SEQ ID NO: 29 and the mutated second coding sequence includes SEQ ID NO: 32.

The resistance according to the invention is based on an altered level, a reduced level, a reduced activity, or mutation of CaDMR6-1 and CaDMR6-2 proteins in planta. The term "CaDMR6-1 and CaDMR6-2 proteins" in this respect relates to the CaDMR6-1 and CaDMR6-2 gene products. Such alterations can be achieved in various ways.

In one embodiment of the invention, the reduced level of CaDMR6-1 and CaDMR6-2 proteins is the result of a reduced endogenous CaDMR6-1 and CaDMR6-2 gene expression. Reducing the expression of the CaDMR6-1 and CaDMR6-2 genes can be achieved, either directly, e.g., by targeting CaDMR6-1 and CaDMR6-2, or indirectly by modifying the regulatory sequences thereof, or by stimulating repression of the gene. In some embodiments, endogenous CaDMR6-1 and CaDMR6-2 expression may be reduced by any suitable methodology including, without limitation, gene silencing, RNA interference (RNAi), virus-induced gene silencing (VIGS), small RNA-mediated post-transcriptional gene silencing, transcription activator-like effector nuclease (TALEN) gene editing techniques, clustered Regularly Interspaced Short Palindromic Repeat (CRISPR/Cas9) gene editing techniques, and zinc-finger nuclease (ZFN) gene editing techniques.

Modulating the CaDMR6-1 and CaDMR6-2 genes to lower their activity or expression can be achieved at various levels. First, the endogenous gene can be directly mutated. This can be achieved by means of a mutagenic treatment. Alternatively, modified CaDMR6-1 and CaDMR6-2 genes can be brought into the plant by means of transgenic techniques or by introgression, or the expression of CaDMR6-1 and CaDMR6-2 can be reduced at the regulatory level, for example by modifying the regulatory sequences or by modulating gene expression by, for example, gene silencing, RNA interference (RNAi), virus-induced gene silencing (VIGS), small RNA-mediated post-transcriptional gene silencing, transcription activator-like effector nuclease (TALEN) gene editing techniques, clustered Regularly Interspaced Short Palindromic Repeat (CRISPR/Cas9) gene editing techniques, or zinc-finger nuclease (ZFN) gene editing techniques.

In another embodiment of the present disclosure, the reduced level of CaDMR6-1 and CaDMR6-2 protein is the result of a mutation in the CaDMR6-1 gene and the CaDMR6-2 gene resulting in a reduced CaDMR6-1 and CaDMR6-2 expression as compared to the wild-type CaDMR6-1 and CaDMR6-2 genes wherein no such mutation is present, or resulting in reduced mRNA stability or protein stability. In a particular embodiment, this is achieved by mutations in the CaDMR6-1 and CaDMR6-2 coding sequence that result in amino acid substitutions in the CaDMR6-1 and CaDMR6-2 proteins.

In another embodiment of the invention, reduced expression can be achieved by down-regulation of CaDMR6-1 and CaDMR6-2 gene expression either at the transcriptional or the translational level, e.g. by gene silencing or by mutations that affect the expression of the CaDMR6-1 and CaDMR6-2 gene.

To achieve a reduced CaDMR6-1 and CaDMR6-2 protein level, the expression of the CaDMR6 gene can be down-regulated or the enzymatic activity of the CaDMR6-1 and CaDMR6-2 protein can be reduced by amino acid substitutions resulting from nucleotide changes in the CaDMR6-1 and CaDMR6-2 coding sequence.

In a particular embodiment of the invention, downregulation of CaDMR6-1 and CaDMR6-2 gene expression is achieved by gene-silencing using RNAi. For this, transgenic plants are generated expressing CaDMR6-1 and CaDMR6-2 anti-sense constructs, optimized micro-RNA constructs, inverted repeat constructs, or combined sense-anti-sense constructs, so as to generate dsRNA corresponding to CaDMR6-1 and CaDMR6-2 that lead to gene silencing.

In an alternative embodiment, one or more regulators of the CaDMR6-1 and CaDMR6-2 genes are downregulated (in case of transcriptional activators) by RNAi.

In another embodiment regulators are upregulated (in case of repressor proteins) by transgenic overexpression. Overexpression is achieved in a particular embodiment by expressing repressor proteins of the CaDMR6-1 and CaDMR6-2 genes from a strong promoter, e.g. the 35S promoter that is commonly used in plant biotechnology.

Mutations in the CaDMR6-1 and CaDMR6-2 coding sequences may lead to amino acid substitutions or premature stop codons that negatively affect the expression or activity of the encoded CaDMR6-1 and CaDMR6-2 proteins. In a particular embodiment of the invention, the mutations in the CaDMR6-1 and CaDMR6-2 coding sequences are amino acid substitutions. In a further embodiment, mutations in the two *C. annuum* CaDMR6-1 and CaDMR6-2 genes introduce an amino acid substitution into each of the CaDMR6-1 and CaDMR6-2 proteins.

These mutations are induced in plants by using mutagenic chemicals such as ethyl methane sulfonate (EMS), by irradiation of plant material with gamma rays or fast neutrons, or by other means. The resulting nucleotide changes are random, but in a large collection of mutagenized plants the mutations in the CaDMR6-1 and CaDMR6-2 genes can be readily identified by using the TILLING (Targeting Induced Local Lesions IN Genomes) method (McCallum et al. (2000) Targeted screening for induced mutations. Nat. Biotechnol. 18, 455-457, and Henikoff et al. (2004) TILLING. Traditional mutagenesis meets functional genomics. Plant Physiol. 135, 630-636). The principle of this method is based on the PCR amplification of the gene of interest from genomic DNA of a large collection of mutagenized plants in the M2 generation. By DNA sequencing or by looking for point mutations using a single-strand specific nuclease, such as the CEL-I nuclease (Till et al. (2004) Mismatch cleavage by single-strand specific nucleases. Nucleic Acids Res. 32, 2632-2641) the individual plants that have a mutation in the gene of interest are identified.

By screening many plants, a large collection of mutant alleles is obtained, each giving a different effect on gene expression or enzyme activity. The gene expression or protein levels can for example be tested by analysis of CaDMR6-1 or CaDMR6-2 transcript levels (e.g. by RT-PCR) or by quantification of CaDMR6-1 or CaDMR6-2 protein levels with antibodies. Plants with the desired CaDMR6-1 and plants with the desired CaDMR6-2 mutation are then crossed to produce CaDMR6-1 and CaDMR6-2 double mutant plant. The CaDMR6-1 and CaDMR6-2 double mutant plant can further back-crossed or crossed to other breeding lines to transfer only the desired new alleles into the background of the crop wanted.

The invention further relates to mutated CaDMR6-1 and CaDMR6-2 genes. In a particular embodiment, the invention relates to CaDMR6-1 and CaDMR6-2 alleles with mutations that result in amino acid substitutions, such as the CaDMR6-1 mutant allele of SEQ ID NO: 29 and the CaDMR6-2 mutant allele of SEQ ID NO: 32. In SEQ ID NO: 29, the mutation is a nucleotide change located at the SNP, and in SEQ ID NO: 32, the mutation is a nucleotide change located at the SNP.

In a particular embodiment, the present invention relates to a method of providing disease resistance in a plant, comprising transforming a plant cell with a DNA construct comprising at least one expressible nucleic acid which is operably linked to a pathogen-inducible promoter that is operable within a plant cell, and regenerating transformed plants from said plant cells, wherein the pathogen-inducible promoter is a CaDMR6-1 or CaDMR6-2 promoter, and wherein the expression of the expressible nucleic acid confers disease resistance to the transgenic plant. The invention also relates to disease resistance plants, obtainable by said method, as well as to plant tissue, and seeds obtained from said plants.

The invention in particular relates to plants, which are resistant to a pathogen of viral, bacterial, fungal or oomycete origin, wherein the plant includes in its genome a DNA construct, comprising at least one expressible nucleic acid which is operably linked to a pathogen-inducible promoter, wherein the pathogen-inducible promoter is a CaDMR6-1 or CaDMR6-2 promoter.

The present invention also relates to the DNA construct per se, comprising at least one expressible nucleic acid which is operably linked to a pathogen-inducible promoter, wherein the pathogen-inducible promoter is a CaDMR6-1 or CaDMR6-2 promoter. The construct of the invention can be used to transform plant cells which may be regenerated into transformed plants. Furthermore, transformed plant tissue and seed may be obtained. Suitable methods for introducing the construct of the invention into plant cells are known to the skilled person.

According to the invention, by "operably linked" it is meant that a promoter and an expressible nucleic acid, e.g. a gene, are connected in such way as to permit initiation of transcription of the expressible nucleic acid (e.g. gene) by the promoter.

By "expressible nucleic acid" it is meant that a nucleic acid (e.g. a gene, or part of a gene) can be expressed in the cell, i.e., can be transcribed into mRNA, and eventually may be translated into a protein. The expressible nucleic acid may be genomic DNA, cDNA, or chemically synthesized DNA or any combination thereof.

According to the present invention, a DNA construct includes all necessary nucleic acid elements which permit expression (i.e. transcription) of a particular nucleic acid in a cell. Typically, the construct includes an expressible nucleic acid, i.e. a nucleic acid to be transcribed, and a promoter. The construct can suitably be incorporated into e.g. a plasmid or vector.

The expressible nucleic acid preferably is a gene involved in a plant defense response, e.g. a gene associated with the hypersensitivity response of a plant. In the hypersensitivity response (HR) of a plant, the site in the plant where the pathogen invades undergoes localized cell death by the induced expression of a suicide mechanism that triggers said localized cell death in response to pathogens. In this way, only a few plant cells are sacrificed and the spread of the pathogen is effectively arrested. Examples of said genes involved in a plant defense response are the regulatory protein NPR1/NIM1 (Friedrich et al., Mol. Plant Microbe Interact. 14(9): 1114-1124, 2001) and the transcription factor MYB30 (Vailleau et al., Proc. Natl. Acad. Sci. USA 99(15): 10179-10184, 2002).

In a particular embodiment, the expressible nucleic acid encodes an autologous or heterologous polypeptide capable of conferring disease-resistance to a plant. By "autologous polypeptide" is meant any polypeptide that is expressed in a transformed plant cell from a gene that naturally occurs in the transformed plant cell. By "heterologous polypeptide", any polypeptide that is expressed in a transformed plant cell from a gene that is partly or entirely foreign (i.e., does not naturally occur in) to the transformed plant cell is meant. Examples of such polypeptides are the mammalian Bax protein, which encodes a pro-apoptotic protein and results in cell death in plants (Lacomme and Santa Cruz, Proc. Natl. Acad. Sci. USA 96(14): 7956-61, 1999) and fungal chitinases (de las Mercedes Dana et al., Plant Physiol. 142(2): 722-730, 2006).

In a further preferred embodiment, the promoter is an orthologous DMR6 promoter. Once the DMR6 orthologs have been identified, the skilled person will be able to isolate the respective promoter of said orthologs, using standard molecular biological techniques.

The present invention is illustrated in the following examples that are not intended to limit the invention in any way. In the examples reference is made to the figures described above.

EXAMPLES

Example 1

Introduction

In this example, the resistance to *Phytophthora* spp. mediated by DMR6 orthologs in potato, petunia, tomato, and *N. benthamiana* was investigated.

Materials and Methods

RNAi Constructs Targeting Potato SEQ ID NOs: 7 and 8

3 different RNAi constructs were made, harboring/targeting:

1. 5' end of SEQ ID NO:7: equivalent to coding sequence −159-200 (−159 from start means in 5'utr).
2. Chimera of 5' end of SEQ ID NOs: 7 and 8: equivalent to coding sequence 4-199+1-204.
3. Middle part of SEQ ID NO: 7 (highly homologous to middle of SEQ ID NO:8): equivalent to coding sequence 334-743.

The fragments were amplified from genomic DNA and cloned into the pENTR-D-TOPO vector. For the chimeric construct, 2 fragments were coupled using primers with complementary overhangs, and subsequent extension and amplification to create the fused fragment. Fragments were transferred using a Gateway LR reaction to the RNAi vector pK7GWiWG2 (Karimi et al., 2002, Trends Plant Sci 7), creating an inverted repeat with hairpin structure. Because the pK7GWiWG2 vector requires Streptomycin for bacterial selection, and the *Agrobacterium* strain used for potato transformation (LBA4404) already carries a Streptomycin selection marker, the complete RNAi (hairpin) cassette was transferred to a different plant transformation vector, pGreen0029 (bacterial as well as plant selection marker is Kanamycin) (Hellens et al., 2000, Plant Mol Biol 42). The final constructs allow stable expression of a 35S-promoter driven hairpin RNA that forms a silencing-inducing dsRNA, after the hairpin-loop forming intron gets spliced out. At least six independent T1 transformants were maintained for each construct.

P. Infestans Assay in Potato

Detached leaves were taken from T1 (first generation transgenic) plants, and placed in a tray with 100% RH with petioles in wet cotton-wool or Oasis. *P. infestans* zoospores/sporangia were harvested from *P. infestans* cultures (rye-sucrose-agar plates), and a 10 ul drop of spore suspension containing $10^3$ sporangia ($10^5$/ml) was placed on each side of the midvein. Trays were incubated at 18° C. Leaf infection rates were scored on day 11. Leaves with completely infected/overgrown infection were scored as 1; leaves with partial infection (10-50% infected area) were scored as 2; and clean (<10% infected area) leaves were scored as 3.

Petunia Transposon Insertion Lines

Petunia transposon insertion lines were identified from a collection/library (Vandenbussche et al., 2008, Plant Journal 54). Two dTph1 transposon insertion alleles were found in SEQ ID NO:9 and three dTph1 transposon insertion alleles in SEQ ID NO:10. Several crosses were made to generate double mutants.

*P. Nicotianae* Assay in Petunia

Petunia plants were grown in standard potting soil, individually potted, at 23° C. *P. nicotianae* spores were harvested from cultures (lima-bean-agar or V8-agar plates), and 2 ml of spore suspension containing $10^4$ (assay Sept) spores was dripped onto the soil with each plant. Plant collapse was monitored regularly.

Tomato Overexpression Lines and Silencing Lines

Tomato plants were transformed with two constructs, either for providing overexpression of both SEQ ID NO: 11 and 12, or for providing silencing of both SEQ ID NO: 11 and 12. Tomato SEQ ID NO: 11 silencing constructs were generated using Gateway cloning of a 300 bp fragment identical to the middle part of the CDS of SEQ ID NO: 11. Sequence:

```
                                         (SEQ ID NO: 15)
TTGGGTGAACAAGGACAACATATGGCTATCAATTATTATCCTCCTTGTCC

ACAACCAGAACTTACTTATGGGCTTCCGGCCCATACTGATCCAAATTCAC

TTACAATTCTTCTTCAAGACTTGCAAGTTGCGGGTCTTCAAGTTCTTAAA

GATGGCAAATGGTTAGCTGTAAAACCTCAACCTGACGCCTTTGTCATTAA

TCTTGGGGATCAATTGCAGGCAGTAAGTAACGGTAAGTACAGAAGTGTAT

GGCATCGAGCTATTGTGAATTCAGATCAAGCTAGGATGTCAGTGGCTTCG

TTT
```

Using primers:

```
    S. lycopersicum AttB1-F
                                         (SEQ ID NO: 13)
    AAAAAGCAGGCTTCTTGGGTGAACAAGGACAACA S. lycopersicum AttB2-R
                                         (SEQ ID NO: 14)
    AGAAAGCTGGGTAAAACGAAGCCACTGACATCC
```

The generated ENTRY vector was Gateway cloned into the pHellsgate12 binary vector. After this, *Agrobacterium* transformation was done according to standard procedure for tomato. The silencing constructs were able to silence both SEQ ID NO: 11 and 12, due to similarities in the sequences.

*P. Infestans* Assay in Tomato

Figure 4:
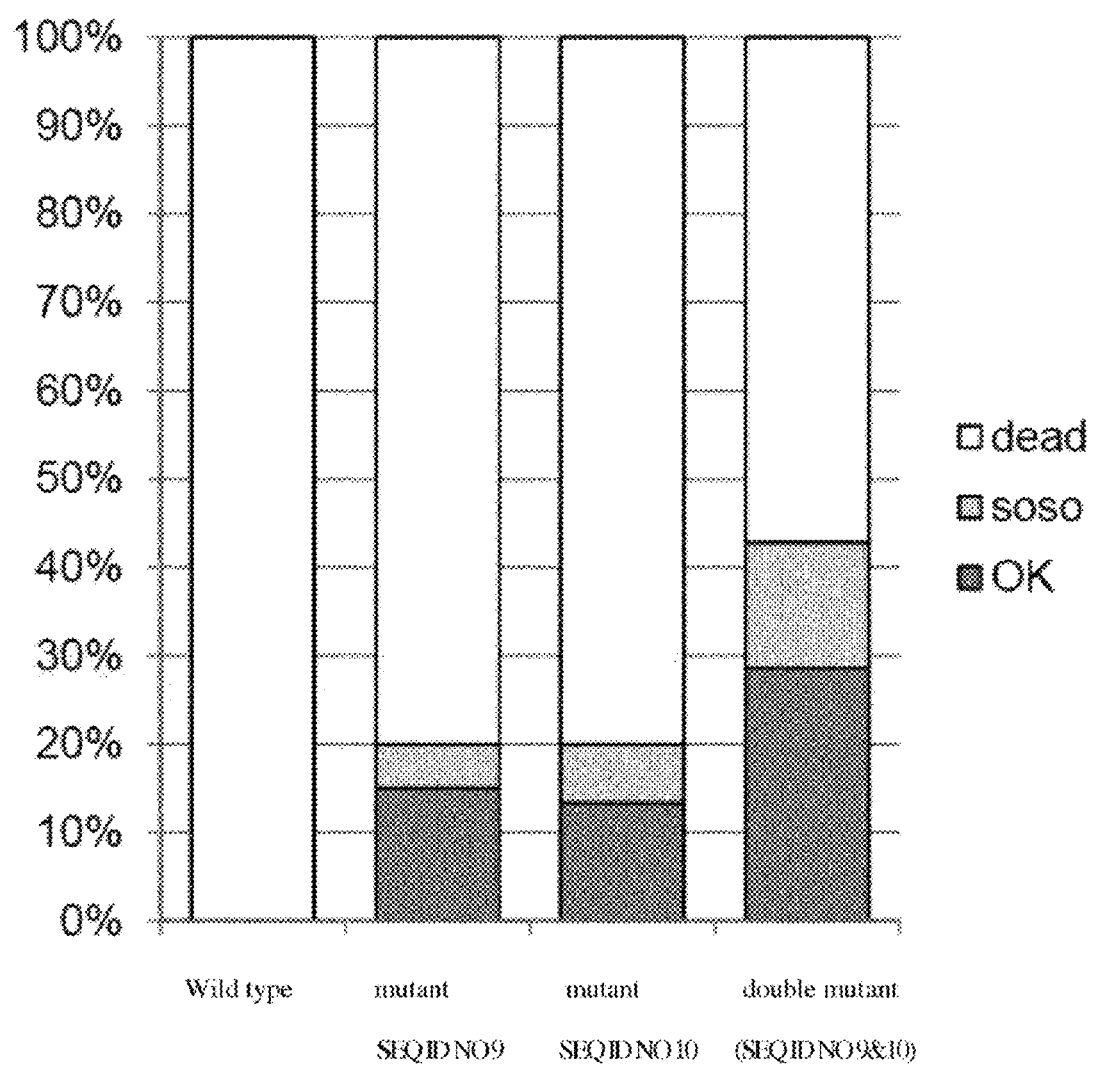
FIG. 4 shows the percentages of living petunia plants after inoculation with *P. nicotianae*, wherein the first bar shows wild type control plant (0% living plants), the second bar shows SEQ ID NO: 9 mutants (20% living plants), the third bar shows SEQ ID NO: 10 mutants (20% living plants) and the fourth bar shows double mutants, i.e., both SEQ ID NO: 9 and SEQ ID NO: 10 (45% living plants). In each bar, white color represents the portion of plants that are dead, light grey color represents the portion of plants that are soso (living symptomatic), and dark grey color represents the portion of plants that are OK (living asymptomatic).

Offspring from transformed tomato plants were subjected to a disease test by inoculation of *P. infestans* isolate US11. Seven days after inoculation the plants were visually analysed by scoring leaves on a visual scale from 1 to 9, wherein 1 means susceptible and 9 means resistant. Tomato lines TS33, TS19, and OT9 were used as susceptible control. The known resistant wild accession LA1269 was used as resistant control. Eight leaves from each plant were measured.

VIGS Silencing of *N. Benthamiana* DMR6 Ortholog

To investigate if DMR6 mediated resistance in *N. benthamiana* against *P. infestans*, the DMR6 ortholog was cloned in an VIGS expression vector.

Sequence of DMR6 silencing construct:

(SEQ ID NO: 24)
```
ACAACTCGGGTTCAGATTGCAGGAAGCCATAGCAGAGAGCCTAGGCTTAG
AGAAAGAGTGTATAAAGGATGTATTGGGCGAACAAGGTCAACACATGGCT
ATCAATTTCTATCCTCCTTGTCCACAACCAGAACTCACTTATGGGCTGCC
AGCACATACTGATCCAAATGCCCTTACAATTCTTCTTCAAGACTTAGAAG
TAGCTGGTCTTCAAGTTCTTAAAGATGGCGAATGGTTGGCCGTCAAGCCT
CAACCAGATGCCTTTGTCATTAATCTTGGTGATCAACTGCAGGCAGTGAG
TAATGGGAGATACAAAAGCGTATGGCATCGAGCTATTGTAAATTCAGACA
AAGCCAGGTTGTCAGTGGCTTCGTTCCTTTGTCCGTGCGATAGCGCGAAA
ATCAGTGCT
```

VIGS was used to silence and test the function of *N. benthamiana* DMR6. As a visual control for the procedures, the PDS gene was also targeted. The PDS silenced plants were used to indicate at which time the silencing started. The silencing must have started ±2 days before the bleaching was observed due to the protein levels already established in the plant. But at the start of the silencing time frame, the silencing would not be at a high rate and waiting two days therefore gave the mechanism time to establish a good silencing rate. Another advantage of using PDS silenced plants was that they give an indication which parts of the plants are silenced.

The bleaching was observed in all parts above the inoculation. In the vacuum inoculated plants, the new tissue showed strong photobleaching and parts of some of the cotyledons showed white areas as well. In the syringe inoculated plants, the bleaching was the strongest in the youngest leaves, because in full grown leaves the pigment was already synthesized and silencing was harder to observe visually. Bleaching of the PDS silenced plants was observed 8-10 days past inoculation with the *Agrobacterium* strain containing the TRV vector. Two separate VIGS experiments were performed. Plants from both experiments were used for detached leaf infection assays.

*P. Infestans* and *P. Capsici* Assays in *N. Benthamiana*

*N. benthamiana* plants were silenced for DMR6 and subsequently drop-inoculated with a spore solution of *P. infestans*. Up to 7 dpi, plants were scored for disease development. This experiment was performed three times with similar results. DMR6 silencing clearly resulted in less colonization by the pathogen compared to the empty vector control or wild type non-silenced plants.

The *P. capsici* infection assay was done 8 days after Agro-infiltration of the DMR6 silencing construct, on leaves 2-6 above infiltrated leaves. Zoospore solution containing $5\times10^3$ spores/ml was applied to detached leaves.

Results

*P. Infestans* Assay in Potato

FIG. 2A shows that the double silenced (SEQ ID NOS: 7 and 8) plants were only 50% infected, FIG. 2B shows that the double silenced (chimeric) plants were only 60% infected, whereas FIG. 1 shows that all plants in the control group were infected. As shown in FIG. 3, 40% to 50% of the SEQ ID NO: 7 and SEQ ID NO: 8 double silenced plants were clean, whereas only 10% of the plants having only SEQ ID NO: 7 silenced (single silenced plants) scored partially infected. Accordingly, silencing of both SEQ ID NO: 7 and 8 provided resistance to *P. infestans*.

P. Nicotianae Assay in Petunia As shown in FIG. 4, double mutants, i.e., plants having mutations in both SEQ ID NO: 9 and SEQ ID NO: 10, had a percentage of living plants of 45%, whereas the percentage of living plants of single mutants (mutation in SEQ ID NO: 9 or SEQ ID NO: 10) was only 20%.

P. infestans Assay in Tomato

Eight leaves from each transformed tomato plant were measured. Table 1 below provides the average score from the 8 leaves per plant.

TABLE 1

| Tomato line | Tomato line description | Average resistance score |
|---|---|---|
| LA1269 | Resistant control | 8.7 |
| TS33 | Susceptible control | 1.3 |
| TS19 | Susceptible control | 1.5 |
| OT9 | Susceptible control | 2.0 |
| 551-06-01 | Overexpression | 2.8 |
| 551-06-02 | Overexpression | 3.3 |
| 551-06-03 | Overexpression | 3.0 |
| 551-06-07 | Overexpression | 1.5 |
| 551-06-08 | Overexpression | 2.3 |
| 551-06-09 | Overexpression | 2.3 |
| 551-06-12 | Overexpression | 2.3 |
| 556-02-01 | Silencing | 6.5 |
| 556-02-02 | Silencing | 8.5 |
| 556-02-03 | Silencing | 8.3 |
| 556-02-06 | Silencing | 7.3 |
| 556-02-11 | Silencing | 7.3 |
| 556-01-01 | Silencing | 7.8 |
| 556-01-02 | Silencing | 8.3 |
| 556-01-03 | Silencing | 8.5 |
| 556-01-04 | Silencing | 8.5 |
| 556-01-05 | Silencing | 8.5 |
| 556-01-06 | Silencing | 6.0 |
| 556-01-07 | Silencing | 5.5 |
| 556-01-08 | Silencing | 8.5 |
| 556-01-09 | Silencing | 7.0 |
| 556-01-10 | Silencing | 8.5 |
| 556-01-11 | Silencing | 8.8 |
| 556-01-12 | Silencing | 7.8 |

Figure 5:
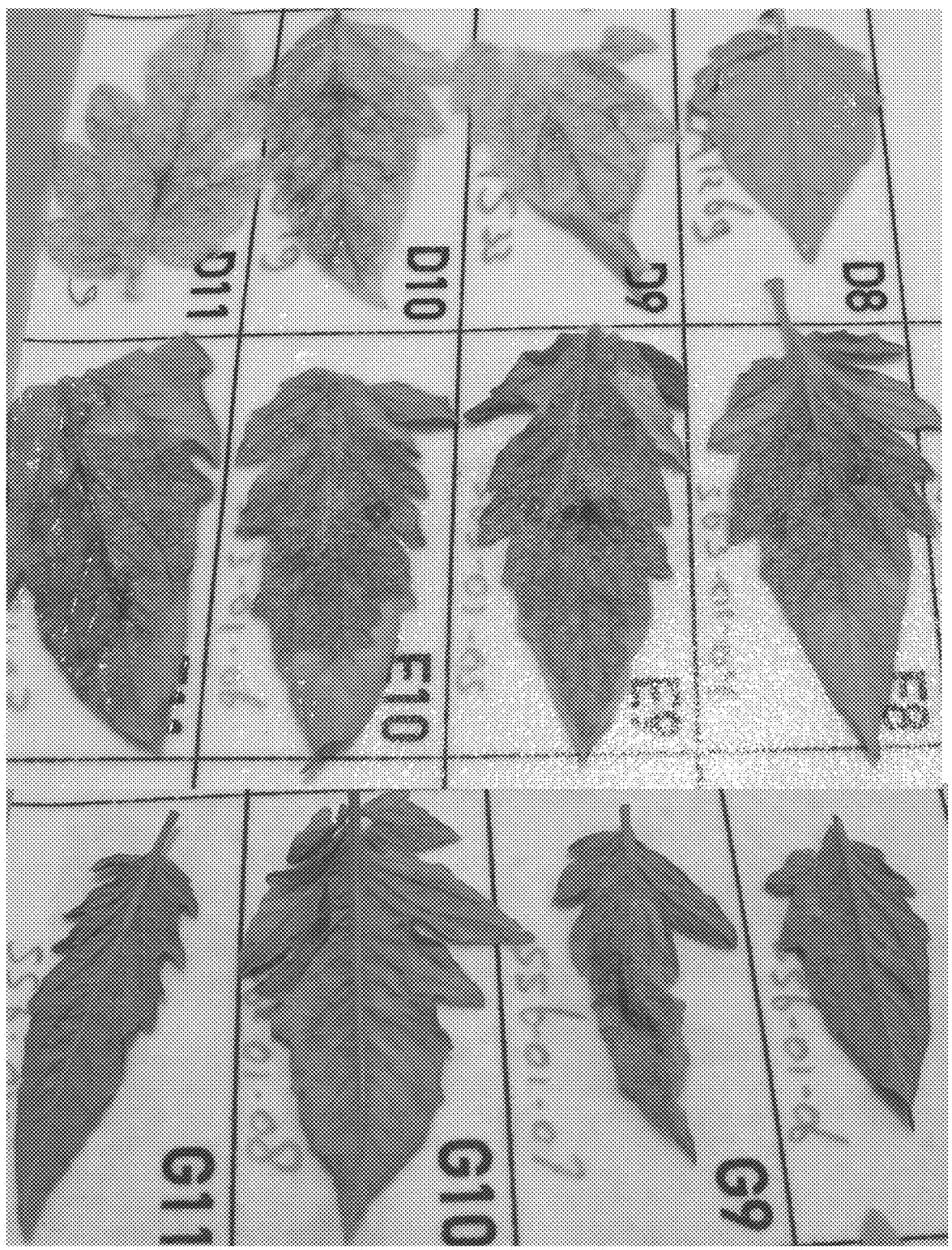
FIG. 5 shows leaves of tomato plants from a *P. infestans* disease test.
Figure 6:
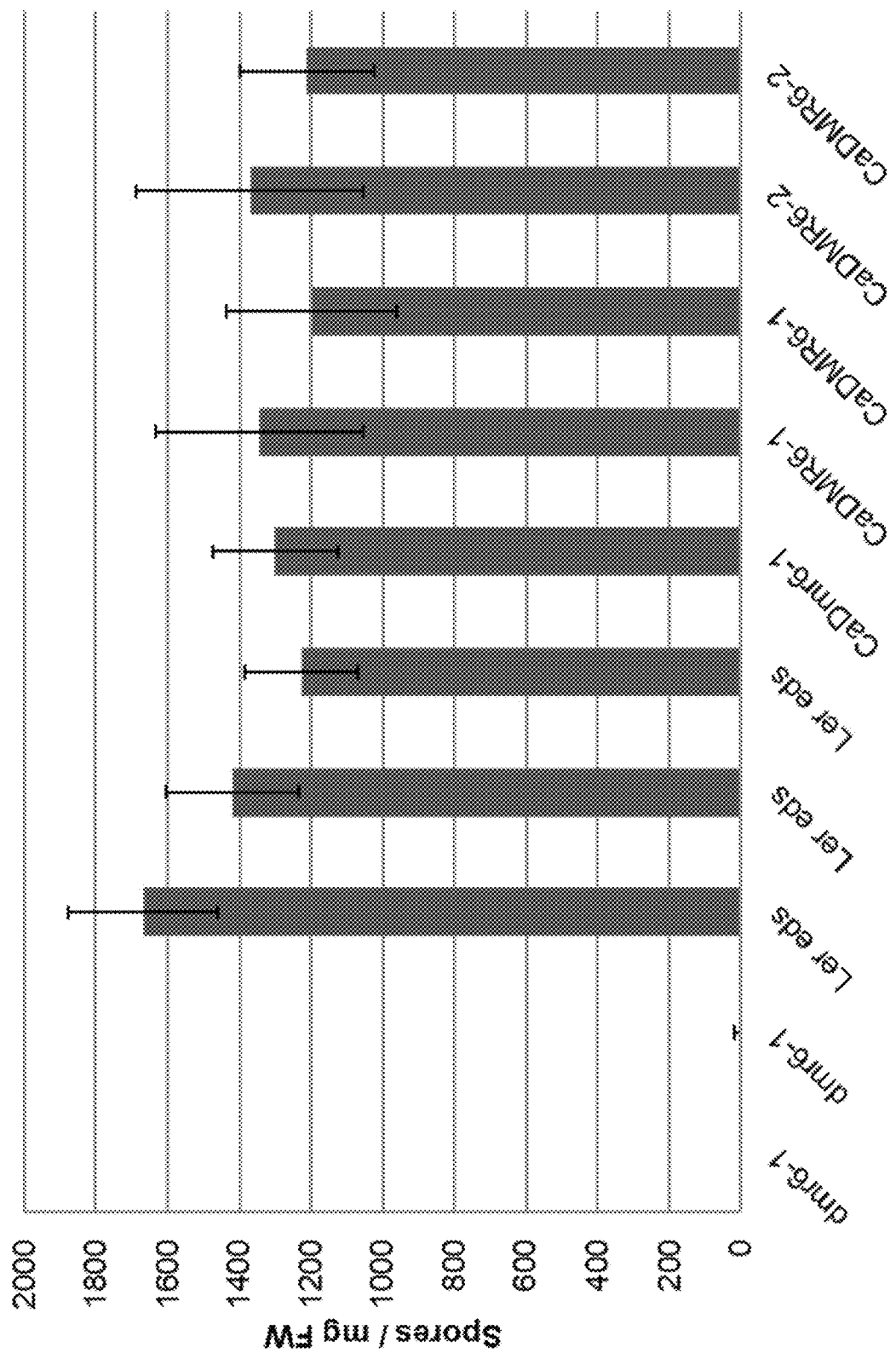
FIG. 6 shows results of a complementation test for disease resistance phenotypes in *Arabidopsis thaliana* using wild type CaDMR6-1 and CaDMR6-2 alleles. The tested genotypes are *Arabidopsis thaliana* (hereinafter "*A. thaliana*") dmr6-1 mutant (dmr6-1; negative control), *A. thaliana* Landsberg erecta (Ler eds; positive control), *A. thaliana* dmr6-1 mutant with constitutively expressed CaDMR6-1 gene (CaDMR6-1), and *A. thaliana* dmr6-1 mutant with constitutively expressed CaDMR6-2 gene (CaDMR6-2). The bars represent independent lines of the tested genotypes, the error bars represent standard deviation.
Figure 7A:
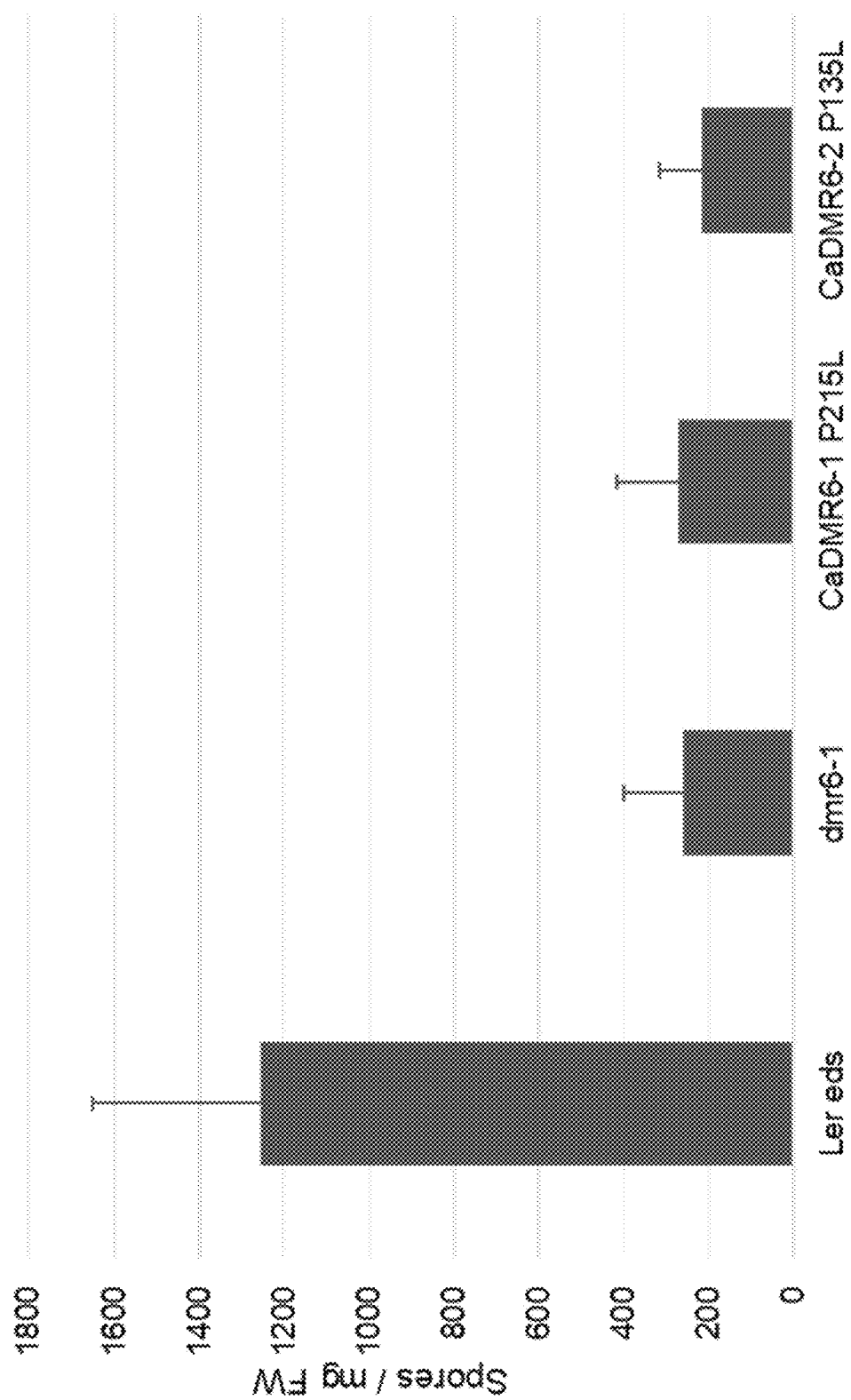
FIGS. 7A-7B show results of a complementation test for disease resistance phenotypes in *A. thaliana* using CaDMR6-1 and CaDMR6-2 mutant alleles.
Figure 7B:
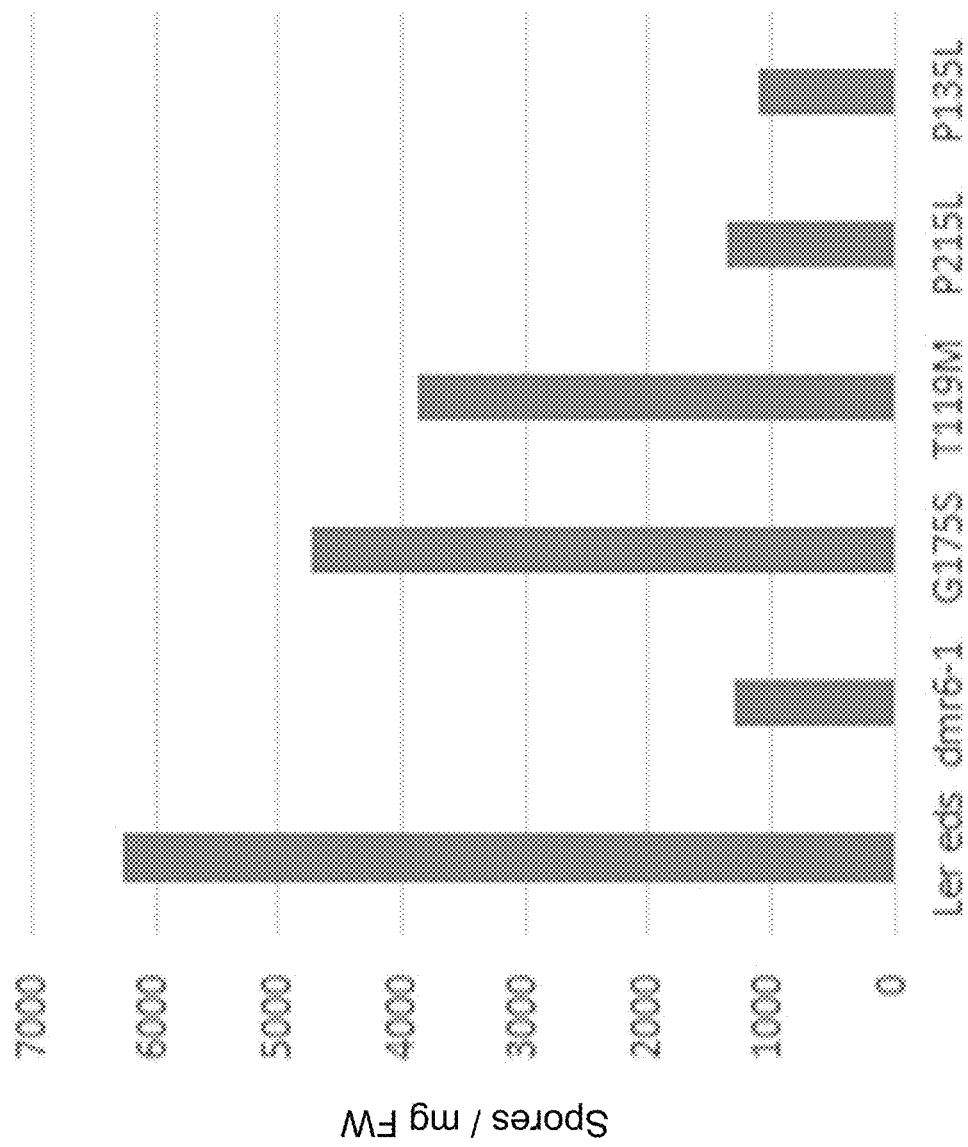
Figure 8:
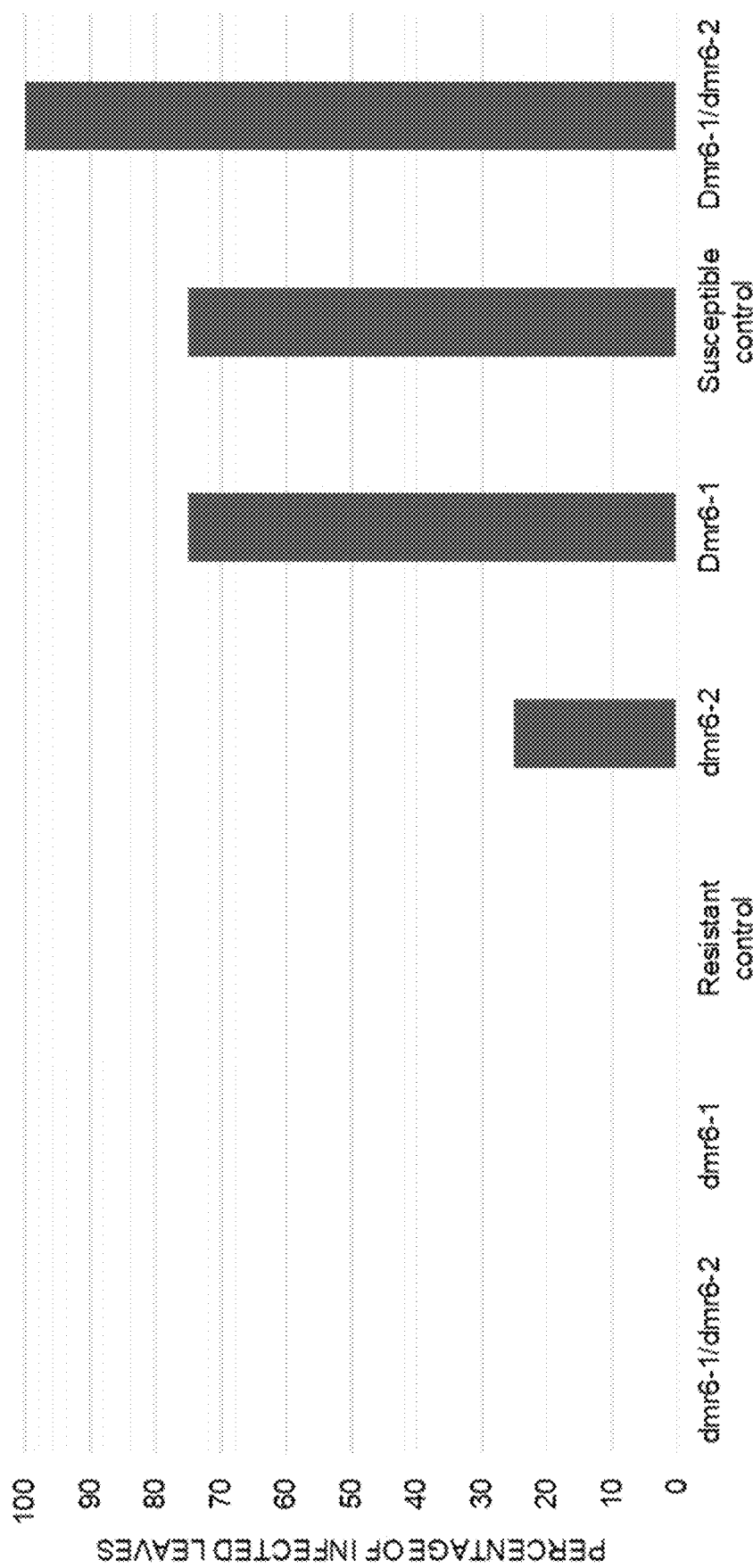
FIG. 8 shows the percentage of fourth leaves showing *P. capsici* symptoms 13 days post inoculation in plants of the following *C. annuum* lines: 'dmr6-1/dmr6-2', 'dmr6-1', 'Ranger' (Resistant control), 'dmr6-2', 'Dmr6-1', 'OP177' (Susceptible control), and 'Dmr6-1/dmr6-2'.
Figure 9:
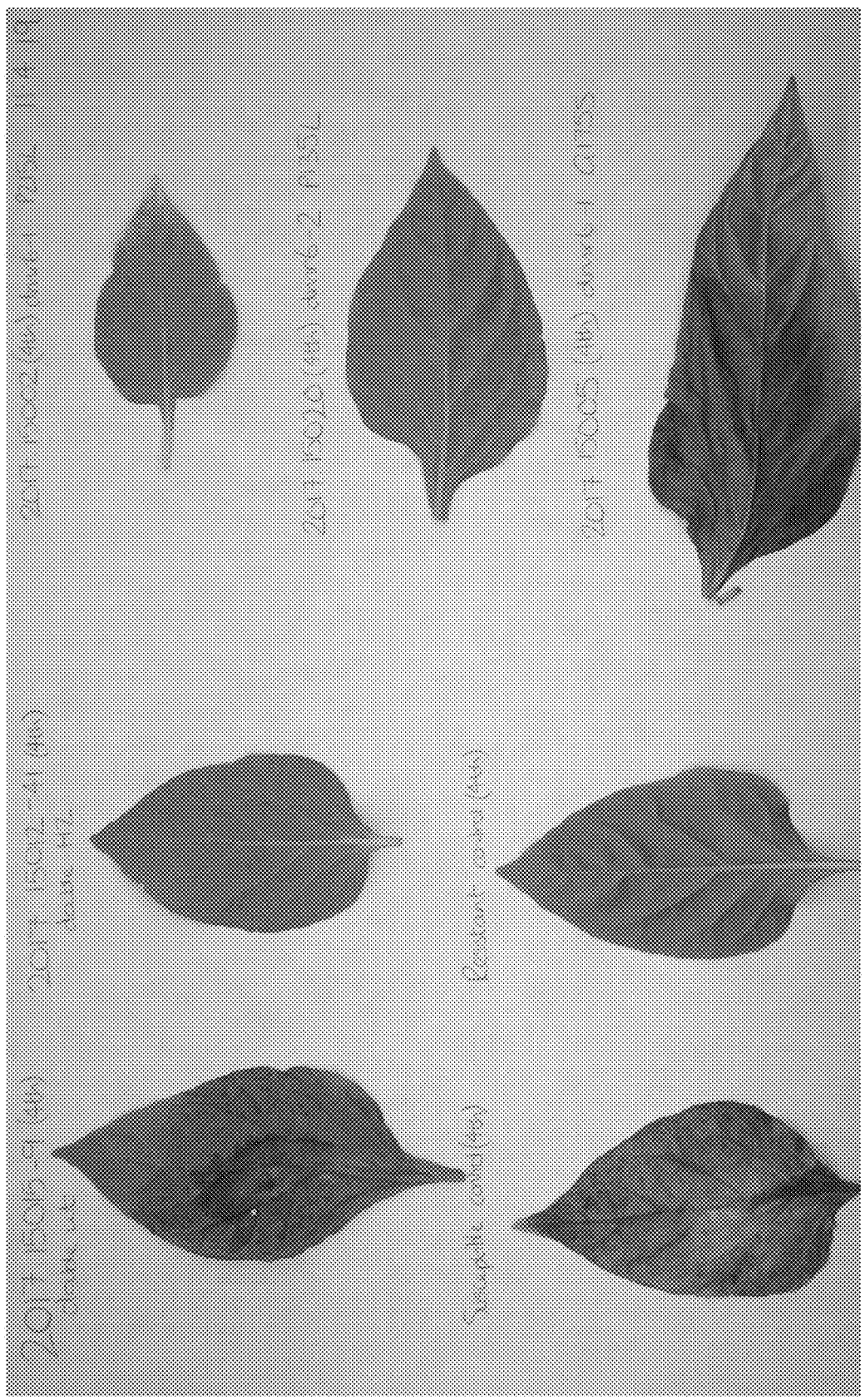
FIG. 9 shows representative images of the fourth leaf from the following *C. annuum* lines: wild type segregant plants from the cross that produced the 'dmr6-1/dmr6-2 WT' line (wild type segregant plants from the cross that produced the 'dmr6-1/dmr6-2' line, top left, labeled "double wt"), 'OP177' (bottom left, labeled "Susceptible control"), 'dmr6-1/dmr6-2' (top middle, labeled "double HZ"), 'Ranger' (bottom middle, labeled "Resistant control"), 'dmr6-1' (top right), 'dmr6-2' (middle right), or 'Dmr6-1' (bottom right, labeled "dmr6-1 G175S"). Images were taken 13 days after inoculation with *P. capsici* isolate Q108.
Figure 10:
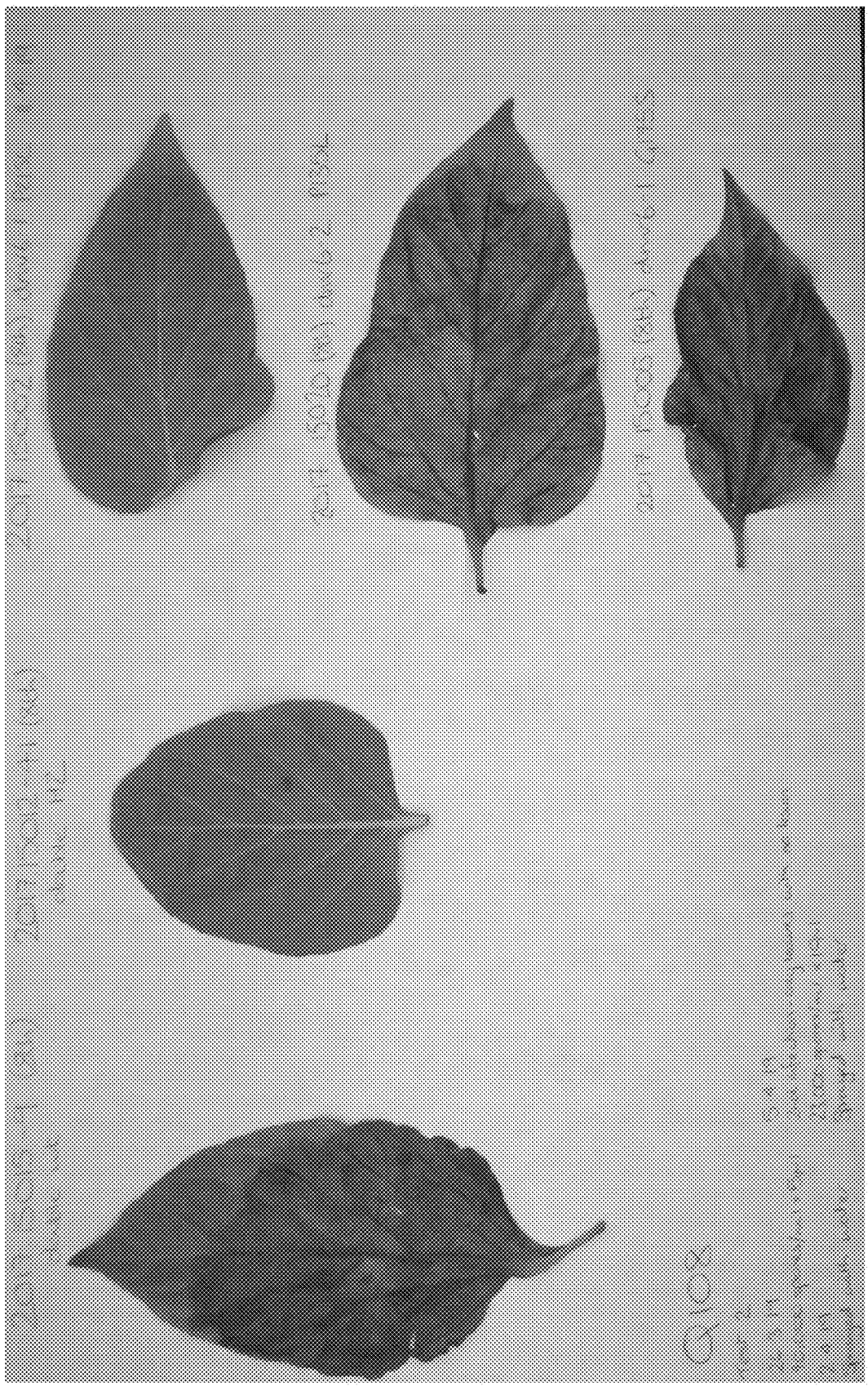
FIG. 10 shows representative images of the eighth leaf from the following *C. annuum* lines: 'dmr6-1/dmr6-2 WT' line (left, labeled "double wt"), 'dmr6-1/dmr6-2' (middle, labeled "double HZ"), 'dmr6-1' (top right), 'dmr6-2' (middle right), or 'Dmr6-1' (bottom right, labeled "dmr6-1 G175S"). Images were taken 13 days after inoculation with *P. capsici* isolate Q108.

Table 1 shows that the SEQ ID NO: 11 and 12 overexpressing plants were susceptible to P. infestans isolate US11. The silenced plant provided significant higher scores (more resistance) than the susceptible control OT9. For example, plant 556-01-08 had an average score of 8.5. As shown in FIG. 5 in box G10, plant 556-01-08 was not infected, which was similar to resistant control plant LA1296 (FIG. 5 box D8). Accordingly, silencing of both SEQ ID NO: 11 and 12 provided resistance to P. infestans.

P. Infestans and P. Capsici Assays in N. Benthamiana

N. benthamiana plants were silenced for DMR6 and subsequently drop-inoculated with a spore solution of P. infestans. DMR6 silencing clearly resulted in less colonization by the pathogen compared to the empty vector control or wild type non-silenced plants.

The P. capsici infection assay was done 8 days after Agro-infiltration of the DMR6 silencing construct. Table 2 shows results from the infection assay of the first VIGS experiment. The first VIGS showed low infection rates of the P. capsici after 7 days (Table 2).

TABLE 2

|  | Infected | Not infected | Total | % Infected |
|---|---|---|---|---|
| DMR6 silenced | 0 | 11 | 11 | 0% |
| Not silenced | 3 | 4 | 7 | 43% |

No DMR6 silenced leaves showed infection. 3 out of 7 non-silenced leaves showed infection. Ideally, 100% of non-silenced leaves would show infection. The low sporulation of non-silenced leaves was thought to be the cause of the low infection of the N. benthamiana leaves. However, none of the DMR6 silenced leaves showed infection symptoms, whereas 40% of the non-silenced leaves showed infection. To increase infection rate, changes were made in the acquirement of spores and the infection method, causing more aggressive infection during the second infection assay. In the second infection assay, one DMR6 silenced leaf was not infected, other DMR6 silenced leaves showed delayed infection and slower spreading of infection.

Conclusion

Potato with its two DMR6 orthologs silenced by RNAi showed decreased P. infestans susceptibility. Petunia with its two DMR6 orthologs mutated by transposon insertion showed decreased P. nicotianae susceptibility. Tomato expressing silencing constructs of its two DMR6 orthologs showed decreased P. infestans susceptibility, while tomato overexpressing its two DMR6 orthologs showed increased susceptibility to P. infestans. N. benthamiana with its DMR6 ortholog silenced by VIGS showed decreased susceptibility to P. infestans and P. capsici.

Example 2

Introduction

In this example, we functionally analyzed the A. thaliana DMR6 oxygenase and the related DMR6-LIKE OXYGENASES (DLO) 1 and 2. Overexpression of DMR6, DLO1, and DLO2 increased disease susceptibility indicating the three proteins can act as a negative regulator of immunity. DLO1, but not DLO2, is highly co-regulated with DMR6, however they differ in their spatial expression during downy mildew-infection. The dmr6-3_dlo1 double mutant was found to be completely resistant to H. arabidopsidis and showed a strongly reduced growth associated with high levels of salicylic acid.

Results

Overexpression of DMR6 Results in Enhanced Susceptibility to (Hemi-)biotrophic Pathogens Seedlings of the A. thaliana dmr6-1 mutant were previously described to be more resistant to H. arabidopsidis, but not to Pseudomonas syringae (hereinafter "P. syringae"). When tested on adult A. thaliana dmr6-1 mutant plants, however, strong resistance to P. syringae DC3000 was observed. Also adult A. thaliana dmr6-1 plants were more resistant to the obligate biotroph H. arabidopsidis compared to seedlings. In addition, strong resistance to the hemi-biotrophic oomycete P. capsici was evident in A. thaliana dmr6-1 mutant plants when compared to the parental line Ler eds1-2; whereas all A. thaliana dmr6-1 mutant plants survived, P. capsici destroyed the vast majority of plants of the parental line and complemented A. thaliana dmr6-1 mutant. The resistance of the A. thaliana dmr6-1 mutant to different (hemi-)biotrophs suggests that in wild-type A. thaliana plants DMR6 negatively regulates immunity to these pathogens.

To study this, the DMR6 coding sequence was expressed from the constitutive 35S promoter in transgenic Col-0 lines. The A. thaliana DMR6-overexpression lines showed a clear increase in disease susceptibility to H. arabidopsidis and P. syringae. The level of H. arabidopsidis sporulation, which is a measure of downy mildew infection, was doubled in A. thaliana DMR6-overexpression lines compared to the control. Also the development of disease-associated chlorosis was more pronounced in *A. thaliana* DMR6-overexpression lines than in non-transgenic Col-0 plants.

The increased susceptibility of six-week old plants to *P. syringae* bacteria was also clearly visible. While the control line (Col-0) showed a relatively low level of chlorosis and lesions at 3 days post inoculation, the *A. thaliana* DMR6-overexpression line showed more severe disease symptoms, i.e. more chlorosis and more and larger lesions. The increased susceptibility of DMR6-overexpressors to *P. syringae* infection was confirmed by bacterial growth assays that showed increased bacterial titers at 1 and 3 days post inoculation compared to the Col-0 control. Furthermore, expression of the defense marker genes PR-1, PR-2, and PR-5 in uninfected leaf tissue was reduced by 50 to 80% in the *A. thaliana* DMR6-overexpression line compared to wild type Col-0 plants that already have a very low level of expression. The reduced immunity of the *A. thaliana* DMR6-overexpression line, together with the enhanced resistance of the drm6-1 mutant, strongly supports the role of DMR6 as a negative regulator of immunity.

DMR6 and DMR6-LIKE OXYGENASEs Represent Separate Branches of a Distinct Clade in Flowering Plants The *A. thaliana* genome contains more than 150 2OG oxygenase genes some of which are similar to DMR6. To analyze the evolutionary conservation of DMR6 and related oxygenases in flowering plants we phylogenetically analyzed the family of 2OG oxygenases that contain the 2OG-Fe(II) oxygenase superfamily Pfam domain PF03171. From *A. thaliana* and eighteen flowering plants, of which genome sequences and protein models were available in the Phytozome v7.0 database (www.Phytozome.net), a total of 2951 proteins containing the PF03171 domain were selected using the HMMER3 algorithm. To filter small protein fragments and remove very large proteins, we only included proteins that did not exceed a 20% length difference to DMR6. Furthermore, only proteins that have less than 20% length difference of the oxidoreductase domain compared to DMR6 were retained. This resulted in a selection of 2038 proteins that fulfil all criteria, including 110 of 151 predicted *A. thaliana* 2OG oxygenases. Phylogenetic clustering resulted in a tree in which many distinct clades representing different enzyme activities are shown. Well-characterized oxygenases include flavonone-3-hydroxylase (F3H), 1-aminocyclopropane-1-carboxylic acid (ACC) oxidase, and anthocyanidin synthase (ANS) which are present in distinct clades different from the DMR6 clade. Two separate branches can be distinguished in the DMR6 clade that each contain 2OG oxygenases from dicots and monocots indicating that these subclades were already present in the ancestor of all flowering plants or earlier (82% bootstrap confidence). Gene duplications in the DMR6 clade are frequent in monocots in the upper part of the tree and in soybean and grapevine in both branches of the DMR6 clade. In the lower subclade, two *A. thaliana* DMR6 homologues cluster together with two proteins from *Arabidopsis lyrata* suggesting they are the result of a relatively recent gene duplication in the common ancestor of these two species.

These *A. thaliana* proteins are now designated DMR6-LIKE OXYGENASE or DLO (with gene At4g10500 encoding DLO1 and At4g10490 encoding DLO2). Also the DLO subclade shows a clear separation of the monocot and dicot proteins suggesting that the ancestor of all flowering plants already possessed a DLO besides DMR6. Grouping closely to DMR6, the DLOs form an interesting group that was subsequently analyzed in more detail, focusing on the *A. thaliana* DLO1 and DLO2 genes.

Overexpression of DLO1 and DLO2 Complements the dmr6 Mutant

The DLOs could have the same biological activity as DMR6 and were, therefore, tested for complementation of the *A. thaliana* dmr6-1 mutant. To this end, DLO1 and DLO2 were expressed under the constitutive 35S promoter and transformed into the *A. thaliana* dmr6-1 mutant background. Four independent T3 lines, transformed with 35S:DLO1 or 35S:DLO2, were analyzed for their expression level and 3 lines per construct were selected that showed clear transgene expression. To check for complementation, 2-week old plants were infected with *H. arabidopsidis* isolate Cala2 and at 5 days post inoculation (dpi) the number of spores per mg seedlings was scored as measure of susceptibility.

Intriguingly, while *A. thaliana* dmr6-1 mutant showed clear resistance, the 35S::DLO1 and 35S::DLO2 plants were highly susceptible, similar to or higher than Ler eds1-2 that is the parental line of the *A. thaliana* dmr6-1 mutant. As both DLO1 and DLO2 can complement the *A. thaliana* dmr6-1 mutant phenotype, we conclude that the DLOs have a function similar to that of DMR6.

As overexpression of DMR6 in the Col-0 background results in enhanced susceptibility to downy mildew and other pathogens, we next investigated if overexpressing DLO1 and DLO2 would also make Col-0 more susceptible. *A. thaliana* transformants expressing the 35S:DLO1 and 35S:DLO2 transgenes were selected. Col-0 overexpressing DMR6 and the highly susceptible Col eds1-2 mutant were included as controls. Disease assays with *H. arabidopsidis* showed that overexpression of DLO1 and DLO2 enhanced susceptibility compared to the Col-0 parental line as shown by the higher level of sporulation. The observed enhanced susceptibility was comparable to the Col-0 plants overexpressing DMR6 and the Col eds1-2 mutant. This confirms that the DLO1 and DLO2 protein have an activity similar or identical to DMR6 resulting in the same phenotypic effects.

Expression of DLO1, but not DLO2, is Immunity-related

The DLO1 and DLO2 complementation and overexpression lines were all generated using the 35S promoter. It is, however, likely that the expression of the wild-type DLOs is highly regulated similar to that of DMR6, which is strongly activated during plant defense. Therefore, we analyzed publicly available gene expression data to determine if DLO1 and DLO2 show immunity-related expression similar to DMR6. For this analysis, data of 9 different Affymetrix microarray experiments, all dealing with transcriptional profiling after pathogen attack, defense related hormone application and elicitor/effector treatment, were used.

The expression analysis was focused on 30 2OG oxygenases that belong to the large clade containing the DLOs and DMR6. Hierarchical clustering of the genes allowed grouping of the 2OG oxygenase genes according to their expression patterns, providing information about which genes are co-regulated during plant immune responses. Strikingly, DLO1 clusters with DMR6, whereas DLO2 does not show any co-regulation with DMR6 or DLO1. DMR6 and DLO1 are both activated after infection with the downy mildew *H. arabidopsidis*, the powdery mildew *Erysiphe orontii*, and the bacterium *P. syringae* and as well as SA treatment. DLO2 clusters well away from DMR6 and DLO1 and appears to be unresponsive in the different experiments. Further analysis of available microarray data using Genevestigator revealed that DLO2 is not expressed in response to any treatment or in any tissue, except for siliques, suggesting that DLO2 does not have a role in immunity of the vegetative plant tissues.

The responsiveness of the DLOs to *H. arabidopsidis* infection was experimentally verified by quantitative PCR (qPCR). DMR6 and DLO1 are highly activated in plants infected with a compatible or incompatible isolate of *H. arabidopsidis*. Also following treatment with the SA mimic BTH, both DMR6 and DLO1 are strongly activated. In contrast, DMR6 and DLO1 are unresponsive to methyl jasmonate (MeJA), which is known to activate jasmonic acid-induced genes. DLO2 expression is undetectable (cT values higher than 35) in the different experimental conditions confirming the Genevestigator data. The fact that both DMR6 and DLO1 are activated during the plant's immune response suggests that in leaves of wild-type plants DLO1 also acts as a negative regulator of defense. However, the question remains why the dmr6 mutants have such a clear resistance phenotype in the presence of an intact DLO1 gene that could take over DMR6 function?

DLO1 and DMR6 Show Different Spatial Expression in Infected Leaves

To analyze the tissue-specific expression of DLO1 during downy mildew infection, we generated transgenic lines containing a construct with the DLO1 promoter fused to the GUS reporter gene ($pro_{DLO1}$:GUS). Since we did not observe any expression of DLO2, no GUS fusion with the promoter of DLO2 was constructed. Following *H. arabidopsidis* infection, DMR6 spatial expression was specifically detected to the sites that are in direct contact with the pathogen as has been described previously. In contrast, DLO1 expression was not induced in cells that are in close contact with the pathogen but only in or around the main veins of infected cotyledons and leaves. Interestingly, DLO1 expression was observed only in areas of the leaf that are close to *H. arabidopsidis* infection sites, indicating that the activation of DLO1 depends on the presence of the pathogen. The absence of DLO1 activity in haustoria-containing cells could explain why DLO1 cannot fully complement for loss of DMR6 activity in the dmr6 mutants. Whereas these data show distinct activities of the DMR6 and DLO1 genes, the extent of redundancy of these genes is unclear and was therefore further studied genetically.

DLO1 Function is Partially Redundant with DMR6

Redundancy analysis in mutant lines is best performed in the same genetic background. We, therefore, obtained mutants in the Col-0 background for DMR6 (GABI-KAT line GK-249H03.01, designated mutant dmr6-3) and DLO1 (SALK line 059907, named dlo1). dmr6-3_dlo1 double mutants were generated and phenotypically analyzed together with the dmr6-3 and dlo1 single mutants, as well as with the parental Col-0 line. The level of susceptibility to *H. arabidopsidis* Waco9 was strongly reduced in the dmr6-3 mutant, but only slightly reduced in the dlo1 mutant. Combining the two mutations in the dmr6-3_dlo1 double mutant resulted in plants that showed complete resistance to *H. arabidopsidis*.

We next tested the level of defense gene expression in the mutants, as previous research on the *A. thaliana* dmr6-1 and *A. thaliana* dmr6-2 mutants showed increased levels of expression of PR-1 and other defense genes. Also the dmr6-3 mutant showed elevated expression of PR-1, PR-2 and PR-5, confirming previous results. The dlo1 mutant only showed no significant induction of expression of the three PR genes.

In contrast, the dmr6-3_dlo1 double mutant showed extremely high levels of defense gene expression. PR-1 transcripts were more than 30,000-fold higher in more the dmr6-3_dlo1 mutant than in Col-0, and a more than 100-fold higher than in the dmr6-3 single mutant. In the tested mutants there was a clear correlation between the level of resistance to downy mildew and increase in defense gene expression, suggesting that resistance is caused by activation of plant immune responses. Our data shows that the dlo1 mutation enhances the immunity of the dmr6-3 single mutant, indicating DLO1 and DMR6 act partially redundant.

This was further corroborated by the growth phenotype of the mutants. Plants grown for 5.5 weeks under short day conditions showed striking differences between the genotypes. Whereas the dlo1 mutant grows similar to Col-0, and the dmr6-3 mutant only shows a slight growth reduction, the dmr6-3_dlo1 double mutant displayed strong growth reduction resulting in dwarfed plants. The growth reduction and level of resistance to downy mildew are correlated in the tested mutants, suggesting these two phenotypes are functionally linked.

It is well known that strong activation of plant immunity can be accompanied by severe growth reduction, which in many cases can be linked to high SA levels. Indeed, levels of SA were more than 200 times higher in the dmr6-3_dlo1 double mutant than in the Col-0 control, and ~20 times higher than in the dmr6-3 mutant. The single mutant dmr6-3 showed a modest ~10 fold increase in SA compared to the Col-0 control, whereas the dlo1 mutant did not accumulate more SA than Col-0.

To test if the high SA level in dmr6-3_dlo1 is the cause of the dwarf phenotype and high level of resistance to downy mildew, the double mutant was crossed to the sid2 mutant, which is strongly compromised in SA biosynthesis as a result of loss of isochorismate synthase 1. The triple mutant dmr6-3_dlo1_sid2 showed almost complete recovery of the growth phenotype of the dmr6-3_dlo1 double mutant, although it remained slightly smaller than the sid2 mutant. Disease assays showed that also the high level of resistance of the dmr6-3_dlo1 double mutant and dmr6-3 single mutant was strongly reduced in the absence of SID2. Because of the low SA level, the sid2 mutant is more susceptible to *H. arabidopsidis* than the wild type Col-0. The level of susceptibility to *H. arabidopsidis* correlates well to the level of total SA in the mutants. Both dmr6 as well as the dmr6-3_dlo1 double mutant show no sporulation at 5 dpi and have the highest SA levels. The triple mutant dmr6-3_dlo1_sid2 still produces more SA than Col-0, which might explain it lower susceptibility to downy mildew.

It was concluded that both the resistance to *H. arabidopsidis*, as well as the growth reduction of the dmr6-3_dlo1 mutant is the result of increased SA levels. The extreme phenotypes of the double mutant demonstrate that the DLO1 and DMR6 genes act redundantly. However, the dmr6 single mutant is more resistant to downy mildew than the dlo1 mutant. Together with the observed different localization of expression of the DMR6 and DLO1 genes, the present data indicate that the DMR6 and DLO1 genes have distinct but partially redundant functions as negative regulators of plant immunity.

Example 3

Introduction

This example demonstrates the identification of DMR6 orthologs in *C. annuum* and their function in *P. capsici* resistance. Mutation of *C. annuum* DMR6 orthologs were generated by EMS mutation and their function were analyzed by complementation of *A. thaliana* dmr6-1 mutant, as well as leaf and whole plant downy mildew tests.

Materials and Methods
Identification of DMR6 Orthologs in C. Annuum

C. annuum DMR6 genes were identified on basis of BlastX searches as reciprocal best hit to Arabidopsis thaliana or other plant DMR6 protein sequences. A candidate orthologous DMR6 sequence of C. annuum was identified as the best hit from DNA databases when searching with the Arabidopsis DMR6 protein or DNA sequence, or that of another plant species, using a Blast program. The obtained candidate orthologous nucleotide sequence of C. annuum was then used to search for homology to all Arabidopsis proteins present in the DNA databases (e.g. at NCBI or TAIR) using the BlastX search method. If the best hit and score was to the Arabidopsis DMR6 protein, the given DNA sequence was identified as being an ortholog, or orthologous sequence.

Two C. annuum DMR6 genes were identified, and named CaDMR6-1 and CaDMR6-2. SEQ ID NO: 16 corresponds to the amino acid sequence of CaDMR6-1, and SEQ ID NO: 20 corresponds to the gene sequence of CaDMR6-1. SEQ ID NO: 17 corresponds to the amino acid sequence of CaDMR6-2, and SEQ ID NO: 21 corresponds to the gene sequence of CaDMR6-2. Position 215 in CaDMR6-1 is conserved across all DMR6 proteins analyzed, which suggests this amino acid is essential to DMR6 function. In addition, there is an essential iron binding residue at position D214, just next to P215. Position P135 in CaDMR6-2 is conserved across all oxygenases (not just DMR6), strongly suggesting that the amino acid at this position is essential for oxygenase function.

Cloning of CaDMR6-1 and CaDMR6-2 and Production of A. Thaliana dmr6-1 Mutant Complementation Lines The coding sequence of CaDMR6-1 and CaDMR6-2 were synthesized and cloned into a pCR8™/GW/TOPO (ThermoFisher) using standard protocol. The commercially available M13 primers were used for PCR and sequencing in the pCR8™/GW/TOPO. Then, CaDMR6-1 or CaDMR6-2 genes were shuttled from the entry vector into the binary destination vector pK7WG2 using LR Clonase™ II (Thermo Fisher). The commercially available 35S promoter and terminator primers were used for sequencing the pK7WG2 plasmid. pK7WG2 vectors containing the correct CaDMR6-1 or CaDMR6-2 sequences were transformed into Agrobacterium tumefaciens strain GV3101.

A. thaliana dmr6-1 mutant complementation lines were produced by transforming A. thaliana dmr6-1 mutant plants with the Agrobacterium tumefaciens containing pK7WG2 vector containing CaDMR6-1 or CaDMR6-2 under the control of the 35S promoter using the floral dip method.

Complementation of the A. thaliana dmr6-1 Mutant with CaDMR6-1 and CaDMR6-2

As described in Example 2, the A. thaliana DMR6 gene functions as a negative regulator of immunity. In order to test whether the C. annuum orthologs CaDMR6-1 and CaDMR6-2 had the same biological activity as A. thaliana DMR6, they were tested for complementation of the A. thaliana dmr6-1 mutant.

In order to test the disease resistance phenotype, plants of the A. thaliana dmr6-1 complementation lines were infected with Hyaloperonospora arabidopsidis. Hyaloperonospora arabidopsidis Cala2 inoculum ($4 \times 10^4$ spores/mL) was applied on 14-day-old seedlings using a spray gun. After inoculation, plants were allowed to dry for ~30 min and were subsequently incubated under a sealed lid (100% relative humidity) in a growth chamber at 16° C. with 9 h light/day (100 µE/m2/s). The amount of sporulation was quantified at 5 to 6 d after inoculation by counting the number of conidiophores on the cotyledons and leaves.

EMS Mutagenesis Screens of C. Annuum

EMS mutagenesis screens were performed in order to obtain C. annuum plants with single mutations in CaDMR6-1 or CaDMR6-2. Briefly, seeds of C. annuum were treated with mutagen in order to introduce random point mutations in the genome. Mutated plants were grown to produce seeds and the next generation was screened for mutations in CaDMR6-1 or CaDMR6-2. This was achieved by monitoring the level of CaDMR6-1 or CaDMR6-2 gene expression, or by searching for nucleotide changes (mutations) by the TILLING method, by DNA sequencing, or by any other known method to identify nucleotide changes. The plants were then made homozygous by selfing or intercrossing under molecular marker selection, and homozygous plants were selected for further analysis.

From these screens, CaDMR6-1 single mutant plants with mutations in conserved regions with predicted effect on the protein function were identified. In addition, CaDMR6-2 single mutant plants with mutations in conserved regions with predicted effect on the protein function were identified.

Three CaDMR6-1 mutant alleles and one CaDMR6-2 mutant allele were selected for further testing (Table 3). These alleles were named CaDMR6-1 P215L (SEQ ID NO: 29, wherein the modification in SEQ ID NO: 29 is at the SNP, and the encoded protein is SEQ ID NO: 25), CaDMR6-1 G175S (SEQ ID NO: 30, wherein the modification in SEQ ID NO: 30 is at the SNP, and the encoded protein is SEQ ID NO: 26), CaDMR6-1 T119M (SEQ ID NO: 31, wherein the modification in SEQ ID NO: 31 is at the SNP, and the encoded protein is SEQ ID NO: 27), and CaDMR6-2 P135L (SEQ ID NO: 32, wherein the modification in SEQ ID NO: 32 is at the SNP, and the encoded protein is SEQ ID NO: 28) for the positions of the amino acid changes. As noted above, position 215 in CaDMR6-1 is conserved across all DMR6 proteins analyzed, which suggests this amino acid is essential to DMR6 function. Similarly, position P135 in CaDMR6-2 is conserved across all oxygenases (not just DMR6), strongly suggesting that the amino acid at this position is essential for oxygenase function. Without wishing to be bound by theory, it was therefore thought that mutations in either of these amino acids would disrupt the standard function of a DMR6 gene (i.e., negative regulation of immunity).

TABLE 3

C. annuum mutant alleles.

| Allele | CDS Sequence | CDS Position | Nucleotide Change | Amino Acid Sequence | Amino Acid Change |
|---|---|---|---|---|---|
| CaDMR6-1 P215L | SEQ ID NO: 29 | 644 | C to T | SEQ ID NO: 25 | P to L |
| CaDMR6-1 G175S | SEQ ID NO: 30 | 523 | G to A | SEQ ID NO: 26 | G to S |
| CaDMR6-1 T119M | SEQ ID NO: 31 | 356 | C to T | SEQ ID NO: 27 | T to M |
| CaDMR6-2 P135L | SEQ ID NO: 32 | 404 | C to T | SEQ ID NO: 28 | P to L |

Complementation of the A. Thaliana dmr6-1 Mutant with Mutant CaDMR6-1 and mutant CaDMR6-2 Alleles The mutant alleles CaDMR6-1 P215L, CaDMR6-1 G175S, CaDMR6-1 T119M, and CaDMR6-2 P135L were tested in A. thaliana complementation assays, which were performed as described above.

Generation of Single and Double DMR6 Mutant *C. Annuum* Lines

In order to test the effect of the mutant alleles on resistance in *C. annuum*, single and double mutant *C. annuum* lines containing three of the alleles described above were generated (Table 4).

TABLE 4

*C. annuum* lines containing different mutant alleles.

| *C. annuum* line | *C. annuum* line description | DMR6 mutant alleles in *C. annuum* line |
|---|---|---|
| 'dmr6-1/dmr6-2' | CaDMR6-1/CaDMR6-2 double mutant; resulting from cross of CaDMR6-1 P215L single mutant plants with CaDMR6-2 P135L single mutant plants; homozygous. | CaDMR6-1 P215L and CaDMR6-2 P135L |
| 'dmr6-1' | CaDMR6-1 P215L single mutant; M4 generation. | CaDMR6-1 P215L |
| 'Ranger' | Resistant control; a *C. annuum* cultivar resistant to *P. capsici*. | None |
| 'dmr6-2' | CaDMR6-2 P135L single mutant; M4 generation. | CaDMR6-2 P135L |
| 'Dmr6-1' | CaDMR6-1 G175S single mutant (dose not provide resistance); M4 generation. | CaDMR6-1 G175S |
| 'OP177' | Susceptible control; a *C. annuum* line susceptible to *P. capsici*. | None |
| 'Dmr6-1/dmr6-2' | CaDMR6-1/CaDMR6-2 double mutant; resulting from cross of CaDMR6-1 G175S single mutant plants with CaDMR6-2 P135L single mutant plants; homozygous. | CaDMR6-1 G175S and CaDMR6-2 P135L |
| 'dmr6-1/dmr6-2 WT' | Wild type segregant plants from the cross that produced the 'dmr6-1/dmr6-2' line. | None |

Genotyping of Mutant *C. Annuum* Lines

Plants were genotyped by PCR and High-Resolution Melting Curve (HRM) using primers and probes designed to identify the mutant alleles listed in Table 3. The coding sequence of the CaDMR6-1 P215L mutant allele is SEQ ID NO: 29, wherein the modification in SEQ ID NO: 29 is at the SNP; the coding sequence of the CaDMR6-1 G175S mutant allele is SEQ ID NO: 30, wherein the modification in SEQ ID NO: 30 is at the SNP; the coding sequence of the CaDMR6-1 T119M mutant allele is SEQ ID NO: 31, wherein the modification in SEQ ID NO: 31 is at the SNP; and the coding sequence of the CaDMR6-2 P135L mutant allele is SEQ ID NO: 32, wherein the modification in SEQ ID NO: 32 is at the SNP. HRM was used to determine homozygosity of the plants.

Leaf Downy Mildew Test

For the leaf assay, the *C. annuum* lines containing mutant alleles (Table 3) were tested by inoculating *P. capsici* isolate Q108 on leaves. The fourth leaf was removed from each plant and placed on wet filter paper in a tray with a glass lid. 5 μl inoculum (40,000 spores/ml) of *P. capsici* isolate Q108 was pipetted onto the underside of each leaf (drop inoculation). Trays were kept in a climate cell at 20° C. with 16 hours light. The leaves were misted with tap water periodically. At 13 dpi, the percentage of infected leaves was calculated. The percentage of infected leaves was obtained by counting the number of leaves showing disease symptoms 13 dpi, and then dividing that number by the total number of leaves infected.

Whole Plant Downy Mildew Test

For the whole plant assay, the *C. annuum* lines 'dmr6-1', 'dmr6-2', 'dmr6-1/dmr6-2,' and resistant control (Table 3), as well as wild type segregant plants from the cross that produced the 'dmr6-1/dmr6-2 WT' plants were tested. The plants were misted with a solution of *P. capsici* isolate Q108 with a spore concentration of 40,000 spores ml$^{31\ 1}$ and kept in a tent at 100% relative humidity in the greenhouse. At 7 days post spray with *P. capsici*, the tent was opened and the number of lesions on each plant was counted.

Results

*A. Thaliana* Complementation Tests

As shown in FIG. 6, both CaDMR6-1 and CaDMR6-2 were functional DMR6 genes because they complemented the *A. thaliana* dmr6-1 mutant phenotype. Specifically, both CaDMR6-1 and CaDMR6-2 complemented the *A. thaliana* dmr6-1 mutant by restoring susceptibility to downy mildew to similar levels as the susceptible control line (Ler eds). As both CaDMR6-1 and CaDMR6-2 complemented the *A. thaliana* dmr6-1 mutant phenotype, it was concluded that CaDMR6-1 and CaDMR6-2 had a function similar to that of *A. thaliana* DMR6.

As shown in FIG. 7A, the mutant alleles CaDMR6-1 P215L and CaDMR6-2 P135L did not complement the *A. thaliana* dmr6-1 mutant phenotype. These mutant alleles did not complement the dmr6-1 mutant in *A. thaliana*, because the resistance to downy mildew seen in the dmr6-1 mutant was maintained (in contrast to the susceptible control Ler eds). As shown in FIG. 7B, the mutant alleles CaDMR6-1 G175S (hereafter referred to as 'Dmr6-1') and CaDMR6-1 T119M did complement the dmr6-1 mutant in *A. thaliana*, because the suppression of the immune response was restored, and thus the plants were susceptible to downy mildew. These results showed that both CaDMR6-1 P215L (hereafter referred to as 'dmr6-1') and CaDMR6-2 P135L (hereafter referred to as 'dmr6-2') were mutant alleles able to confer resistance in *A. thaliana*, and were comparable to the *A. thaliana* dmr6-1 mutant, while mutant alleles CaDMR6-1 G175S (hereafter referred to as 'Dmr6-1') and CaDMR6-1 T119M were unable to confer resistance in *A. thaliana.*

Leaf *Phytophthora Capsici* Tests in *C. Annuum*

As shown in FIG. 8, the 'dmr6-1/dmr6-2' line and the 'dmr6-1' line showed a high level of resistance as compared to the resistant control line. Further, the 'dmr6-2' line showed a reduced susceptibility as compared to the susceptible control line. Finally, the 'Dmr6-1' line and the 'Dmr6-1/dmr6-2' line were as susceptible as the susceptible control line.

FIG. 9 shows representative images of fourth leaves from a leaf assay conducted as described above that were taken at 13 dpi. The leaves from the 'dmr6-1/dmr6-2' (labeled "double HZ"), 'dmr6-1', and 'dmr6-2' plants, as well as the leaves from the resistant control plants, all did not have disease symptoms. In contrast, the leaves from 'Dmr6-1' plants (labeled "dmr6-1 G175S"), 'dmr6-1/dmr6-2 WT' line (labeled "double wt"), and the susceptible control, all showed disease symptoms.

FIG. 10 shows representative images of eighth leaves from a leaf assay conducted as described above that were taken at 13 days post spray with *P. capsici*. The leaves from the 'dmr6-1/dmr6-2' (labeled "double HZ") and 'dmr6-1' plants did not have disease symptoms. In contrast, the leaves from 'Dmr6-1' (labeled "dmr6-1 G175S"), and the leaves from 'dmr6-1/dmr6-2 WT' line (susceptible control; labeled "double wt"), showed disease symptoms. The leaf from the 'dmr6-2' plant also showed disease symptoms, unlike in the fourth leaf test.

Whole Plant *Phytophthora Capsici* Tests in *C. Annuum*

Figure 11:
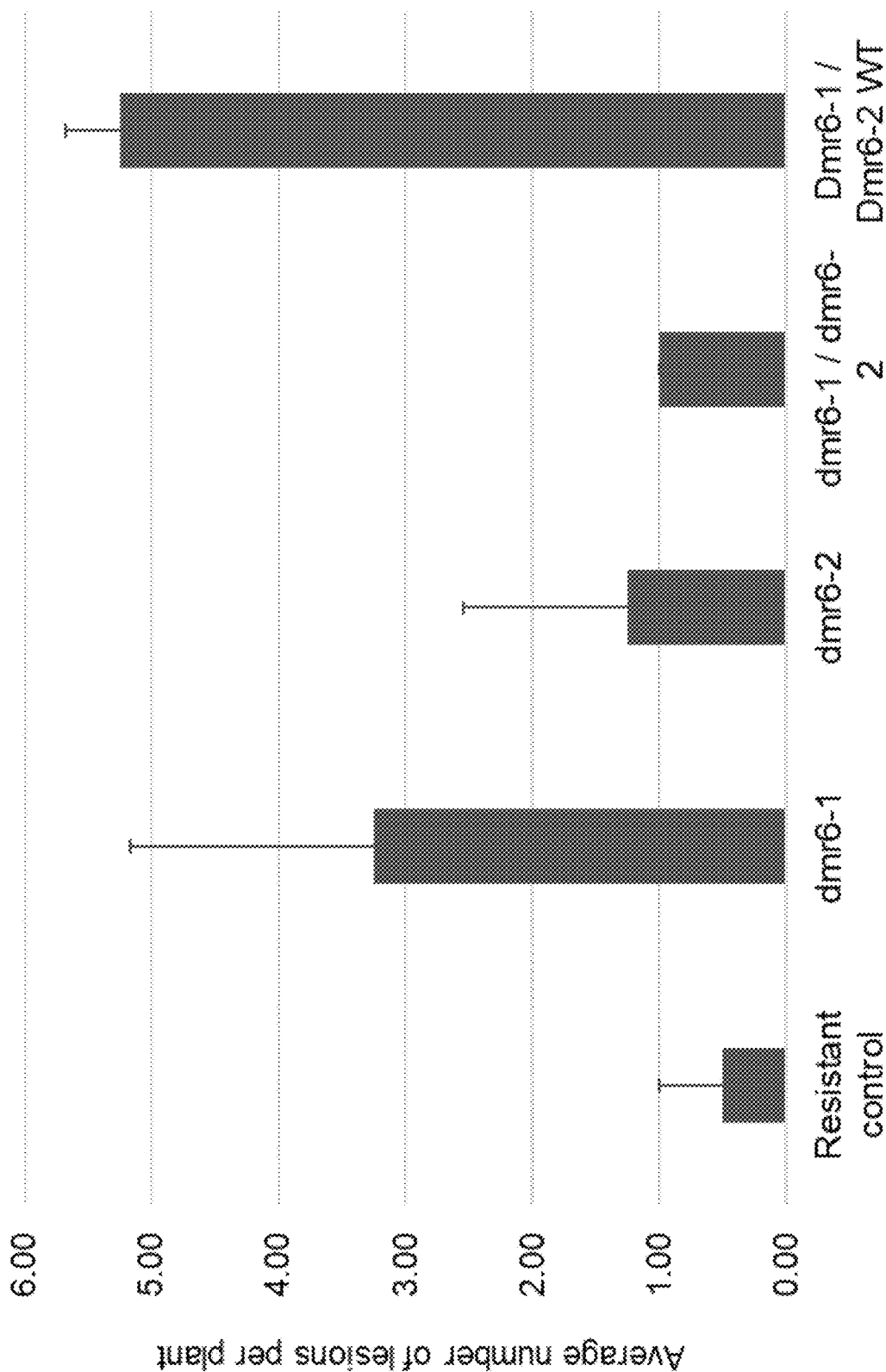
FIG. 11 shows the average number of lesions per plant 7 days post spray with *P. capsici* of the following *C. annuum* lines: 'Ranger' (resistant control), 'dmr6-1', 'dmr6-2', 'dmr6-1/dmr6-2', and 'dmr6-1/dmr6-2 WT' (labelled 'Dmr6-1/Dmr6-2 WT').
Figure 12B:
FIGS. 12A-12B show representative images of *C. annuum* plants taken 7 days post spray with *P. capsici*.
Figure 12A:
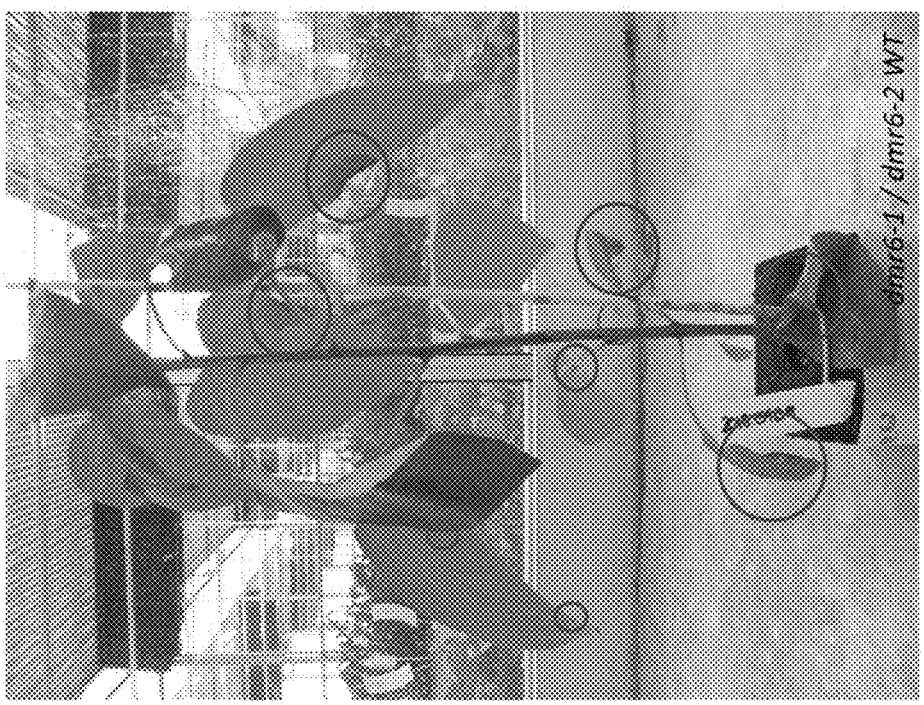

FIG. 11 shows the 'dmr6-1/dmr6-2' plants were as resistant as the res

```
            275                 280                 285
Cys Asp Ser Ala Lys Ile Ser Ala Pro Lys Leu Leu Thr Glu Asp Gly
    290                 295                 300

Ser Pro Val Ile Tyr Gln Asp Phe Thr Tyr Ala Glu Tyr Tyr Lys Lys
305                 310                 315                 320

Phe Trp Ser Arg Asn Leu Asp Gln Glu His Cys Leu Glu Leu Phe Lys
                325                 330                 335

Asn

<210> SEQ ID NO 2
<211> LENGTH: 342
<212> TYPE: PRT
<213> ORGANISM: Solanum tuberosum

<400> SEQUENCE: 2

Met Glu Thr Thr Ser Val Leu Ser Gly Gly Phe Asn His Ser Thr Leu
1               5                   10                  15

Pro Glu Ser Tyr Val Arg Pro Glu Ser Gln Arg Pro Arg Met Ser Glu
                20                  25                  30

Val Val Asp Arg Asp Asp Leu Val Pro Val Ile Asp Met Ser Cys Thr
            35                  40                  45

Asp Arg Asn Val Ile Val His Gln Ile Gly Glu Ala Cys Arg Leu Tyr
        50                  55                  60

Gly Phe Phe Gln Val Ile Asn His Gly Val Ser Lys Lys Val Met Asp
65                  70                  75                  80

Glu Met Leu Gly Val Ala His Glu Phe Phe Lys Leu Pro Val Glu Glu
                85                  90                  95

Lys Met Lys Leu Tyr Ser Asp Asp Pro Ser Lys Thr Met Arg Leu Ser
            100                 105                 110

Thr Ser Phe Asn Val Lys Lys Glu Thr Val His Asn Trp Arg Asp Tyr
        115                 120                 125

Leu Arg Leu His Cys Tyr Pro Leu Asp Lys Tyr Ala Pro Glu Trp Pro
    130                 135                 140

Ser Asn Pro Pro Ser Phe Arg Glu Ile Val Ser Lys Tyr Cys Met Glu
145                 150                 155                 160

Val Arg Gln Val Gly Tyr Arg Leu Glu Glu Ala Ile Ser Glu Ser Leu
                165                 170                 175

Gly Leu Glu Lys Asp Cys Ile Lys Asn Val Leu Gly Glu Gln Gly Gln
            180                 185                 190

His Met Ala Ile Asn Phe Tyr Pro Pro Cys Gln Pro Glu Leu Thr
        195                 200                 205

Tyr Gly Leu Pro Ala His Thr Asp Pro Asn Ala Ile Thr Ile Leu Leu
    210                 215                 220

Gln Asp Leu Gln Val Ala Gly Leu Gln Val Leu Lys Asp Gly Glu Trp
225                 230                 235                 240

Leu Ser Ile Lys Pro Gln Pro Asp Ala Phe Val Ile Asn Leu Gly Asp
                245                 250                 255

Gln Leu Glu Ala Leu Ser Asn Gly Lys Tyr Lys Ser Ile Trp His Arg
            260                 265                 270

Ala Ile Val Asn Ser Asp Lys Ala Arg Met Ser Val Ala Ser Phe Leu
        275                 280                 285

Cys Pro Asn Asp Cys Ser Ile Ile Ser Ala Pro Lys Thr Leu Ile Glu
    290                 295                 300

Asp Gly Ser Ser Ala Ile Tyr Arg Asp Phe Thr Tyr Thr Glu Tyr Tyr
```

```
305             310             315             320
Asp Lys Phe Trp Ser Arg Asn Leu Asp Gln Glu Tyr Cys Leu Glu Leu
                325                 330                 335

Phe Lys Asn Asp Gly Thr
            340

<210> SEQ ID NO 3
<211> LENGTH: 340
<212> TYPE: PRT
<213> ORGANISM: Unknown
<220> FEATURE:
<223> OTHER INFORMATION: Petunia

<400> SEQUENCE: 3

Met Glu Ser Asn Val Ile Ser Ser Gly Thr Lys Tyr Thr Asn Leu Pro
1               5                   10                  15

Lys Ser Tyr Val Arg Pro Glu Ser Gln Arg Pro Arg Leu Ser Glu Val
                20                  25                  30

Asp Asp Cys Gln Asp Asn Ile Pro Val Ile Asp Leu Cys Cys Arg Asp
            35                  40                  45

Asn Asn Val Ile Ile Gln Gln Ile Glu Glu Ala Cys Arg Leu Tyr Gly
50                  55                  60

Phe Phe Gln Val Ile Asn His Gly Val Pro Lys Lys Leu Ile Glu Glu
65                  70                  75                  80

Met Leu Gly Val Ala His Glu Phe Phe Lys Leu Pro Val Glu Glu Lys
                85                  90                  95

Met Lys Leu Tyr Ser Asp Asp Pro Ser Lys Thr Met Arg Leu Ser Thr
                100                 105                 110

Ser Phe Asn Val Lys Lys Glu Thr Val His Asn Trp Arg Asp Tyr Leu
            115                 120                 125

Arg Leu His Cys Tyr Pro Leu Glu Lys Tyr Ala Pro Glu Trp Pro Ser
130                 135                 140

Thr Pro Ser Ser Phe Arg Glu Ile Val Ser Arg Tyr Cys Ile Glu Val
145                 150                 155                 160

Arg Gln Leu Gly Tyr Arg Leu Gln Glu Ala Ile Ser Glu Ser Leu Gly
                165                 170                 175

Leu Glu Lys Asp Cys Ile Lys Asn Ile Leu Gly Glu Gln Gly Gln His
            180                 185                 190

Met Ala Val Asn Tyr Tyr Pro Pro Cys Pro Glu Pro Glu Leu Thr Tyr
            195                 200                 205

Gly Leu Pro Ala His Thr Asp Pro Asn Ala Leu Thr Ile Leu Leu Gln
210                 215                 220

Asp Leu Gln Val Ala Gly Leu Gln Val Leu Lys Asp Gly Lys Trp Leu
225                 230                 235                 240

Ser Val Lys Pro Arg Ala Asn Ala Phe Val Ile Asn Leu Gly Asp Gln
                245                 250                 255

Leu Gln Ala Leu Ser Asn Gly Lys Tyr Arg Ser Val Trp His Arg Ala
            260                 265                 270

Ile Val Asn Ser Asp Lys Pro Arg Leu Ser Val Ala Ser Phe Leu Cys
            275                 280                 285

Pro Ser Asp Cys Ala Ile Ile Ser Ala Pro Lys Thr Leu Thr Glu Asp
            290                 295                 300

Gly Ser Pro Thr Ile Tyr Arg Asp Phe Thr Tyr Pro Glu Tyr Tyr Lys
305                 310                 315                 320

Lys Phe Trp Ser Arg Asn Leu Asp Gln Glu His Cys Met Glu Leu Phe
```

Lys Lys Gly Ser
            340

<210> SEQ ID NO 4
<211> LENGTH: 337
<212> TYPE: PRT
<213> ORGANISM: Unknown
<220> FEATURE:
<223> OTHER INFORMATION: Petunia

<400> SEQUENCE: 4

Met Glu Thr Lys Val Leu Ser Ser Gly Ile Arg His Ser Thr Leu Pro
1               5                   10                  15

Gln Asn Tyr Val Arg Pro Lys Ser Asp Arg Pro Arg Leu Ser Glu Val
            20                  25                  30

Ala Asn Cys Glu Asn Val Pro Val Ile Asp Leu Gly Cys Ala Asp Arg
        35                  40                  45

Thr Leu Ile Ile His Gln Ile Ser Glu Ala Cys Arg Leu Tyr Gly Phe
    50                  55                  60

Phe Gln Val Ile Asn His Gly Val Pro Lys Lys Ile Val Glu Glu Met
65                  70                  75                  80

Leu Glu Ile Ala Gly Glu Phe Phe Arg Leu Pro Val Glu Glu Lys Leu
                85                  90                  95

Lys Leu Tyr Ser Asp Asp Pro Ser Lys Thr Met Arg Leu Ser Thr Ser
            100                 105                 110

Phe Asn Val Lys Lys Glu Thr Val His Asn Trp Arg Asp Tyr Leu Arg
        115                 120                 125

Leu His Cys Tyr Pro Leu Glu Lys Tyr Ala Pro Glu Trp Pro Ser Asn
    130                 135                 140

Pro Ser Ser Phe Arg Glu Ile Val Ser Arg Tyr Cys Thr Glu Val Arg
145                 150                 155                 160

Gln Leu Gly Phe Arg Leu Gln Glu Ala Ile Ala Glu Ser Leu Gly Leu
                165                 170                 175

Glu Lys Glu Cys Ile Lys Asp Val Leu Gly Glu Gln Gly Gln His Met
            180                 185                 190

Ala Ile Asn Phe Tyr Pro Pro Cys Pro Glu Pro Glu Leu Thr Tyr Gly
        195                 200                 205

Leu Pro Ala His Thr Asp Pro Asn Ala Leu Thr Ile Leu Leu Gln Asp
    210                 215                 220

Leu Gln Val Ala Gly Leu Gln Val Leu Lys Asp Gly Lys Trp Leu Ala
225                 230                 235                 240

Val Lys Pro Gln Pro Asp Ala Phe Val Val Asn Leu Gly Asp Gln Leu
                245                 250                 255

Gln Ala Val Ser Asn Gly Arg Tyr Lys Ser Val Trp His Arg Ala Val
            260                 265                 270

Val Asn Thr Glu Asn Ala Arg Met Ser Val Ala Ser Phe Leu Cys Pro
        275                 280                 285

Cys Asp Ser Ala Lys Ile Ser Ala Pro Lys Leu Leu Thr Asp Asp Gly
    290                 295                 300

Ser Pro Ile Ile Tyr Arg Asp Phe Thr Tyr Ala Glu Tyr Tyr Lys Lys
305                 310                 315                 320

Phe Trp Ser Arg Asn Leu Asp Gln Glu His Cys Leu Glu Leu Phe Lys
                325                 330                 335

Asn

<210> SEQ ID NO 5
<211> LENGTH: 337
<212> TYPE: PRT
<213> ORGANISM: Solanum lycopersicum

<400> SEQUENCE: 5

Met Glu Thr Lys Val Ile Ser Ser Gly Ile Asn His Ser Thr Leu Pro
1               5                   10                  15

Gln Ser Tyr Ile Arg Pro Glu Ser Asp Arg Pro Arg Leu Ser Glu Val
            20                  25                  30

Val Asp Cys Glu Asn Val Pro Ile Ile Asp Leu Ser Cys Gly Asp Gln
        35                  40                  45

Ala Gln Ile Ile Arg Gln Ile Gly Glu Ala Cys Gln Thr Tyr Gly Phe
    50                  55                  60

Phe Gln Val Ile Asn His Gly Val Pro Lys Glu Val Val Glu Lys Met
65                  70                  75                  80

Leu Gly Val Ala Gly Glu Phe Phe Asn Leu Pro Val Glu Glu Lys Leu
                85                  90                  95

Lys Leu Tyr Ser Asp Asp Pro Ser Lys Thr Met Arg Leu Ser Thr Ser
            100                 105                 110

Phe Asn Val Lys Lys Glu Thr Val His Asn Trp Arg Asp Tyr Leu Arg
        115                 120                 125

Leu His Cys Tyr Pro Leu Glu Lys Tyr Ala Pro Glu Trp Pro Ser Asn
    130                 135                 140

Pro Ser Ser Phe Arg Glu Ile Val Ser Arg Tyr Cys Arg Glu Ile Arg
145                 150                 155                 160

Gln Leu Gly Phe Arg Leu Glu Glu Ala Ile Ala Glu Ser Leu Gly Leu
                165                 170                 175

Asp Lys Glu Cys Ile Lys Asp Val Leu Gly Glu Gln Gly Gln His Met
            180                 185                 190

Ala Ile Asn Tyr Tyr Pro Pro Cys Pro Gln Pro Glu Leu Thr Tyr Gly
        195                 200                 205

Leu Pro Ala His Thr Asp Pro Asn Ser Leu Thr Ile Leu Leu Gln Asp
    210                 215                 220

Leu Gln Val Ala Gly Leu Gln Val Leu Lys Asp Gly Lys Trp Leu Ala
225                 230                 235                 240

Val Lys Pro Gln Pro Asp Ala Phe Val Ile Asn Leu Gly Asp Gln Leu
                245                 250                 255

Gln Ala Val Ser Asn Gly Lys Tyr Arg Ser Val Trp His Arg Ala Ile
            260                 265                 270

Val Asn Ser Asp Gln Ala Arg Met Ser Val Ala Ser Phe Leu Cys Pro
        275                 280                 285

Cys Asp Ser Ala Lys Ile Ser Ala Pro Lys Leu Leu Thr Glu Asp Gly
    290                 295                 300

Ser Pro Val Ile Tyr Gln Asp Phe Thr Tyr Ala Glu Tyr Tyr Asn Lys
305                 310                 315                 320

Phe Trp Ser Arg Asn Leu Asp Gln Gln His Cys Leu Glu Leu Phe Lys
                325                 330                 335

Asn

<210> SEQ ID NO 6
<211> LENGTH: 320
<212> TYPE: PRT
<213> ORGANISM: Solanum lycopersicum

<400> SEQUENCE: 6

Met Met Thr Thr Thr Ser Val Leu Ser Ser Gly Phe Asn His Ser Thr
1               5                   10                  15

Leu Pro Gln Ser Tyr Val Arg Pro Glu Ser Gln Arg Pro Cys Met Ser
            20                  25                  30

Glu Val Val Asp Ser Asp Asp Leu Val Pro Val Ile Asp Met Ser Cys
        35                  40                  45

Thr Asp Arg Asn Val Ile Val His Gln Ile Gly Glu Ala Cys Arg Leu
    50                  55                  60

Tyr Gly Phe Phe Gln Val Ile Asn His Gly Val Ser Lys Lys Ala Met
65                  70                  75                  80

Asp Glu Met Leu Gly Thr Met Arg Leu Ser Thr Ser Phe Asn Val Lys
                85                  90                  95

Lys Glu Thr Val His Asn Trp Arg Asp Tyr Leu Arg Leu His Cys Tyr
            100                 105                 110

Pro Leu Asp Lys Tyr Ala Pro Glu Trp Pro Ser Asn Pro Ser Phe
            115                 120                 125

Arg Glu Ile Val Ser Lys Tyr Cys Met Glu Val Arg Glu Leu Gly Tyr
        130                 135                 140

Arg Leu Glu Glu Ala Ile Ser Glu Ser Leu Gly Leu Glu Lys Asp Cys
145                 150                 155                 160

Ile Lys Asn Val Leu Gly Glu Gln Gly Gln His Met Ala Ile Asn Phe
                165                 170                 175

Tyr Pro Gln Cys Pro Gln Pro Glu Leu Thr Tyr Gly Leu Pro Ala His
            180                 185                 190

Thr Asp Pro Asn Ala Ile Thr Ile Leu Leu Gln Asp Leu Gln Val Ala
        195                 200                 205

Gly Leu Gln Val Leu Lys Asp Gly Lys Trp Leu Ser Ile Lys Pro Gln
210                 215                 220

Pro Asn Ala Phe Val Ile Asn Leu Gly Asp Gln Leu Glu Ala Leu Ser
225                 230                 235                 240

Asn Gly Lys Tyr Lys Ser Ile Trp His Arg Ala Ile Val Asn Ser Asp
                245                 250                 255

Lys Ala Arg Met Ser Val Ala Ser Phe Leu Cys Pro Asn Asp Cys Ser
            260                 265                 270

Ile Ile Ser Ala Pro Lys Thr Leu Thr Glu Asp Gly Ser Ser Ala Ile
        275                 280                 285

Tyr Arg Asp Phe Thr Tyr Ala Glu Tyr Tyr Lys Phe Trp Ser Arg
        290                 295                 300

Asn Leu Asp Gln Glu Tyr Cys Leu Glu Leu Phe Lys Asn Asp Gly Thr
305                 310                 315                 320

<210> SEQ ID NO 7
<211> LENGTH: 1014
<212> TYPE: DNA
<213> ORGANISM: Solanum tuberosum

<400> SEQUENCE: 7
atggaaacga aagttatttc cagcggaatc caccactcta ctctccctca aagttacatc    60
cgacccgaat ccgataggcc acgtctatcg gatgtggtcg attgcgaaaa tgttccaata   120
attgacttag gttgcggaga ccaagctcaa ataatccgtc taattggaga agcttgtcaa   180
acttatggtt tctttcaggt aattaatcat ggtgtaccaa aggaagttgt agagaaaatg   240

```
ctaggggtag ctggggaatt tttcaatcta ccagtagaag agaagctaaa attgtattca      300
gatgatcctt caaagaccat gagattatct actagttta atgttaaaaa ggagacagtt      360
cataattgga gagattatct cagacttcat tgtcatcctc tggagaaata tgctcctgaa      420
tggccttcta atccatcgtc tttcaggat atcgtgagca gatattgcac ggaagttcga      480
caactcggat ttagattgga ggaagccata gcagagagcc tgggcttaga gaaagagtgt      540
attaaagatg tattgggaga acaaggccaa catatggcta tcaattttta tcctccttgt      600
ccacaaccag aactcacata tgggcttccg gcccatactg atccaaattc acttacaatt      660
cttcttcaag acttgcaagt ttctggtctt caagttctta aagatggtaa atggttggct      720
gtcaaacctc aaccagatgc ctttgtcatt aatcttggtg atcaattgca ggcagtaagt      780
aacggtaagt acaaaagtgt atggcatcga gctattgtga attcagatca agctaggatg      840
tcagtggctt cgttcctatg tccgtgcgat agcgcgaaaa tcagtgctcc aaaactcctg      900
acagaagatg gatctccagt catttatcag gacttcacgt atgctgagta ttacaagaag      960
ttctggagca ggaatttgga ccaggaacat tgtttggaac ttttcaagaa ttaa           1014

<210> SEQ ID NO 8
<211> LENGTH: 1029
<212> TYPE: DNA
<213> ORGANISM: Solanum tuberosum

<400> SEQUENCE: 8
atggaaacaa caagtgttct ttccggtgga ttcaaccact caaccctccc tgaatcttac       60
gttcgacctg aatcccaaag accccgcatg tctgaagttg ttgatcgtga tgatcttgtt      120
ccagttatcg atatgtcttg tactgatagg aacgttatcg ttcatcaaat tggcgaagct      180
tgtcgccttt atgggtttt ccaggtgata aatcacggtg tatcaaagaa ggttatggat      240
gaaatgttgg gggtagctca tgaatttttt aagcttccag tggaagaaaa gatgaaattg      300
tactcagatg atccatcaaa gactatgaga ttatcaacta gttttaatgt taagaaggaa      360
actgttcata attggagaga ttatcttagg ctacactgtt atcctttgga caaatatgcc      420
cctgaatggc cttctaatcc tccttctttc agggaaatag tgagcaaata ttgcatggaa      480
gttagacaag ttggatatag attagaagaa gcaatatcag agagcctagg gctcgagaaa      540
gattgtatta aaaatgtgtt gggtgaacaa ggacaacata tggctatcaa ttttatcct      600 ccatgtccac aacctgaact aacttatggg ttaccagccc atacagatcc aaatgcaatt      660
acaattcttc ttcaagattt gcaagtggct ggccttcaag ttcttaagga tggagaatgg      720
ttatctatta aacctcaacc tgatgccttt gtcatcaatc ttggtgatca attggaggca      780
ttgagtaatg aaagtataa aagtatatgg catagagcta ttgtaaattc agataaagca      840
aggatgtctg tggcttcttt cctctgtccc aatgattgtt ccattatcag tgctccaaaa      900
acctaaattg aagatggatc ttcagccatt tatcgagatt tcacttatac tgaatattat      960 gacaaattt ggagcaggaa tttagaccag gaatattgtt tagaacttt caagaacgat     1020 ggaaccctag                                                            1029

<210> SEQ ID NO 9
<211> LENGTH: 1014
<212> TYPE: DNA
<213> ORGANISM: Unknown
<220> FEATURE:
<223> OTHER INFORMATION: Petunia

<400> SEQUENCE: 9
```

-continued

```
atggaaacaa aagttctttc aagtggaatc cgtcattcta ccctccctca aaattatgtc    60
cgacccaaat ccgataggcc acgtctttca gaagtggcca attgtgaaaa cgttccagtt   120
attgacttgg gttgtgctga cagaactctc ataattcatc aaattagcga agcctgtcgt   180
ctttatggtt ttttccaggt aataaaccat ggtgtaccaa aaaaaatagt tgaggaaatg   240
ctagagatag ctggggagtt ttttaggcta ccagttgaag agaagcttaa gttgtattca   300
gatgacccct caaagaccat gagattatca actagtttta atgtaaagaa ggagacggtg   360
cacaattgga gagattatct cagacttcat tgttatcctc tggagaaata tgctcctgaa   420
tggccttcaa atccttcatc tttcaggaaa tcgtgagca gatattgcac ggaagttcga   480
caacttggat tcagattgca agaagccata gcagaaagct taggcttaga gaaagagtgt   540
ataaaggatg tgttaggtga acaaggtcaa catatggcta taaacttttta tcctccatgc   600 ccagaaccag aactcactta cgggctgcca gcccataccg atccaaatgc tcttacaatt   660
cttcttcaag acttgcaagt agctggtctc caagttctta agatggcaa atggttggct   720 gtcaaacctc agcccgatgc ctttgttgtt aatctcggtg atcaactgca ggcagtgagt   780
aacggaaggt acaaaagcgt atggcatcga gctgttgtaa atacagaaaa tgccaggatg   840
tctgtggctt cgttcttatg tccctgtgat agtgcaaaaa tcagtgctcc aaaactcctc   900
actgatgatg atctccaat aatttatcgg gacttcacgt atgcagagta ttacaagaag   960
ttctggagca ggaatttgga ccaagaacat tgtttggaac ttttcaagaa ttaa         1014
```

<210> SEQ ID NO 10
<211> LENGTH: 1023
<212> TYPE: DNA
<213> ORGANISM: Unknown
<220> FEATURE:
<223> OTHER INFORMATION: Petunia

<400> SEQUENCE: 10

```
atggaatcta atgttatttc cagcggaacc aaatacacaa acctccctaa aagttatgtt    60
cgcccagaat cccaacgacc tcggttatct gaagtagacg attgccaaga taatattcca   120
gttattgatt tgtgttgcag agacaataac gttatcattc aacaaattga agaagcttgt   180
cgtctttatg gcttttttca ggtaataaac catggtgtac caaagaaact aatagaggaa   240
atgctagggg tagctcatga ttttttcaag ctaccagtgg aagagaagat gaagttgtac   300
tcagatgatc catcaaagac catgagatta tcaacaagtt ttaatgtgaa gaaggaaact   360
gttcataatt ggagagacta tcttagattg cactgctatc ctttggagaa atatgccccct   420 gaatggcctt ctactccctc ttctttcagg gaaatcgtta gcagatattg catagaagtt   480
cgacaacttg gatatagatt acaagaagca atatcagaga gcttaggcct agagaaagat   540
tgtataaaaa atatattggg tgaacaaggt caacatatgg ctgttaatta ttaccctcca   600
tgtccagaac cagaactaac ttatggtttg ccagccccata ctgatcctaa tgcccttact   660
atacttcttc aagacttgca agtagcaggt cttcaagttc tcaaggatgg taaatggtta   720
tctgtgaaac ctcgggccaa tgcctttgtc atcaatcttg gtgatcaatt gcaggcgctg   780
agtaatggaa aatatagaag tgtatggcac agagctatag taaattcaga caaaccaagg   840
ctgtcagtgg cttcttttctt gtgtcctagt gattgtgcga taatcagtgc tccaaaaacc   900
ttaactgaag atgggtctcc aaccatttat cgggatttca cgtatccaga atattacaag   960
aaattttgga gcagaaattt agatcaagaa cactgtatgg aacttttcaa gaaaggaagc  1020
```

```
tag                                                                  1023

<210> SEQ ID NO 11
<211> LENGTH: 1014
<212> TYPE: DNA
<213> ORGANISM: Solanum lycopersicum

<400> SEQUENCE: 11
atggaaacca aagttatttc tagcggaatc aaccactcta ctcttcctca aagttacatc     60
cgacccgaat ccgatagacc acgtctatcg gaagtggtcg attgtgaaaa tgttccaata    120
attgacttaa gttgcggaga tcaagctcaa ataattcgtc aaattggaga agcttgtcaa    180
acttatggtt tctttcaggt aattaatcat ggtgtaccaa aggaagttgt agagaaaatg    240
ctaggggtag ctggggaatt tttcaattta ccagtagaag agaaactaaa attatattca    300
gatgatcctt caaagaccat gagattatca acaagtttta atgttaaaaa ggagacagtt    360
cataattgga gagattatct cagacttcat tgttatcctc tagagaagta tgctcctgaa    420
tggccttcta atccatcatc tttcagggaa atcgtgagca gatattgcag ggaaattcgt    480
caactcggat ttagattaga agaagccata gcagaaagcc tggggttaga taaagagtgt    540
ataaaagatg tattgggtga acaaggacaa catatggcta tcaattatta tcctccttgt    600
ccacaaccag aacttactta tgggcttccg gcccatactg atccaaattc acttacaatt    660
cttcttcaag acttgcaagt tgcgggtctt caagttctta aagatggcaa atggttagct    720
gtaaaacctc aacctgacgc ctttgtcatt aatcttgggg atcaattgca ggcagtaagt    780
aacggtaagt acagaagtgt atggcatcga gctattgtga attcagatca agctaggatg    840
tcagtggctt cgtttctatg tccgtgtgat agcgcgaaaa tcagtgcacc aaagctgctg    900
acagaagatg gatctccagt gatttatcaa gactttacgt atgctgagta ttacaacaag    960
ttctggagca ggaatttgga ccagcaacat tgtttggaac ttttcaagaa ctaa         1014

<210> SEQ ID NO 12
<211> LENGTH: 963
<212> TYPE: DNA
<213> ORGANISM: Solanum lycopersicum

<400> SEQUENCE: 12
atgatgacaa caacaagtgt tctttctagt ggattcaacc actcaaccct ccctcaatct     60
tacgttcgac ctgaatctca aagaccttgc atgtctgaag ttgttgatag cgacgatctt    120
gtcccagtca ttgatatgtc ttgtactgat aggaacgtta tcgttcatca aatcggtgaa    180
gcttgtcgtc tttatggggtt ttttcaggtg ataaatcacg gtgtgtcgaa gaaggcgatg    240
gatgaaatgt tagggactat gagattatca actagtttta atgttaagaa ggaaactgtt    300
cataattgga gagattatct taggctacat tgttatcctt ggacaaaata tgcccctgaa    360
tggccttcta atcctccttc tttcagggaa atagtaagca aatattgcat ggaagttaga    420
gagcttggat atagattgga agaagcaata tcagagagct tagggcttga aaggattgt     480 ataaaaaatg tgttaggtga acaaggacaa catatggcta tcaatttta tcctcagtgt    540 ccacaacctg aattaactta tgggttacca gcccatacag atccaaatgc aattacaatt    600
cttcttcaag atttgcaagt ggctggcctt caagttctta aggatggaaa atggttatct    660
attaaacctc agcctaatgc ctttgtcatc aatcttggtg atcaattgga ggcgttgagt    720
aatgggaagt ataaaagtat atggcataga gctattgtaa attcagacaa agcaaggatg    780
tctgtggctt cttttctctg tcccaatgat tgttccatta tcagtgctcc aaaaacctta    840
```

```
actgaagatg atcttctgc aatttatcga gatttcactt atgctgaata ttatgaaaaa    900
ttctggagca ggaatttaga tcaggaatat tgtttagaac ttttaagaa cgatggaacc    960 tag                                                                963
```

<210> SEQ ID NO 13
<211> LENGTH: 34
<212> TYPE: DNA
<213> ORGANISM: Artificial Sequence
<220> FEATURE:
<223> OTHER INFORMATION: S. Lycopersicum AttB1-F primer

<400> SEQUENCE: 13

```
aaaaagcagg cttcttgggt gaacaaggac aaca                              34
```

<210> SEQ ID NO 14
<211> LENGTH: 33
<212> TYPE: DNA
<213> ORGANISM: Artificial Sequence
<220> FEATURE:
<223> OTHER INFORMATION: S. Lycopersicum AttB2-R primer

<400> SEQUENCE: 14

```
agaaagctgg gtaaaacgaa gccactgaca tcc                               33
```

<210> SEQ ID NO 15
<211> LENGTH: 303
<212> TYPE: DNA
<213> ORGANISM: Artificial Sequence
<220> FEATURE:
<223> OTHER INFORMATION: silencing construct for SEQ ID Nos 11 and 12

<400> SEQUENCE: 15

```
ttgggtgaac aaggacaaca tatggctatc aattattatc ctccttgtcc acaaccagaa    60
cttacttatg gcttccggc ccatactgat ccaaattcac ttacaattct tcttcaagac   120
ttgcaagttg cgggtcttca agttcttaaa gatggcaaat ggttagctgt aaaacctcaa   180
cctgacgcct ttgtcattaa tcttggggat caattgcagg cagtaagtaa cggtaagtac   240
agaagtgtat ggcatcgagc tattgtgaat tcagatcaag ctaggatgtc agtggcttcg   300
ttt                                                                 303
```

<210> SEQ ID NO 16
<211> LENGTH: 337
<212> TYPE: PRT
<213> ORGANISM: Capsicum annuum

<400> SEQUENCE: 16

```
Met Glu Thr Lys Val Ile Ser Ser Gly Ile Arg His Ser Thr Leu Pro
1               5                   10                  15

Gln Ser Tyr Ile Arg Pro Glu Ser Asp Arg Pro Arg Leu Ser Glu Val
            20                  25                  30

Ala Asp Cys Glu Asn Val Pro Val Ile Asp Leu Gly Cys Ile Asp Arg
        35                  40                  45

Thr His Ile Ile Arg Gln Ile Gly Glu Ala Cys Arg Asn Tyr Gly Phe
    50                  55                  60

Phe Gln Val Ile Asn His Gly Val Pro Lys Glu Ile Val Glu Gln Met
65                  70                  75                  80

Leu Glu Val Ala Gly Glu Phe Phe Arg Leu Pro Val Glu Glu Lys Leu
                85                  90                  95
```

```
Lys Leu Tyr Ser Asp Asp Pro Ser Lys Thr Met Arg Leu Ser Thr Ser
            100                 105                 110

Phe Asn Val Lys Lys Glu Thr Val His Asn Trp Arg Asp Tyr Leu Arg
        115                 120                 125

Leu His Cys Tyr Pro Leu Glu Lys Tyr Ala Pro Glu Trp Pro Ser Asn
    130                 135                 140

Pro Ser Ser Phe Arg Glu Ile Val Ser Arg Tyr Cys Thr Glu Val Arg
145                 150                 155                 160

Gln Leu Gly Phe Arg Leu Gln Glu Ala Ile Ala Glu Ser Leu Gly Leu
                165                 170                 175

Glu Lys Glu Cys Ile Lys Asp Val Leu Gly Glu Gln Gly Gln His Met
            180                 185                 190

Ala Ile Asn Phe Tyr Pro Pro Cys Pro Gln Pro Glu Leu Thr Tyr Gly
        195                 200                 205

Leu Pro Ala His Thr Asp Pro Asn Ser Leu Thr Ile Leu Leu Gln Asp
    210                 215                 220

Leu Gln Val Ala Gly Leu Gln Val Leu Lys Asp Gly Lys Trp Leu Ala
225                 230                 235                 240

Val Lys Pro Gln Pro Asp Ala Phe Val Ile Asn Leu Gly Asp Gln Leu
                245                 250                 255

Gln Ala Val Ser Asn Gly Lys Tyr Lys Ser Val Trp His Arg Ala Ile
            260                 265                 270

Val Asn Ser Asp Lys Ala Arg Met Ser Val Ala Ser Phe Leu Cys Pro
        275                 280                 285

Cys Asp Ser Ala Lys Ile Ser Ala Pro Lys Leu Leu Thr Glu Asp Gly
    290                 295                 300

Ser Pro Val Ile Tyr Arg Asp Phe Thr Tyr Ala Glu Tyr Tyr Lys Lys
305                 310                 315                 320

Phe Trp Ser Arg Asn Leu Asp Gln Glu His Cys Leu Glu Leu Phe Lys
                325                 330                 335

Asn

<210> SEQ ID NO 17
<211> LENGTH: 342
<212> TYPE: PRT
<213> ORGANISM: Capsicum annuum

<400> SEQUENCE: 17

Met Glu Thr Lys Asn Val Leu Ser Ser Gly Thr Lys Tyr Ser Thr Leu
1               5                   10                  15

Pro Glu Thr Tyr Ile Arg Pro Glu Ser Gln Arg Pro Arg Leu Ser Glu
            20                  25                  30

Val Val Asp Cys Glu Asp Phe Ile Pro Val Ile Asp Met Ser Cys Thr
        35                  40                  45

Asp Arg Asn Ile Ile Val His Gln Ile Gly Gln Ala Cys Leu Leu Tyr
    50                  55                  60

Gly Phe Phe Gln Val Ile Asn His Asp Val Pro Lys Glu Val Ile Glu
65                  70                  75                  80

Gly Met Leu Gly Val Ala His Glu Phe Phe Lys Leu Pro Val Glu Glu
                85                  90                  95

Lys Met Lys Leu Tyr Ser Asp Asp Pro Ser Lys Thr Met Arg Leu Ser
            100                 105                 110

Thr Ser Phe Asn Val Lys Lys Glu Thr Val His Asn Trp Arg Asp Tyr
        115                 120                 125
```

```
Leu Arg Leu His Cys Tyr Pro Leu Asp Lys Tyr Ala Pro Glu Trp Pro
    130                 135                 140

Ser Asn Pro Ser Ser Phe Arg Glu Ile Val Ser Lys Tyr Cys Met Glu
145                 150                 155                 160

Val Arg Gln Leu Gly Tyr Arg Leu Glu Glu Ala Ile Ser Glu Ser Leu
                165                 170                 175

Gly Leu Gly Lys Asp Cys Ile Lys Asn Val Leu Gly Glu Gln Gly Gln
            180                 185                 190

His Met Ala Ile Asn Phe Tyr Pro Gln Cys Pro Gln Pro Glu Leu Thr
        195                 200                 205

Tyr Gly Leu Pro Ala His Thr Asp Pro Asn Ala Ile Thr Ile Leu Leu
    210                 215                 220

Gln Asp Leu Gln Val Glu Gly Leu Gln Val Leu Lys Asp Gly Lys Trp
225                 230                 235                 240

Leu Ser Val Lys Pro Gln Pro Asn Ala Phe Val Ile Asn Leu Gly Asp
                245                 250                 255

Gln Leu Gln Ala Leu Ser Asn Gly Lys Tyr Lys Ser Val Trp His Arg
            260                 265                 270

Ala Ile Val Asn Ser Asp Lys Ala Arg Met Ser Val Ala Ser Phe Leu
        275                 280                 285

Cys Pro Ser Asp Cys Ser Ile Ile Ser Ala Pro Lys Ala Leu Thr Glu
    290                 295                 300

Asp Gly Ser Ser Ala Ile Tyr Arg Asp Phe Thr Tyr Thr Glu Tyr Tyr
305                 310                 315                 320

Asn Lys Phe Trp Ser Arg Ser Leu Asp Gln Glu Arg Arg Leu Lys Leu
                325                 330                 335

Phe Lys Lys Val Tyr Thr
            340

<210> SEQ ID NO 18
<211> LENGTH: 337
<212> TYPE: PRT
<213> ORGANISM: Nicotiana benthamiana

<400> SEQUENCE: 18

Met Glu Ala Lys Val Leu Ser Ser Gly Ile Arg His Ser Thr Ile Pro
1               5                   10                  15

Gln Ser Tyr Ile Arg Pro Gln Ser Asp Arg Pro Arg Leu Ser Glu Val
            20                  25                  30

Ala Asp Cys Glu Asn Val Pro Val Asp Ile Gly Cys Gly Asp Arg
        35                  40                  45

Asn Leu Ile Val His Gln Ile Gly Glu Ala Cys Arg Leu Tyr Gly Phe
    50                  55                  60

Phe Gln Val Ile Asn His Gly Val Pro Lys Asn Leu Ile Asp Glu Met
65                  70                  75                  80

Leu Glu Ile Ala Gly Glu Phe Phe Arg Leu Pro Val Glu Glu Lys Leu
                85                  90                  95

Lys Leu Tyr Ser Asp Asp Pro Ser Lys Thr Met Arg Leu Ser Thr Ser
            100                 105                 110

Phe Asn Val Lys Lys Glu Lys Val His Asn Trp Arg Asp Tyr Leu Arg
        115                 120                 125

Leu His Cys Tyr Pro Leu Glu Asn Tyr Ala Pro Glu Trp Pro Ser Asn
    130                 135                 140

Pro Ser Ser Phe Arg Glu Ile Val Ser Arg Tyr Cys Met Glu Val Arg
145                 150                 155                 160
```

```
Gln Leu Gly Phe Arg Leu Gln Glu Ala Ile Ala Glu Ser Leu Gly Leu
                165                 170                 175

Glu Lys Glu Cys Ile Lys Asp Val Leu Gly Glu Gln Gly Gln His Met
            180                 185                 190

Ala Ile Asn Phe Tyr Pro Pro Cys Pro Gln Pro Glu Leu Thr Tyr Gly
        195                 200                 205

Leu Pro Ala His Thr Asp Pro Asn Ala Leu Thr Ile Leu Leu Gln Asp
    210                 215                 220

Leu Glu Val Ala Gly Leu Gln Val Leu Lys Asp Gly Glu Trp Leu Ala
225                 230                 235                 240

Val Lys Pro Gln Pro Asp Ala Phe Val Ile Asn Leu Gly Asp Gln Leu
                245                 250                 255

Gln Ala Val Ser Asn Gly Arg Tyr Lys Ser Val Trp His Arg Ala Ile
            260                 265                 270

Val Asn Ser Asp Lys Ala Arg Leu Ser Val Ala Ser Phe Leu Cys Pro
        275                 280                 285

Cys Asp Ser Ala Lys Ile Ser Ala Pro Lys Leu Leu Thr Glu Asp Gly
    290                 295                 300

Ser Pro Val Ile Tyr Gln Asp Phe Thr Tyr Ala Glu Tyr Tyr Lys Lys
305                 310                 315                 320

Phe Trp Ser Arg Asn Leu Asp Gln Glu His Cys Leu Glu Leu Phe Lys
                325                 330                 335

Asn

<210> SEQ ID NO 19
<211> LENGTH: 337
<212> TYPE: PRT
<213> ORGANISM: Nicotiana tabacum

<400> SEQUENCE: 19

Met Glu Thr Lys Val Leu Ser Ser Gly Ile Arg His Ser Thr Ile Pro
1               5                   10                  15

Gln Ser Tyr Ile Arg Pro Gln Ser Asp Arg Pro Arg Leu Ser Glu Val
                20                  25                  30

Val Asp Cys Glu Asn Val Pro Val Ile Asp Met Gly Cys Gly Asp Arg
            35                  40                  45

Asn His Ile Ile Arg Gln Ile Gly Glu Ala Cys His Leu Tyr Gly Phe
        50                  55                  60

Phe Gln Val Ile Asn His Gly Val Pro Thr Asn Leu Val Glu Glu Met
65                  70                  75                  80

Leu Glu Ile Ala Arg Glu Phe Phe Asn Leu Pro Val Glu Glu Lys Leu
                85                  90                  95

Lys Leu Tyr Ser Asp Asp Pro Ser Lys Thr Met Arg Leu Ser Thr Ser
                100                 105                 110

Phe Asn Val Lys Lys Glu Thr Val His Asn Trp Arg Asp Tyr Leu Arg
            115                 120                 125

Leu His Cys Tyr Pro Leu Glu Lys Tyr Ala Pro Glu Trp Pro Ser Asn
        130                 135                 140

Pro Ala Ser Phe Arg Glu Ile Val Ser Arg Tyr Cys Thr Glu Val Arg
145                 150                 155                 160

Gln Leu Gly Phe Arg Leu Gln Glu Ala Ile Ala Glu Ser Leu Gly Leu
                165                 170                 175

Glu Lys Val Cys Ile Lys Asp Val Leu Gly Glu Gln Gly Gln His Met
            180                 185                 190
```

```
Ala Ile Asn Phe Tyr Pro Pro Cys Pro Gln Pro Glu Leu Thr Tyr Gly
        195                 200                 205

Leu Pro Ala His Thr Asp Pro Asn Ala Leu Thr Ile Leu Leu Gln Asp
    210                 215                 220

Leu Gln Val Ala Gly Leu Gln Val Leu Lys Asp Gly Lys Trp Leu Ala
225                 230                 235                 240

Val Lys Pro Gln Pro Asp Ala Phe Val Ile Asn Leu Gly Asp Gln Leu
                245                 250                 255

Gln Ala Val Ser Asn Gly Arg Tyr Lys Ser Val Trp His Arg Ala Ile
                260                 265                 270

Val Asn Ser Asp Lys Ala Arg Leu Ser Val Ala Ser Phe Leu Cys Pro
            275                 280                 285

Cys Asp Ser Ala Lys Ile Ser Ala Pro Lys Leu Leu Thr Glu Asp Gly
        290                 295                 300

Ser Pro Val Ile Tyr Gln Asp Phe Thr Tyr Ala Glu Tyr Tyr Lys Lys
305                 310                 315                 320

Phe Trp Ser Arg Asn Leu Asp Gln Glu His Cys Leu Glu Phe Phe Lys
                325                 330                 335

Asn

<210> SEQ ID NO 20
<211> LENGTH: 1014
<212> TYPE: DNA
<213> ORGANISM: Capsicum annuum

<400> SEQUENCE: 20
atggaaacca aagttatttc agcggaatc cgccactcta ctcttcctca agttatatc      60 cgacccgaat ccgataggcc acgcctttct gaagtggctg attgtgaaaa tgttccggtt    120
atcgacttag gctgcattga ccgaactcac ataattcgtc aaatcggcga agcttgtcga    180
aattatggct tcttccaggt aattaatcat ggtgtaccaa aggaaattgt agaacaaatg    240
ctagaggtag ctggggaatt tttcaggtta ccagtagaag agaagctgaa attatattca    300
gatgaccctt caaagaccat gagattatct acaagtttta atgttaaaaa agagacggtt    360
cacaattgga gagattatct caggcttcac tgttatcctc ttgaaaaata tgcccctgaa    420
tggccttcta tccctcatc tttcaggaa atagtgagca gatactgcac ggaagttcga    480
caacttggat tcagattgca ggaagcaata gcagagagct aggcttaga gaaagagtgt    540 ataaaggatg tattggggga acaaggtcaa catatggcta tcaacttta tcctccatgt    600 ccacaaccag aactcactta tggacttcca gctcatactg atccaaattc acttactatt    660
cttctacaag acttgcaagt agctggcctt caggttctta agatggcaa atggttagct    720 gtcaaacctc agccagatgc ctttgtcatt aatcttggtg atcaattgca ggcagtgagt    780
aacggaaagt acaaaagcgt atggcataga gctattgtaa attcagacaa agccaggatg    840
tcagtggctt cgttcctttg cccatgtgat agcgcgaaaa tcagtgctcc aaaactcctc    900
actgaagatg gatctccagt catttatagg gatttcacct atgctgaata ttacaagaag    960
ttctggagca ggaatttgga tcaggaacat tgtttggaac ttttcaagaa ttaa           1014

<210> SEQ ID NO 21
<211> LENGTH: 1029
<212> TYPE: DNA
<213> ORGANISM: Capsicum annuum

<400> SEQUENCE: 21
```

```
atggaaacaa aaaatgttct ttctagtgga actaagtact caactctccc tgaaacgtac    60
attcgccctg aatcccaaag acctcgtctg tctgaagttg ttgattgtga agattttatt   120
cctgttatcg atatgtcttg cactgacagg aacattatcg ttcatcaaat tggccaagct   180
tgtcttcttt acgggttttt ccaggtgata aatcatgacg tgccaaagga ggtgatagag   240
ggaatgctag gggtagctca tgagtttttc aagcttccag tggaagaaaa gatgaaatta   300
tactcagatg atccatcaaa gactatgaga ttatcaacaa gttttaatgt gaagaaggaa   360
actgttcata attggagaga ttatcttaga ctgcactgtt atcctttgga caaatatgcc   420
cctgaatggc cttctaaccc ctcttctttc agggaaatag tgagcaagta ttgcatggaa   480
gttagacaac ttggatatag attggaagaa gccatatcag agagcctagg ccttgggaaa   540
gattgtataa aaaatgtgtt gggtgaacaa ggtcaacata tggctatcaa tttttaccct   600
cagtgtccac aacctgaact cacatatggc ctgccagccc atacagatcc aaatgccatt   660
actattcttc ttcaagattt gcaagtagaa ggtctccaag ttctcaagga tggaaaatgg   720
ttatctgtta aacctcagcc taatgccttt gtcatcaatc ttggtgatca attgcaggca   780
ttgagtaatg gaaagtacaa aagtgtatgg catagagcta ttgtaaattc agacaaagca   840
aggatgtctg tggcctcttt cctttgtccc tctgattgtt ccattatcag tgctccgaaa   900
gccttaactg aagatggatc ttcagccatt tatcgagatt tcacctatac agaatattac   960
aacaaattct ggagcaggag tttagaccag gaacgtcgtt tgaaacttttt caagaaggtt  1020
tatacatga                                                           1029

<210> SEQ ID NO 22
<211> LENGTH: 1014
<212> TYPE: DNA
<213> ORGANISM: Nicotiana benthamiana

<400> SEQUENCE: 22
atggaagcaa aagttctttc cagcggaatc cgccactcta ctatccctca aagttacatc    60
cgccctcaat ccgataggcc gcgccttttct gaagttgctg attgtgaaaa cgttccagta   120
gttgatatag gttgcggtga tagaaacctt attgttcatc aaattggtga agcctgtcgt   180
ctttatggtt ttttccaggt aattaatcat ggtgtaccaa agaatttaat agacgaaatg   240
ctagagatag ctggggaatt ttttaggctt ccagttgaag agaagttgaa attgtactca   300
gatgacccat cgaagacgat gagattgtcg actagtttta atgtgaaaaa ggagaaggtt   360
cacaattgga gagattatct cagacttcat tgttatcctc ttgaaaatta cgctcctgaa   420
tggccttcca atccttcctc tttcagggaa atcgtgagca gatattgcat ggaagttcga   480
caactcgggt tcagattgca ggaagccata gcagagagcc taggcttaga gaagagtgt    540
ataaaggatg tattgggcga acaaggtcaa cacatggcta tcaatttcta tcctccttgt   600
ccacaaccag aactcactta tgggctgcca gcacatactg atccaaatgc ccttacaatt   660
cttcttcaag acttagaagt agctggtctt caagttctta agatggcga atggttggcc    720
gtcaagcctc aaccagatgc ctttgtcatt aatcttggtg atcaactgca ggcagtgagt   780
aatgggagat acaaaagcgt atggcatcga gctattgtaa attcagacaa agccaggttg   840
tcagtggctt cgttcctttg tccgtgcgat agcgcgaaaa tcagtgctcc aaagctcctc   900
actgaagatg gatctcctgt catttatcag gactttacct atgctgagta ttacaaaaag   960
ttctggagca ggaatttgga ccaggaacat tgtttggaac ttttcaagaa ctaa         1014
```

<210> SEQ ID NO 23
<211> LENGTH: 1014
<212> TYPE: DNA
<213> ORGANISM: Nicotiana tabacum

<400> SEQUENCE: 23

| | | | | | |
|---|---|---|---|---|---|
| atggaagcaa | aagttctttc | cagcggaatc | cgccactcta | ctatccctca | aagttacatc | 60 |
| cgccctcaat | ccgataggcc | gcgcctttct | gaagttgctg | attgtgaaaa | cgttccagta | 120 |
| gttgatatag | gttgcggtga | tagaaacctt | attgttcatc | aaattggtga | agcctgtcgt | 180 |
| ctttatggtt | ttttccaggt | aattaatcat | ggtgtaccaa | agaatttaat | agacgaaatg | 240 |
| ctagagatag | ctggggaatt | ttttaggctt | ccagttgaag | agaagttgaa | attgtactca | 300 |
| gatgacccat | cgaagacgat | gagattgtcg | actagtttta | atgtgaaaaa | ggagaaggtt | 360 |
| cacaattgga | gagattatct | cagacttcat | tgttatcctc | ttgaaaatta | cgctcctgaa | 420 |
| tggccttcca | atccttcctc | tttcaggaa | atcgtgagca | gatattgcat | ggaagttcga | 480 |
| caactcgggt | tcagattgca | ggaagccata | gcagagagc | taggcttaga | gaaagagtgt | 540 |
| ataaaggatg | tattgggcga | acaaggtcaa | cacatggcta | tcaatttcta | tcctccttgt | 600 |
| ccacaaccag | aactcactta | tgggctgcca | gcacatactg | atccaaatgc | ccttacaatt | 660 |
| cttcttcaag | acttagaagt | agctggtctt | caagttctta | agatggcga | atggttggcc | 720 |
| gtcaagcctc | aaccagatgc | ctttgtcatt | aatcttggtg | atcaactgca | ggcagtgagt | 780 |
| aatgggagat | acaaaagcgt | atggcatcga | gctattgtaa | attcagacaa | agccaggttg | 840 |
| tcagtggctt | cgttcctttg | tccgtgcgat | agcgcgaaaa | tcagtgctcc | aaagctcctc | 900 |
| actgaagatg | gatctcctgt | catttatcag | gactttacct | atgctgagta | ttacaaaaag | 960 |
| ttctggagca | ggaatttgga | ccaggaacat | tgtttggaac | ttttcaagaa | ctaa | 1014 |

<210> SEQ ID NO 24
<211> LENGTH: 409
<212> TYPE: DNA
<213> ORGANISM: Artificial Sequence
<220> FEATURE:
<223> OTHER INFORMATION: DMR6 silencing construct

<400> SEQUENCE: 24

| | | | | | |
|---|---|---|---|---|---|
| acaactcggg | ttcagattgc | aggaagccat | agcagagagc | ctaggcttag | agaaagagtg | 60 |
| tataaaggat | gtattgggcg | aacaaggtca | acacatggct | atcaatttct | atcctccttg | 120 |
| tccacaacca | gaactcactt | atgggctgcc | agcacatact | gatccaaatg | cccttacaat | 180 |
| tcttcttcaa | gacttagaag | tagctggtct | tcaagttctt | aaagatggcg | aatggttggc | 240 |
| cgtcaagcct | caaccagatg | cctttgtcat | taatcttggt | gatcaactgc | aggcagtgag | 300 |
| taatgggaga | tacaaaagcg | tatggcatcg | agctattgta | aattcagaca | aagccaggtt | 360 |
| gtcagtggct | tcgttccttt | gtccgtgcga | tagcgcgaaa | atcagtgct | | 409 |

<210> SEQ ID NO 25
<211> LENGTH: 337
<212> TYPE: PRT
<213> ORGANISM: Capsicum annuum
<220> FEATURE:
<221> NAME/KEY: VARIANT
<222> LOCATION: 215
<223> OTHER INFORMATION: single-nucleotide polymorphism

<400> SEQUENCE: 25

Met Glu Thr Lys Val Ile Ser Ser Gly Ile Arg His Ser Thr Leu Pro

```
                1               5                  10                    15
            Gln Ser Tyr Ile Arg Pro Glu Ser Asp Arg Pro Arg Leu Ser Glu Val
                            20                 25                  30
            Ala Asp Cys Glu Asn Val Pro Val Ile Asp Leu Gly Cys Ile Asp Arg
                            35                 40                 45
            Thr His Ile Ile Arg Gln Ile Gly Glu Ala Cys Arg Asn Tyr Gly Phe
                    50                 55                 60
            Phe Gln Val Ile Asn His Gly Val Pro Lys Glu Ile Val Glu Gln Met
            65                 70                 75                 80
            Leu Glu Val Ala Gly Glu Phe Phe Arg Leu Pro Val Glu Glu Lys Leu
                            85                  90                 95
            Lys Leu Tyr Ser Asp Asp Pro Ser Lys Thr Met Arg Leu Ser Thr Ser
                            100                105                110
            Phe Asn Val Lys Lys Glu Thr Val His Asn Trp Arg Asp Tyr Leu Arg
                            115                120                125
            Leu His Cys Tyr Pro Leu Glu Lys Tyr Ala Pro Glu Trp Pro Ser Asn
                    130                135                140
            Pro Ser Phe Arg Glu Ile Val Ser Arg Tyr Cys Thr Glu Val Arg
            145                150                155                160
            Gln Leu Gly Phe Arg Leu Gln Glu Ala Ile Ala Glu Ser Leu Gly Leu
                            165                170                175
            Glu Lys Glu Cys Ile Lys Asp Val Leu Gly Glu Gln Gly Gln His Met
                            180                185                190
            Ala Ile Asn Phe Tyr Pro Pro Cys Pro Gln Pro Glu Leu Thr Tyr Gly
                    195                200                205
            Leu Pro Ala His Thr Asp Leu Asn Ser Leu Thr Ile Leu Leu Gln Asp
            210                215                220
            Leu Gln Val Ala Gly Leu Gln Val Leu Lys Asp Gly Lys Trp Leu Ala
            225                230                235                240
            Val Lys Pro Gln Pro Asp Ala Phe Val Ile Asn Leu Gly Asp Gln Leu
                            245                250                255
            Gln Ala Val Ser Asn Gly Lys Tyr Lys Ser Val Trp His Arg Ala Ile
                            260                265                270
            Val Asn Ser Asp Lys Ala Arg Met Ser Val Ala Ser Phe Leu Cys Pro
                    275                280                285
            Cys Asp Ser Ala Lys Ile Ser Ala Pro Lys Leu Leu Thr Glu Asp Gly
            290                295                300
            Ser Pro Val Ile Tyr Arg Asp Phe Thr Tyr Ala Glu Tyr Tyr Lys Lys
            305                310                315                320
            Phe Trp Ser Arg Asn Leu Asp Gln Glu His Cys Leu Glu Leu Phe Lys
                            325                330                335
            Asn

<210> SEQ ID NO 26
<211> LENGTH: 337
<212> TYPE: PRT
<213> ORGANISM: Capsicum annuum
<220> FEATURE:
<221> NAME/KEY: VARIANT
<222> LOCATION: 175
<223> OTHER INFORMATION: single-nucleotide polymorphism

<400> SEQUENCE: 26

Met Glu Thr Lys Val Ile Ser Ser Gly Ile Arg His Ser Thr Leu Pro
            1               5                  10                 15
```

```
Gln Ser Tyr Ile Arg Pro Glu Ser Asp Arg Pro Arg Leu Ser Glu Val
                20                  25                  30

Ala Asp Cys Glu Asn Val Pro Val Ile Asp Leu Gly Cys Ile Asp Arg
            35                  40                  45

Thr His Ile Ile Arg Gln Ile Gly Glu Ala Cys Arg Asn Tyr Gly Phe
        50                  55                  60

Phe Gln Val Ile Asn His Gly Val Pro Lys Glu Ile Val Glu Gln Met
65                  70                  75                  80

Leu Glu Val Ala Gly Glu Phe Phe Arg Leu Pro Val Glu Glu Lys Leu
                85                  90                  95

Lys Leu Tyr Ser Asp Asp Pro Ser Lys Thr Met Arg Leu Ser Thr Ser
            100                 105                 110

Phe Asn Val Lys Lys Glu Thr Val His Asn Trp Arg Asp Tyr Leu Arg
        115                 120                 125

Leu His Cys Tyr Pro Leu Glu Lys Tyr Ala Pro Glu Trp Pro Ser Asn
    130                 135                 140

Pro Ser Ser Phe Arg Glu Ile Val Ser Arg Tyr Cys Thr Glu Val Arg
145                 150                 155                 160

Gln Leu Gly Phe Arg Leu Gln Glu Ala Ile Ala Glu Ser Leu Ser Leu
                165                 170                 175

Glu Lys Glu Cys Ile Lys Asp Val Leu Gly Glu Gln Gly Gln His Met
            180                 185                 190

Ala Ile Asn Phe Tyr Pro Pro Cys Pro Gln Pro Glu Leu Thr Tyr Gly
        195                 200                 205

Leu Pro Ala His Thr Asp Pro Asn Ser Leu Thr Ile Leu Leu Gln Asp
    210                 215                 220

Leu Gln Val Ala Gly Leu Gln Val Leu Lys Asp Gly Lys Trp Leu Ala
225                 230                 235                 240

Val Lys Pro Gln Pro Asp Ala Phe Val Ile Asn Leu Gly Asp Gln Leu
                245                 250                 255

Gln Ala Val Ser Asn Gly Lys Tyr Lys Ser Val Trp His Arg Ala Ile
            260                 265                 270

Val Asn Ser Asp Lys Ala Arg Met Ser Val Ala Ser Phe Leu Cys Pro
        275                 280                 285

Cys Asp Ser Ala Lys Ile Ser Ala Pro Lys Leu Leu Thr Glu Asp Gly
    290                 295                 300

Ser Pro Val Ile Tyr Arg Asp Phe Thr Tyr Ala Glu Tyr Tyr Lys Lys
305                 310                 315                 320

Phe Trp Ser Arg Asn Leu Asp Gln Glu His Cys Leu Glu Leu Phe Lys
                325                 330                 335

Asn

<210> SEQ ID NO 27
<211> LENGTH: 337
<212> TYPE: PRT
<213> ORGANISM: Capsicum annuum
<220> FEATURE:
<221> NAME/KEY: VARIANT
<222> LOCATION: 119
<223> OTHER INFORMATION: single-nucleotide polymorphism

<400> SEQUENCE: 27

Met Glu Thr Lys Val Ile Ser Ser Gly Ile Arg His Ser Thr Leu Pro
1               5                   10                  15

Gln Ser Tyr Ile Arg Pro Glu Ser Asp Arg Pro Arg Leu Ser Glu Val
                20                  25                  30
```

Ala Asp Cys Glu Asn Val Pro Val Ile Asp Leu Gly Cys Ile Asp Arg
         35                  40                  45

Thr His Ile Ile Arg Gln Ile Gly Glu Ala Cys Arg Asn Tyr Gly Phe
     50                  55                  60

Phe Gln Val Ile Asn His Gly Val Pro Lys Glu Ile Val Glu Gln Met
 65                  70                  75                  80

Leu Glu Val Ala Gly Glu Phe Phe Arg Leu Pro Val Glu Glu Lys Leu
                 85                  90                  95

Lys Leu Tyr Ser Asp Asp Pro Ser Lys Thr Met Arg Leu Ser Thr Ser
             100                 105                 110

Phe Asn Val Lys Lys Glu Met Val His Asn Trp Arg Asp Tyr Leu Arg
             115                 120                 125

Leu His Cys Tyr Pro Leu Glu Lys Tyr Ala Pro Glu Trp Pro Ser Asn
         130                 135                 140

Pro Ser Ser Phe Arg Glu Ile Val Ser Arg Tyr Cys Thr Glu Val Arg
145                 150                 155                 160

Gln Leu Gly Phe Arg Leu Gln Glu Ala Ile Ala Glu Ser Leu Gly Leu
                 165                 170                 175

Glu Lys Glu Cys Ile Lys Asp Val Leu Gly Glu Gln Gly Gln His Met
             180                 185                 190

Ala Ile Asn Phe Tyr Pro Pro Cys Pro Gln Pro Glu Leu Thr Tyr Gly
         195                 200                 205

Leu Pro Ala His Thr Asp Pro Asn Ser Leu Thr Ile Leu Leu Gln Asp
     210                 215                 220

Leu Gln Val Ala Gly Leu Gln Val Leu Lys Asp Gly Lys Trp Leu Ala
225                 230                 235                 240

Val Lys Pro Gln Pro Asp Ala Phe Val Ile Asn Leu Gly Asp Gln Leu
                 245                 250                 255

Gln Ala Val Ser Asn Gly Lys Tyr Lys Ser Val Trp His Arg Ala Ile
             260                 265                 270

Val Asn Ser Asp Lys Ala Arg Met Ser Val Ala Ser Phe Leu Cys Pro
         275                 280                 285

Cys Asp Ser Ala Lys Ile Ser Ala Pro Lys Leu Leu Thr Glu Asp Gly
     290                 295                 300

Ser Pro Val Ile Tyr Arg Asp Phe Thr Tyr Ala Glu Tyr Tyr Lys Lys
305                 310                 315                 320

Phe Trp Ser Arg Asn Leu Asp Gln Glu His Cys Leu Glu Leu Phe Lys
                 325                 330                 335

Asn

<210> SEQ ID NO 28
<211> LENGTH: 342
<212> TYPE: PRT
<213> ORGANISM: Capsicum annuum
<220> FEATURE:
<221> NAME/KEY: VARIANT
<222> LOCATION: 135
<223> OTHER INFORMATION: single-nucleotide polymorphism

<400> SEQUENCE: 28

Met Glu Thr Lys Asn Val Leu Ser Ser Gly Thr Lys Tyr Ser Thr Leu
1               5                   10                  15

Pro Glu Thr Tyr Ile Arg Pro Glu Ser Gln Arg Pro Arg Leu Ser Glu
             20                  25                  30

Val Val Asp Cys Glu Asp Phe Ile Pro Val Ile Asp Met Ser Cys Thr

```
            35                  40                  45
Asp Arg Asn Ile Ile Val His Gln Ile Gly Gln Ala Cys Leu Leu Tyr
 50                  55                  60

Gly Phe Phe Gln Val Ile Asn His Asp Val Pro Lys Glu Val Ile Glu
 65                  70                  75                  80

Gly Met Leu Gly Val Ala His Glu Phe Phe Lys Leu Pro Val Glu Glu
                 85                  90                  95

Lys Met Lys Leu Tyr Ser Asp Asp Pro Ser Lys Thr Met Arg Leu Ser
            100                 105                 110

Thr Ser Phe Asn Val Lys Lys Glu Thr Val His Asn Trp Arg Asp Tyr
        115                 120                 125

Leu Arg Leu His Cys Tyr Leu Leu Asp Lys Tyr Ala Pro Glu Trp Pro
130                 135                 140

Ser Asn Pro Ser Ser Phe Arg Glu Ile Val Ser Lys Tyr Cys Met Glu
145                 150                 155                 160

Val Arg Gln Leu Gly Tyr Arg Leu Glu Glu Ala Ile Ser Glu Ser Leu
                165                 170                 175

Gly Leu Gly Lys Asp Cys Ile Lys Asn Val Leu Gly Glu Gln Gly Gln
            180                 185                 190

His Met Ala Ile Asn Phe Tyr Pro Gln Cys Pro Gln Pro Glu Leu Thr
        195                 200                 205

Tyr Gly Leu Pro Ala His Thr Asp Pro Asn Ala Ile Thr Ile Leu Leu
210                 215                 220

Gln Asp Leu Gln Val Glu Gly Leu Gln Val Leu Lys Asp Gly Lys Trp
225                 230                 235                 240

Leu Ser Val Lys Pro Gln Pro Asn Ala Phe Val Ile Asn Leu Gly Asp
                245                 250                 255

Gln Leu Gln Ala Leu Ser Asn Gly Lys Tyr Lys Ser Val Trp His Arg
            260                 265                 270

Ala Ile Val Asn Ser Asp Lys Ala Arg Met Ser Val Ala Ser Phe Leu
        275                 280                 285

Cys Pro Ser Asp Cys Ser Ile Ile Ser Ala Pro Lys Ala Leu Thr Glu
290                 295                 300

Asp Gly Ser Ser Ala Ile Tyr Arg Asp Phe Thr Tyr Thr Glu Tyr Tyr
305                 310                 315                 320

Asn Lys Phe Trp Ser Arg Ser Leu Asp Gln Glu Arg Arg Leu Lys Leu
                325                 330                 335

Phe Lys Lys Val Tyr Thr
            340

<210> SEQ ID NO 29
<211> LENGTH: 1014
<212> TYPE: DNA
<213> ORGANISM: Capsicum annuum
<220> FEATURE:
<221> NAME/KEY: misc_feature
<222> LOCATION: 644
<223> OTHER INFORMATION: single-nucleotide polymorphism

<400> SEQUENCE: 29
atggaaacca aagttatttc cagcggaatc cgccactcta ctcttcctca agttatatc      60 cgacccgaat ccgataggcc acgccttttct gaagtggctg attgtgaaaa tgttccggtt    120
atcgacttag ctgcattga ccgaactcac ataattcgtc aaatcggcga agcttgtcga     180
aattatggct tcttccaggt aattaatcat ggtgtaccaa aggaaattgt agaacaaatg    240
```

| | |
|---|---|
| ctagaggtag ctggggaatt tttcaggtta ccagtagaag agaagctgaa attatattca | 300 |
| gatgacccett caaagaccat gagattatct acaagttttta atgttaaaaa agagacggtt | 360 |
| cacaattgga gagattatct caggcttcac tgttatcctc ttgaaaaata tgcccctgaa | 420 |
| tggccttcta atccctcatc tttcaggaaa atagtgagca gatactgcac ggaagttcga | 480 |
| caacttggat tcagattgca ggaagcaata gcagagagct taggcttaga gaaagagtgt | 540 |
| ataaaggatg tattgggga acaaggtcaa catatggcta tcaacttttta tcctccatgt | 600 |
| ccacaaccag aactcactta tggacttcca gctcatactg atctaaattc acttactatt | 660 |
| cttctacaag acttgcaagt agctggcctt caggttctta aagatggcaa atggttagct | 720 |
| gtcaaacctc agccagatgc ctttgtcatt aatcttggtg atcaattgca ggcagtgagt | 780 |
| aacggaaagt acaaaagcgt atggcataga gctattgtaa attcagacaa agccaggatg | 840 |
| tcagtggctt cgttcctttg cccatgtgat agcgcgaaaa tcagtgctcc aaaactcctc | 900 |
| actgaagatg gatctccagt catttatagg gatttcacct atgctgaata ttacaagaag | 960 |
| ttctggagca ggaatttgga tcaggaacat tgtttggaac ttttcaagaa ttaa | 1014 |

<210> SEQ ID NO 30
<211> LENGTH: 1014
<212> TYPE: DNA
<213> ORGANISM: Capsicum annuum
<220> FEATURE:
<221> NAME/KEY: misc_feature
<222> LOCATION: 523
<223> OTHER INFORMATION: single-nucleotide polymorphism

<400> SEQUENCE: 30

| | |
|---|---|
| atggaaacca aagttatttc cagcggaatc cgccactcta ctcttcctca aagttatatc | 60 |
| cgacccgaat ccgataggcc acgcctttct gaagtggctg attgtgaaaa tgttccggtt | 120 |
| atcgacttag gctgcattga ccgaactcac ataattcgtc aaatcggcga agcttgtcga | 180 |
| aattatggct tcttccaggt aattaatcat ggtgtaccaa aggaaattgt agaacaaatg | 240 |
| ctagaggtag ctggggaatt tttcaggtta ccagtagaag agaagctgaa attatattca | 300 |
| gatgacccett caaagaccat gagattatct acaagttttta atgttaaaaa agagacggtt | 360 |
| cacaattgga gagattatct caggcttcac tgttatcctc ttgaaaaata tgcccctgaa | 420 |
| tggccttcta atccctcatc tttcaggaaa atagtgagca gatactgcac ggaagttcga | 480 |
| caacttggat tcagattgca ggaagcaata gcagagagct taagcttaga gaaagagtgt | 540 |
| ataaaggatg tattgggga acaaggtcaa catatggcta tcaacttttta tcctccatgt | 600 |
| ccacaaccag aactcactta tggacttcca gctcatactg atccaaattc acttactatt | 660 |
| cttctacaag acttgcaagt agctggcctt caggttctta aagatggcaa atggttagct | 720 |
| gtcaaacctc agccagatgc ctttgtcatt aatcttggtg atcaattgca ggcagtgagt | 780 |
| aacggaaagt acaaaagcgt atggcataga gctattgtaa attcagacaa agccaggatg | 840 |
| tcagtggctt cgttcctttg cccatgtgat agcgcgaaaa tcagtgctcc aaaactcctc | 900 |
| actgaagatg gatctccagt catttatagg gatttcacct atgctgaata ttacaagaag | 960 |
| ttctggagca ggaatttgga tcaggaacat tgtttggaac ttttcaagaa ttaa | 1014 |

<210> SEQ ID NO 31
<211> LENGTH: 1014
<212> TYPE: DNA
<213> ORGANISM: Capsicum annuum
<220> FEATURE:
<221> NAME/KEY: misc_feature
<222> LOCATION: 356
<223> OTHER INFORMATION: single-nucleotide polymorphism

<400> SEQUENCE: 31

```
atggaaacca aagttatttc cagcggaatc cgccactcta ctcttcctca agttatatc      60
cgacccgaat ccgataggcc acgccttcct gaagtggctg attgtgaaaa tgttccggtt   120
atcgacttag gctgcattga ccgaactcac ataattcgtc aaatcggcga agcttgtcga   180
aattatggct tcttccaggt aattaatcat ggtgtaccaa aggaaattgt agaacaaatg   240
ctagaggtag ctggggaatt tttcaggtta ccagtagaag agaagctgaa attatattca   300
gatgacccct caaagaccat gagattatct acaagtttta atgttaaaaa agagatggtt   360
cacaattgga gagattatct caggcttcac tgttatcctc ttgaaaaata tgcccctgaa   420
tggccttcta tccctcatc tttcaggaa atagtgagca gatactgcac ggaagttcga   480
caacttggat tcagattgca ggaagcaata gcagagagct taggcttaga gaaagagtgt   540
ataaaggatg tattggggga acaaggtcaa catatggcta tcaactttta tcctccatgt   600
ccacaaccag aactcactta tggacttcca gctcatactg atccaaattc acttactatt   660
cttctacaag acttgcaagt agctggcctt caggttctta aagatggcaa atggttagct   720
gtcaaacctc agccagatgc ctttgtcatt aatcttggtg atcaattgca ggcagtgagt   780
aacggaaagt acaaaagcgt atggcataga gctattgtaa attcagacaa agccaggatg   840
tcagtggctt cgttcctttg cccatgtgat agcgcgaaaa tcagtgctcc aaaactcctc   900
actgaagatg gatctccagt catttatagg gatttcacct atgctgaata ttacaagaag   960
ttctggagca ggaatttgga tcaggaacat tgtttggaac ttttcaagaa ttaa           1014
```

<210> SEQ ID NO 32
<211> LENGTH: 1029
<212> TYPE: DNA
<213> ORGANISM: Capsicum annuum
<220> FEATURE:
<221> NAME/KEY: misc_feature
<222> LOCATION: 404
<223> OTHER INFORMATION: single-nucleotide polymorphism

<400> SEQUENCE: 32

```
atggaaacaa aaaatgttct ttctagtgga actaagtact caactctccc tgaaacgtac      60
attcgccctg aatcccaaag acctcgtctg tctgaagttg ttgattgtga agatttttatt   120
cctgttatcg atatgtcttg cactgacagg aacattatcg ttcatcaaat tggccaagct   180
tgtcttcttt acgggttttt ccaggtgata aatcatgacg tgccaaagga ggtgatagag   240
ggaatgctag gggtagctca tgagtttttc aagcttccag tggaagaaaa gatgaaatta   300
tactcagatg atccatcaaa gactatgaga ttatcaacaa gttttaatgt gaagaaggaa   360
actgttcata attggagaga ttatcttaga ctgcactgtt atcttttgga caaatatgcc   420
cctgaatggc cttctaaccc ctcttctttc agggaaatag tgagcaagta ttgcatggaa   480
gttagacaac ttggatatag attggaagaa gccatatcag agagcctagg ccttgggaaa   540
gattgtataa aaaatgtgtt gggtgaacaa ggtcaacata tggctatcaa ttttttacccct   600
cagtgtccac aacctgaact cacatatggc ctgccagccc atacagatcc aaatgccatt   660
actattcttc ttcaagattt gcaagtagaa ggtctccaag ttctcaagga tggaaaatgg   720
ttatctgtta aacctcagcc taatgccttt gtcatcaatc ttggtgatca attgcaggca   780
ttgagtaatg gaaagtacaa aagtgtatgg catagagcta ttgtaaattc agacaaagca   840
```

```
aggatgtctg tggcctcttt cctttgtccc tctgattgtt ccattatcag tgctccgaaa        900
gccttaactg aagatggatc ttcagccatt tatcgagatt tcacctatac agaatattac        960
aacaaattct ggagcaggag tttagaccag gaacgtcgtt tgaaactttt caagaaggtt       1020
tatacatga                                                               1029
```

The invention claimed is:

1. An isolated *Capsicum annuum* pepper plant resistant to *Phytophthora capsici*, wherein the pepper plant comprises a mutated first coding sequence comprising SEQ ID NO: 29 and comprises a mutated second coding sequence comprising SEQ ID NO: 32, and wherein the plant exhibits resistance to *Phytophthora capsici*.

2. The pepper plant of claim 1, further comprising a mutated first protein comprising SEQ ID NO: 25 and a mutated second protein comprising SEQ ID NO: 28.

3. A seed, tissue, or plant part of the pepper plant of claim 1, wherein the seed, tissue, or plant part comprises the mutated first coding sequence and the mutated second coding sequence.

4. The seed, tissue, or plant part of claim 3, wherein the seed, tissue, or plant part further comprises a mutated first protein comprising SEQ ID NO: 25, and a mutated second protein comprising SEQ ID NO: 28.

5. A method for obtaining the isolated *Capsicum annuum* pepper plant of claim 1, comprising introducing a mutation into a coding sequence of a first gene to produce a mutated first coding sequence comprising SEQ ID NO: 29 and introducing a mutation into a coding sequence of a second gene to produce a mutated second coding sequence comprising SEQ ID NO: 32, wherein the mutated first coding sequence encodes a mutated first protein and the mutated second coding sequence encodes a mutated second protein.

6. The method of claim 5, wherein the mutated first protein comprises SEQ ID NO: 25 and the mutated second protein comprises SEQ ID NO: 28.

7. An isolated *Capsicum annuum* pepper plant resistant to *Phytophthora capsici*, wherein the pepper plant comprises a mutated first protein comprising SEQ ID NO: 25 and a mutated second protein comprising SEQ ID NO: 28, and wherein the plant exhibits resistance to *Phytophthora capsici*.

8. The pepper plant of claim 7, further comprising a mutated first coding sequence comprising SEQ ID NO: 29 and a mutated second coding sequence comprising SEQ ID NO: 32.

9. A seed, tissue, or plant part of the pepper plant of claim 7, wherein the seed, tissue, or plant part comprises the mutated first protein and the mutated second protein.

10. The seed, tissue, or plant part of claim 9, wherein the seed, tissue, or plant part further comprises a mutated first coding sequence comprising SEQ ID NO: 29 and a mutated second coding sequence comprising SEQ ID NO: 32.

* * * * *